(12) United States Patent
Hueil et al.

(10) Patent No.: US 7,500,979 B2
(45) Date of Patent: Mar. 10, 2009

(54) SURGICAL STAPLING DEVICE WITH MULTIPLE STACKED ACTUATOR WEDGE CAMS FOR DRIVING STAPLE DRIVERS

(75) Inventors: Joseph C. Hueil, Loveland, OH (US); Jerome R. Morgan, Cincinnati, OH (US); Frederick E. Shelton, IV, New Vienna, OH (US); Jeffrey S. Swayze, Hamilton, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 14 days.

(21) Appl. No.: 11/712,315

(22) Filed: Feb. 28, 2007

(65) Prior Publication Data
US 2007/0262116 A1    Nov. 15, 2007

Related U.S. Application Data

(63) Continuation-in-part of application No. 11/216,562, filed on Aug. 31, 2005.

(51) Int. Cl.
*A61B 17/00* (2006.01)
(52) U.S. Cl. .................. 606/139; 227/175.1; 227/176.1
(58) Field of Classification Search .............. 227/175.1, 227/176.1, 180.1; 606/139
See application file for complete search history.

(56) References Cited

U.S. PATENT DOCUMENTS

| | | | |
|---|---|---|---|
| 2,037,727 | A | 4/1936 | La Chapelle |
| 3,551,987 | A | 1/1971 | Wilkinson |
| 3,643,851 | A | 2/1972 | Green et al. |
| 3,662,939 | A | 5/1972 | Bryan |
| 3,717,294 | A | 2/1973 | Green |
| 3,819,100 | A | 6/1974 | Noiles et al. |
| 3,894,174 | A | 7/1975 | Cartun |
| 3,940,844 | A | 3/1976 | Colby et al. |

(Continued)

FOREIGN PATENT DOCUMENTS

| | | | |
|---|---|---|---|
| CA | 2458946 | A1 | 3/2003 |

(Continued)

OTHER PUBLICATIONS

Office Action issued on Oct. 17, 2006 in U.S. Appl. No. 11/216,562.

(Continued)

*Primary Examiner*—Rinaldi Rada
*Assistant Examiner*—Nathaniel Chukwurah

(57) ABSTRACT

A surgical stapling device. Stapling device may comprise an end effector and a plurality of stacked actuatable wedge band sets. Each stacked wedge band set comprises at least two different-level wedge bands for axially traversing the end effector. Each wedge band comprises a wedge cam at its distal end for driving certain ones of the staple drivers when the wedge band is actuated. A first of the two wedge bands in the stacks rides on a second of the two wedge bands in the stacks such that the staple drivers are driven in successive stages by the at least two wedge bands when the wedge bands are driven in succession. The cumulative height of a first of the plurality of stacked wedge band sets is less than a cumulative height of a second of the plurality of stacked wedge band sets.

20 Claims, 74 Drawing Sheets

U.S. PATENT DOCUMENTS

| | | |
|---|---|---|
| 4,317,451 A | 3/1982 | Cerwin et al. |
| 4,321,002 A | 3/1982 | Froehlich |
| 4,331,277 A | 5/1982 | Green |
| 4,379,457 A | 4/1983 | Gravener et al. |
| 4,380,312 A | 4/1983 | Landrus |
| 4,383,634 A | 5/1983 | Green |
| 4,396,139 A | 8/1983 | Hall et al. |
| 4,428,376 A | 1/1984 | Mericle |
| 4,442,964 A | 4/1984 | Becht |
| 4,485,816 A | 12/1984 | Krumme |
| 4,500,024 A | 2/1985 | DiGiovanni et al. |
| 4,520,817 A | 6/1985 | Green |
| 4,522,327 A | 6/1985 | Korthoff et al. |
| 4,526,174 A | 7/1985 | Froehlich |
| 4,530,453 A | 7/1985 | Green |
| 4,548,202 A | 10/1985 | Duncan |
| 4,566,620 A | 1/1986 | Green et al. |
| 4,573,622 A | 3/1986 | Green et al. |
| 4,580,712 A | 4/1986 | Green |
| 4,589,416 A | 5/1986 | Green |
| 4,605,001 A | 8/1986 | Rothfuss et al. |
| 4,606,343 A | 8/1986 | Conta et al. |
| 4,610,250 A | 9/1986 | Green |
| 4,610,383 A | 9/1986 | Rothfuss et al. |
| 4,629,107 A | 12/1986 | Fedotov et al. |
| 4,633,874 A | 1/1987 | Chow et al. |
| 4,667,674 A | 5/1987 | Korthoff et al. |
| 4,671,445 A | 6/1987 | Barker et al. |
| 4,709,120 A | 11/1987 | Pearson |
| 4,719,917 A | 1/1988 | Barrows et al. |
| 4,728,020 A | 3/1988 | Green et al. |
| 4,741,336 A | 5/1988 | Failla et al. |
| 4,754,909 A | 7/1988 | Barker et al. |
| 4,767,044 A | 8/1988 | Green |
| 4,805,617 A | 2/1989 | Bedi et al. |
| 4,821,939 A | 4/1989 | Green |
| 4,869,414 A | 9/1989 | Green et al. |
| 4,892,244 A | 1/1990 | Fox et al. |
| 4,915,100 A | 4/1990 | Green |
| 4,944,443 A | 7/1990 | Oddsen et al. |
| 4,955,959 A | 9/1990 | Tompkins et al. |
| 5,009,661 A | 4/1991 | Michelson |
| 5,031,814 A | 7/1991 | Tompkins et al. |
| 5,040,715 A | 8/1991 | Green et al. |
| 5,062,563 A | 11/1991 | Green et al. |
| 5,071,430 A | 12/1991 | de Salis et al. |
| 5,080,556 A | 1/1992 | Carreno |
| 5,104,025 A | 4/1992 | Main et al. |
| 5,106,008 A | 4/1992 | Tompkins et al. |
| 5,111,987 A | 5/1992 | Moeinzadeh et al. |
| 5,137,198 A | 8/1992 | Nobis et al. |
| 5,156,315 A | 10/1992 | Green et al. |
| 5,158,567 A | 10/1992 | Green |
| 5,211,649 A | 5/1993 | Kohler et al. |
| 5,219,111 A | 6/1993 | Bilotti et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,258,009 A | 11/1993 | Conners |
| 5,271,544 A | 12/1993 | Fox et al. |
| RE34,519 E | 1/1994 | Fox et al. |
| 5,275,323 A | 1/1994 | Schulze et al. |
| 5,282,806 A | 2/1994 | Haber et al. |
| 5,282,829 A | 2/1994 | Hermes |
| 5,304,204 A | 4/1994 | Bregen |
| 5,307,976 A | 5/1994 | Olson et al. |
| 5,309,927 A | 5/1994 | Welch |
| 5,318,221 A | 6/1994 | Green et al. |
| 5,342,395 A | 8/1994 | Jarrett et al. |
| 5,342,396 A | 8/1994 | Cook |
| 5,344,060 A | 9/1994 | Gravener et al. |
| 5,350,400 A | 9/1994 | Esposito et al. |
| 5,366,134 A | 11/1994 | Green et al. |
| 5,366,479 A | 11/1994 | McGarry et al. |
| 5,379,933 A | 1/1995 | Green et al. |
| 5,383,880 A | 1/1995 | Hooven |
| 5,389,098 A | 2/1995 | Tsuruta et al. |
| 5,395,033 A | 3/1995 | Byrne et al. |
| 5,397,046 A | 3/1995 | Savage et al. |
| 5,397,324 A | 3/1995 | Carroll et al. |
| 5,403,312 A | 4/1995 | Yates et al. |
| 5,413,267 A | 5/1995 | Solyntjes et al. |
| 5,413,268 A | 5/1995 | Green et al. |
| 5,415,335 A | 5/1995 | Knodell, Jr. |
| 5,425,745 A | 6/1995 | Green et al. |
| 5,431,322 A | 7/1995 | Green et al. |
| 5,433,721 A | 7/1995 | Hooven et al. |
| 5,441,193 A | 8/1995 | Gravener |
| 5,445,304 A | 8/1995 | Plyley et al. |
| 5,462,215 A | 10/1995 | Viola et al. |
| 5,465,896 A | 11/1995 | Allen et al. |
| 5,470,006 A | 11/1995 | Rodak |
| 5,472,132 A | 12/1995 | Savage et al. |
| 5,474,566 A | 12/1995 | Alesi et al. |
| 5,480,089 A | 1/1996 | Blewett |
| 5,484,451 A | 1/1996 | Akopov et al. |
| 5,489,058 A | 2/1996 | Plyley et al. |
| 5,503,635 A | 4/1996 | Sauer et al. |
| 5,518,163 A | 5/1996 | Hooven |
| 5,518,164 A | 5/1996 | Hooven |
| 5,522,817 A | 6/1996 | Sander et al. |
| 5,535,935 A | 7/1996 | Vidal et al. |
| 5,535,937 A | 7/1996 | Boiarski et al. |
| 5,540,375 A | 7/1996 | Bolanos et al. |
| 5,547,117 A | 8/1996 | Hamblin et al. |
| 5,554,169 A | 9/1996 | Green et al. |
| 5,560,532 A | 10/1996 | DeFonzo et al. |
| 5,562,682 A | 10/1996 | Oberlin et al. |
| 5,564,615 A | 10/1996 | Bishop et al. |
| 5,571,090 A | 11/1996 | Sherts |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,580,067 A | 12/1996 | Hamblin et al. |
| 5,588,579 A | 12/1996 | Schnut et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,609,285 A | 3/1997 | Grant et al. |
| 5,624,452 A | 4/1997 | Yates |
| 5,630,539 A | 5/1997 | Plyley et al. |
| 5,634,584 A | 6/1997 | Okorocha et al. |
| 5,636,780 A | 6/1997 | Green et al. |
| 5,639,008 A | 6/1997 | Gallagher et al. |
| 5,645,209 A | 7/1997 | Green et al. |
| 5,647,526 A | 7/1997 | Green et al. |
| 5,649,937 A | 7/1997 | Bito et al. |
| 5,653,373 A | 8/1997 | Green et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A * | 9/1997 | Knodel et al. ............ 227/175.1 |
| 5,662,260 A | 9/1997 | Yoon |
| 5,662,662 A | 9/1997 | Bishop et al. |
| 5,667,517 A | 9/1997 | Hooven |

| | | | | | | |
|---|---|---|---|---|---|---|
| 5,667,527 | A | 9/1997 | Cook | 6,616,686 B2 | 9/2003 | Coleman et al. |
| 5,669,544 | A | 9/1997 | Schulze et al. | 6,629,988 B2 | 10/2003 | Weadock |
| 5,673,841 | A | 10/1997 | Schulze et al. | 6,656,193 B2 | 12/2003 | Grant et al. |
| 5,673,842 | A | 10/1997 | Bittner et al. | 6,698,643 B2 | 3/2004 | Whitman |
| 5,678,748 | A | 10/1997 | Plyley et al. | 6,716,233 B1 | 4/2004 | Whitman |
| 5,680,983 | A | 10/1997 | Plyley et al. | 6,767,356 B2 | 7/2004 | Kanner et al. |
| 5,685,474 | A | 11/1997 | Seeber | 6,773,438 B1 | 8/2004 | Knodel et al. |
| 5,690,269 | A | 11/1997 | Bolanos et al. | 6,793,652 B1 | 9/2004 | Whitman et al. |
| 5,697,943 | A | 12/1997 | Sauer et al. | 6,817,508 B1 | 11/2004 | Racenet et al. |
| 5,702,408 | A | 12/1997 | Wales et al. | 6,846,307 B2 | 1/2005 | Whitman et al. |
| 5,706,997 | A | 1/1998 | Green et al. | 6,846,308 B2 | 1/2005 | Whitman et al. |
| 5,709,680 | A | 1/1998 | Yates et al. | 6,846,309 B2 | 1/2005 | Whitman et al. |
| 5,711,472 | A | 1/1998 | Bryan | 6,849,071 B2 | 2/2005 | Whitman et al. |
| 5,713,505 | A | 2/1998 | Huitema | 6,913,608 B2 | 7/2005 | Liddicoat et al. |
| 5,715,988 | A | 2/1998 | Palmer | 6,939,358 B2 | 9/2005 | Palacios et al. |
| 5,716,366 | A | 2/1998 | Yates | 6,945,444 B2 | 9/2005 | Gresham et al. |
| 5,725,536 | A | 3/1998 | Oberlin et al. | 6,959,852 B2 | 11/2005 | Shelton, IV et al. |
| 5,732,871 | A | 3/1998 | Clark et al. | 6,978,922 B2 | 12/2005 | Bilotti et al. |
| 5,735,445 | A | 4/1998 | Vidal et al. | 6,981,941 B2 | 1/2006 | Whitman et al. |
| 5,738,474 | A | 4/1998 | Blewett | 6,988,650 B2 | 1/2006 | Schwemberger et al. |
| 5,743,456 | A | 4/1998 | Jones et al. | 7,000,819 B2 | 2/2006 | Swayze et al. |
| 5,752,965 | A | 5/1998 | Francis et al. | 7,008,435 B2 | 3/2006 | Cummins |
| 5,758,814 | A | 6/1998 | Gallagher et al. | 7,032,799 B2 | 4/2006 | Viola et al. |
| 5,779,132 | A | 7/1998 | Knodel et al. | 7,055,730 B2 | 6/2006 | Ehrenfels et al. |
| 5,782,396 | A | 7/1998 | Mastri et al. | 7,056,330 B2 | 6/2006 | Gayton |
| 5,785,232 | A | 7/1998 | Vidal et al. | 7,059,508 B2 | 6/2006 | Shelton, IV et al. |
| 5,794,834 | A | 8/1998 | Hamblin et al. | 7,063,712 B2 | 6/2006 | Vargas et al. |
| 5,797,536 | A | 8/1998 | Smith et al. | 7,066,944 B2 | 6/2006 | Laufer et al. |
| 5,799,857 | A | 9/1998 | Robertson et al. | 7,070,083 B2 | 7/2006 | Jankowski |
| 5,820,009 | A | 10/1998 | Melling et al. | 7,077,856 B2 | 7/2006 | Whitman |
| 5,823,066 | A | 10/1998 | Huitema et al. | 7,090,684 B2 | 8/2006 | McGuckin, Jr. et al. |
| 5,829,662 | A | 11/1998 | Allen et al. | 7,108,709 B2 | 9/2006 | Cummins |
| 5,833,690 | A | 11/1998 | Yates et al. | 7,118,582 B1 | 10/2006 | Wang et al. |
| 5,836,503 | A | 11/1998 | Ehrenfels et al. | 7,128,253 B2 | 10/2006 | Mastri et al. |
| 5,846,254 | A | 12/1998 | Schulze et al. | 7,128,254 B2 | 10/2006 | Shelton, IV et al. |
| 5,855,311 | A | 1/1999 | Hamblin et al. | 7,140,528 B2 | 11/2006 | Shelton, IV |
| 5,878,937 | A | 3/1999 | Green et al. | 7,143,925 B2 | 12/2006 | Shelton, IV et al. |
| 5,878,938 | A | 3/1999 | Bittner et al. | 7,143,926 B2 | 12/2006 | Shelton, IV et al. |
| 5,891,160 | A | 4/1999 | Williamson, IV et al. | 7,159,750 B2 | 1/2007 | Racenet et al. |
| 5,893,506 | A | 4/1999 | Powell | 7,168,604 B2 | 1/2007 | Milliman et al. |
| 5,897,562 | A | 4/1999 | Bolanos et al. | 7,207,471 B2 | 4/2007 | Heinrich et al. |
| 5,901,895 | A | 5/1999 | Heaton et al. | 7,207,472 B2 | 4/2007 | Wukusick et al. |
| 5,906,625 | A | 5/1999 | Bito et al. | 7,210,609 B2 | 5/2007 | Leiboff et al. |
| 5,915,616 | A | 6/1999 | Viola et al. | 7,220,272 B2 | 5/2007 | Weadock |
| 5,918,791 | A | 7/1999 | Sorrentino et al. | 7,246,734 B2 | 7/2007 | Shelton, IV |
| 5,941,442 | A | 8/1999 | Geiste et al. | 7,258,262 B2 | 8/2007 | Mastri et al. |
| 5,988,479 | A | 11/1999 | Palmer | 7,303,108 B2 | 12/2007 | Shelton, IV |
| 6,017,356 | A | 1/2000 | Frederick et al. | 2002/0117534 A1 | 8/2002 | Green et al. |
| 6,022,352 | A | 2/2000 | Vandewalle | 2002/0165541 A1 | 11/2002 | Whitman |
| 6,024,748 | A | 2/2000 | Manzo et al. | 2003/0220660 A1 | 11/2003 | Kortenbach et al. |
| 6,083,234 | A | 7/2000 | Nicholas et al. | 2004/0002726 A1 | 1/2004 | Nunez et al. |
| 6,083,242 | A | 7/2000 | Cook | 2004/0006372 A1 | 1/2004 | Racenet et al. |
| 6,086,600 | A | 7/2000 | Kortenbach | 2004/0034357 A1 | 2/2004 | Beane et al. |
| 6,099,537 | A | 8/2000 | Sugai et al. | 2004/0044364 A1 | 3/2004 | DeVries et al. |
| 6,131,789 | A | 10/2000 | Schulze et al. | 2004/0097987 A1 | 5/2004 | Pugsley et al. |
| 6,171,316 | B1 | 1/2001 | Kovac et al. | 2004/0101822 A1 | 5/2004 | Weisner et al. |
| 6,171,330 | B1 | 1/2001 | Benchetrit | 2004/0108357 A1 | 6/2004 | Milliman et al. |
| 6,264,086 | B1 | 7/2001 | McGuckin, Jr. | 2004/0111081 A1 | 6/2004 | Whitman et al. |
| 6,273,897 | B1 | 8/2001 | Dalessandro et al. | 2004/0122471 A1 | 6/2004 | Toby et al. |
| 6,320,123 | B1 | 11/2001 | Reimers | 2004/0164123 A1 | 8/2004 | Racenet et al. |
| 6,325,810 | B1 | 12/2001 | Hamilton et al. | 2004/0167572 A1 | 8/2004 | Roth et al. |
| 6,358,224 | B1 | 3/2002 | Tims et al. | 2004/0173659 A1 | 9/2004 | Green et al. |
| 6,387,113 | B1 | 5/2002 | Hawkins et al. | 2004/0232201 A1 | 11/2004 | Wenchell et al. |
| 6,387,114 | B2 | 5/2002 | Adams | 2004/0243151 A1 | 12/2004 | Demmy et al. |
| 6,398,797 | B2 | 6/2002 | Bombard et al. | 2004/0243176 A1 | 12/2004 | Hahnen et al. |
| 6,416,486 | B1 | 7/2002 | Wampler | 2004/0254608 A1 | 12/2004 | Huitema et al. |
| RE37,814 | E | 8/2002 | Allgeyer | 2005/0070958 A1 | 3/2005 | Swayze et al. |
| 6,440,146 | B2 | 8/2002 | Nicholas et al. | 2005/0080454 A1 | 4/2005 | Drews et al. |
| 6,443,973 | B1 | 9/2002 | Whitman | 2005/0107824 A1 | 5/2005 | Hillstead et al. |
| 6,503,257 | B2 | 1/2003 | Grant et al. | 2005/0119669 A1 | 6/2005 | Demmy |
| 6,505,768 | B2 | 1/2003 | Whitman | 2005/0125009 A1 | 6/2005 | Perry et al. |
| 6,522,101 | B2 | 2/2003 | Malackowski | 2005/0131390 A1 | 6/2005 | Heinrich et al. |
| 6,592,597 | B2 | 7/2003 | Grant et al. | 2005/0143759 A1 | 6/2005 | Kelly |

| | | |
|---|---|---|
| 2005/0145671 A1 | 7/2005 | Viola |
| 2005/0169974 A1 | 8/2005 | Tenerz et al. |
| 2005/0187576 A1 | 8/2005 | Whitman et al. |
| 2005/0203550 A1 | 9/2005 | Laufer et al. |
| 2005/0216055 A1 | 9/2005 | Scirica et al. |
| 2005/0263563 A1 | 12/2005 | Racenet et al. |
| 2006/0025813 A1 | 2/2006 | Shelton et al. |
| 2006/0047308 A1 | 3/2006 | Ortiz et al. |
| 2006/0052825 A1 | 3/2006 | Ransick et al. |
| 2006/0060630 A1 | 3/2006 | Shelton, IV et al. |
| 2006/0085033 A1 | 4/2006 | Criscuolo et al. |
| 2006/0100643 A1 | 5/2006 | Laufer et al. |
| 2006/0108393 A1 | 5/2006 | Heinrich et al. |
| 2006/0122636 A1 | 6/2006 | Bailly et al. |
| 2006/0142772 A1 | 6/2006 | Ralph et al. |
| 2006/0173470 A1 | 8/2006 | Oray et al. |
| 2006/0183246 A1 | 8/2006 | Wiesner et al. |
| 2006/0190028 A1 | 8/2006 | Wales et al. |
| 2006/0226196 A1 | 10/2006 | Hueil et al. |
| 2006/0245971 A1 | 11/2006 | Burns et al. |
| 2006/0289602 A1 | 12/2006 | Wales et al. |
| 2006/0291981 A1 | 12/2006 | Viola et al. |
| 2007/0034666 A1* | 2/2007 | Holsten et al. ............ 227/176.1 |
| 2007/0073340 A1 | 3/2007 | Shelton, IV et al. |
| 2007/0083234 A1 | 4/2007 | Shelton, IV et al. |
| 2007/0084897 A1 | 4/2007 | Shelton, IV et al. |
| 2007/0102452 A1 | 5/2007 | Shelton, IV et al. |
| 2007/0102453 A1 | 5/2007 | Morgan et al. |
| 2007/0106317 A1 | 5/2007 | Shelton, IV et al. |
| 2007/0114261 A1 | 5/2007 | Ortiz et al. |
| 2007/0131732 A1* | 6/2007 | Holsten et al. ............ 227/179.1 |
| 2007/0179476 A1 | 8/2007 | Shelton, IV et al. |
| 2007/0181632 A1 | 8/2007 | Milliman |
| 2007/0213750 A1 | 9/2007 | Weadock |
| 2007/0233053 A1 | 10/2007 | Shelton, IV et al. |
| 2007/0295780 A1 | 12/2007 | Shelton et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0035701 A1 | 2/2008 | Racenet et al. |
| 2008/0041917 A1 | 2/2008 | Racenet et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |
| 2008/0164296 A1 | 7/2008 | Shelton et al. |
| 2008/0167522 A1 | 7/2008 | Giordano et al. |
| 2008/0167644 A1 | 7/2008 | Shelton et al. |
| 2008/0167670 A1 | 7/2008 | Shelton et al. |
| 2008/0167671 A1 | 7/2008 | Giordano et al. |
| 2008/0167672 A1 | 7/2008 | Giordano et al. |
| 2008/0167736 A1 | 7/2008 | Swayze et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |

FOREIGN PATENT DOCUMENTS

| | | |
|---|---|---|
| DE | 273689 C | 5/1914 |
| DE | 20112837 U1 | 10/2001 |
| DE | 20121753 U1 | 4/2003 |
| EP | 0600182 A2 | 6/1994 |
| EP | 0646357 A1 | 4/1995 |
| EP | 0669104 A1 | 8/1995 |
| EP | 0702937 A1 | 3/1996 |
| EP | 0541987 B1 | 7/1996 |
| EP | 0770355 A1 | 5/1997 |
| EP | 0625335 B1 | 11/1997 |
| EP | 0648476 B1 | 1/1998 |
| EP | 0878169 A1 | 11/1998 |
| EP | 0537572 B1 | 6/1999 |
| EP | 0908152 B1 | 1/2002 |
| EP | 1479345 A1 | 11/2004 |
| EP | 1479347 A1 | 11/2004 |
| EP | 1479348 A1 | 11/2004 |
| EP | 1520523 A1 | 4/2005 |
| EP | 1520525 A1 | 4/2005 |
| EP | 1522264 A1 | 4/2005 |
| EP | 1550408 A1 | 7/2005 |
| EP | 1557129 A1 | 7/2005 |
| EP | 1621141 A2 | 2/2006 |
| EP | 1652481 A2 | 5/2006 |
| EP | 1617768 B1 | 8/2006 |
| EP | 1702567 A2 | 9/2006 |
| EP | 1728473 A1 | 12/2006 |
| EP | 1728475 A2 | 12/2006 |
| EP | 1300117 B1 | 8/2007 |
| FR | 1112936 A | 3/1956 |
| GB | 939929 A | 10/1963 |
| GB | 2336214 A | 10/1999 |
| JP | 6007357 A | 1/1994 |
| JP | 7051273 A | 2/1995 |
| JP | 8033641 A | 2/1996 |
| JP | 8229050 A | 9/1996 |
| JP | 2001286477 A | 10/2001 |
| JP | 2002369820 A | 12/2002 |
| JP | 2005505322 T | 2/2005 |
| JP | 2005103293 A | 4/2005 |
| RU | 2187249 C2 | 8/2002 |
| RU | 2225170 C2 | 3/2004 |
| SU | 1377053 A1 | 2/1988 |
| SU | 1561964 A1 | 5/1990 |
| SU | 1722476 A1 | 3/1992 |
| WO | WO 93/08755 A1 | 5/1993 |
| WO | WO 95/18572 A1 | 7/1995 |
| WO | WO 95/29639 A1 | 11/1995 |
| WO | WO 96/35464 A1 | 11/1996 |
| WO | WO 98/30153 A1 | 7/1998 |
| WO | WO 99/12483 A1 | 3/1999 |
| WO | WO 99/15086 A1 | 4/1999 |
| WO | WO 99/34744 A1 | 7/1999 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/05702 A1 | 1/2001 |
| WO | WO 01/10482 A1 | 2/2001 |
| WO | WO 01/62158 A2 | 8/2001 |
| WO | WO 01/62162 A1 | 8/2001 |
| WO | WO 01/62164 A2 | 8/2001 |
| WO | WO 01/91646 A1 | 12/2001 |
| WO | WO 02/17799 A1 | 3/2002 |
| WO | WO 02/19920 A1 | 3/2002 |
| WO | WO 02/30297 A2 | 4/2002 |
| WO | WO 02/32322 A1 | 4/2002 |
| WO | WO 02/43571 A2 | 6/2002 |
| WO | WO 02/067785 A2 | 9/2002 |

| | | | |
|---|---|---|---|
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/020106 A2 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/101313 A1 | 12/2003 |
| WO | WO 03/105702 A2 | 12/2003 |
| WO | WO 2004/006980 A2 | 1/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/047653 A2 | 6/2004 |
| WO | WO 2004/049956 A2 | 6/2004 |
| WO | WO 2004/086987 A1 | 10/2004 |
| WO | WO 2004/096057 A2 | 11/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/096954 A2 | 10/2005 |
| WO | WO 2005/115251 A2 | 12/2005 |
| WO | WO 2006/044490 A2 | 4/2006 |
| WO | WO 2006/044581 A2 | 4/2006 |
| WO | WO 2006/044810 A2 | 4/2006 |
| WO | WO 2006/083748 A1 | 8/2006 |
| WO | WO 2006/132992 A1 | 12/2006 |
| WO | WO 2007/016290 A2 | 2/2007 |

OTHER PUBLICATIONS

Office Action issued on Mar. 14, 2007 in U.S. Appl. No. 11/216,562.
Office Action issued on Jun. 21, 2007 in U.S. Appl. No. 11/216,562.
Disclosed Anonymously, "Motor-Driven Surgical Stapler Improvements," Research Disclosure Database No. 526041, Published: Feb. 2008.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
U.S. Appl. No. 11/824,251, filed Jun. 29, 2007.
U.S. Appl. No. 12/038,939, filed Feb. 28, 2008.
U.S. Appl. No. 11/824,446, filed Jun. 29, 2007.
U.S. Appl. No. 11/824,389, filed Jun. 29, 2007.
U.S. Appl. No. 11/824,415, filed Jun. 29, 2007.
U.S. Appl. No. 11/824,274, filed Jun. 29, 2007.
U.S. Appl. No. 11/824,275, filed Jun. 29, 2007.
U.S. Appl. No. 11/823,988, filed Jun. 29, 2007.
U.S. Appl. No. 11/824,079, filed Jun. 29, 2007.
U.S. Appl. No. 11/824,524, filed Jun. 29, 2007.
U.S. Appl. No. 11/824,298, filed Jun. 29, 2007.
U.S. Appl. No. 11/824,252, filed Jun. 29, 2007.

* cited by examiner

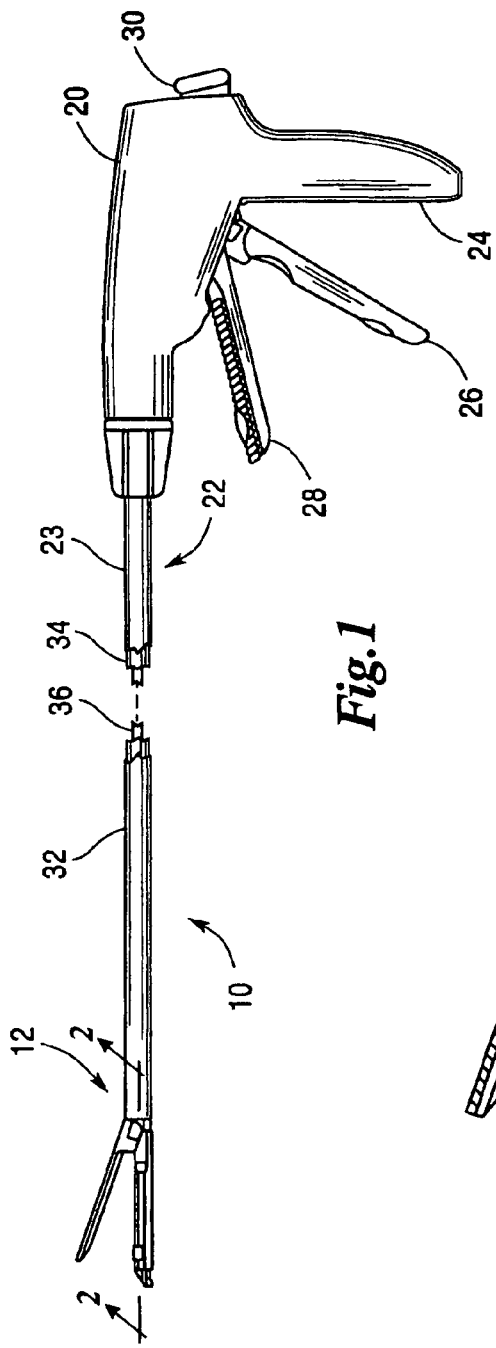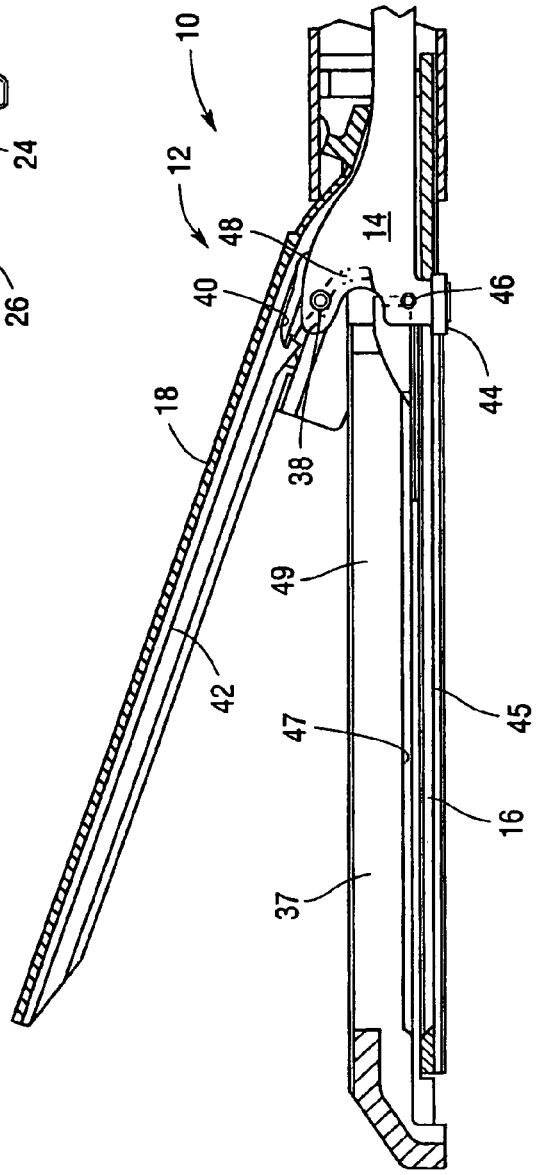

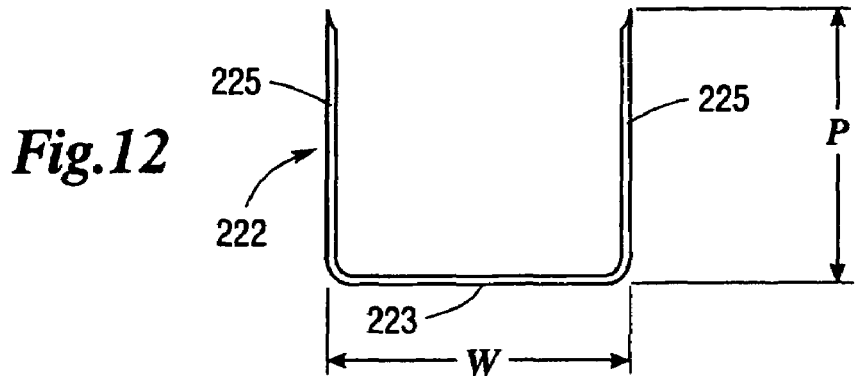
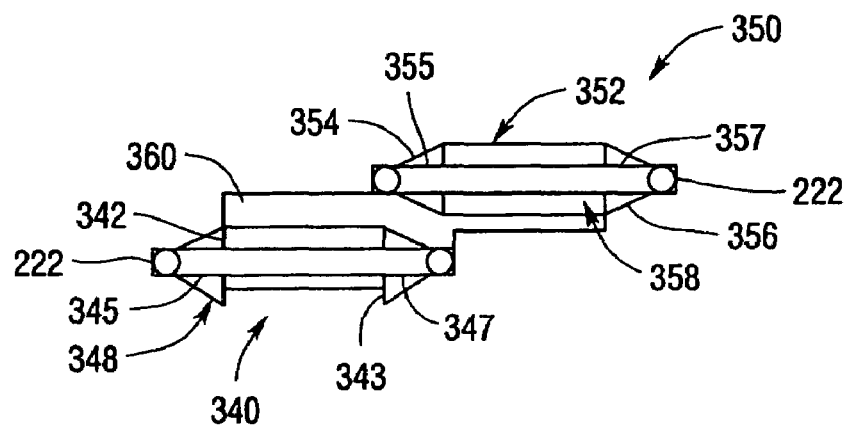
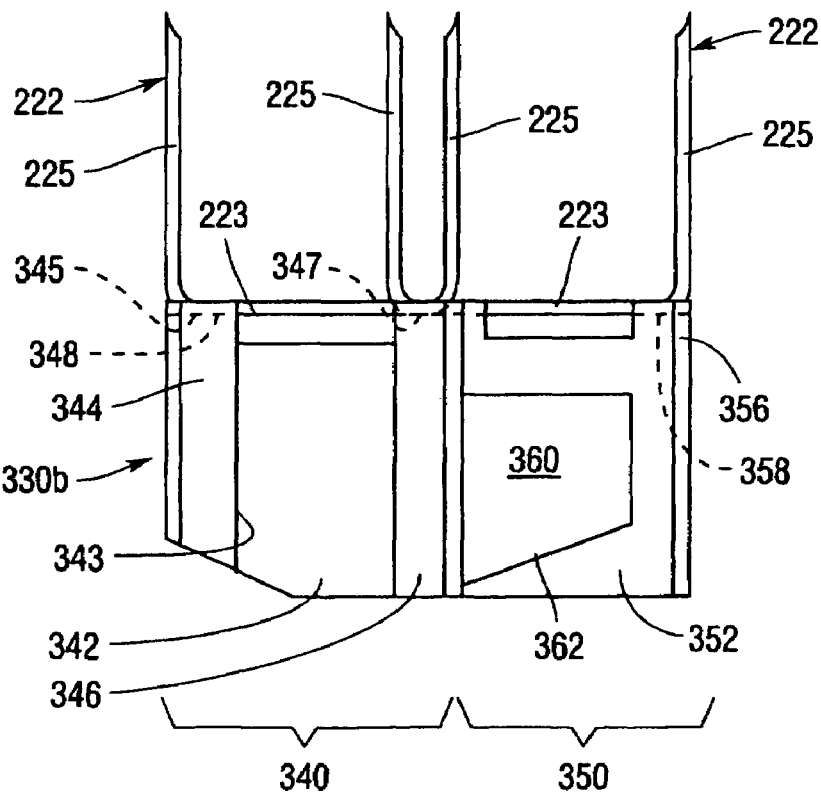

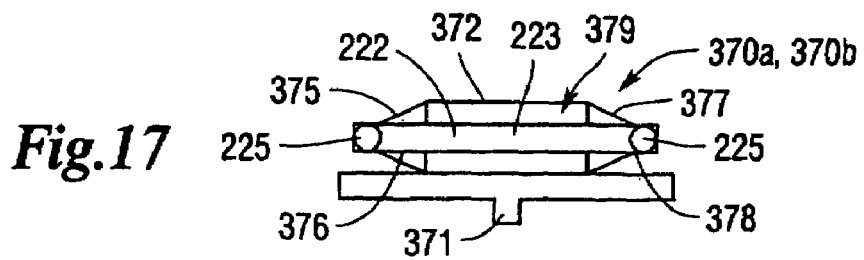
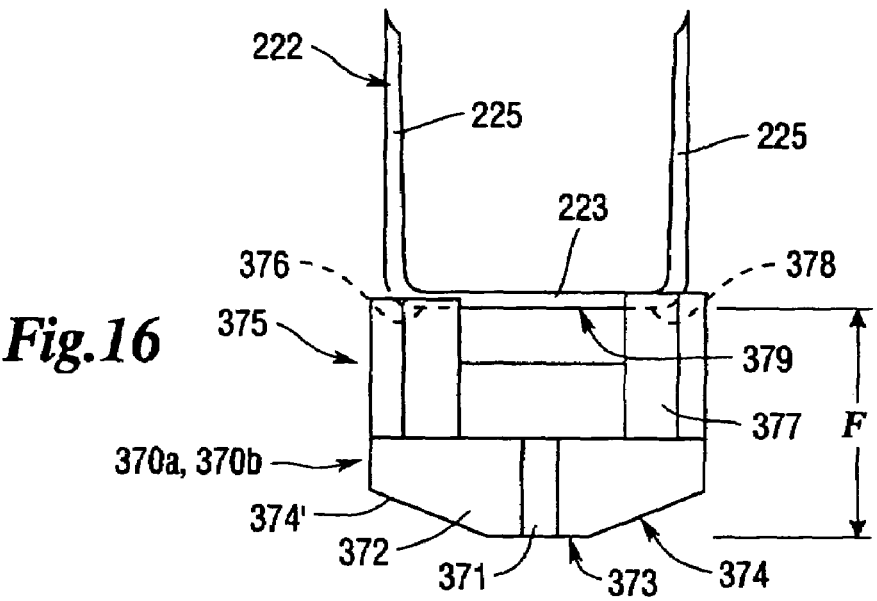
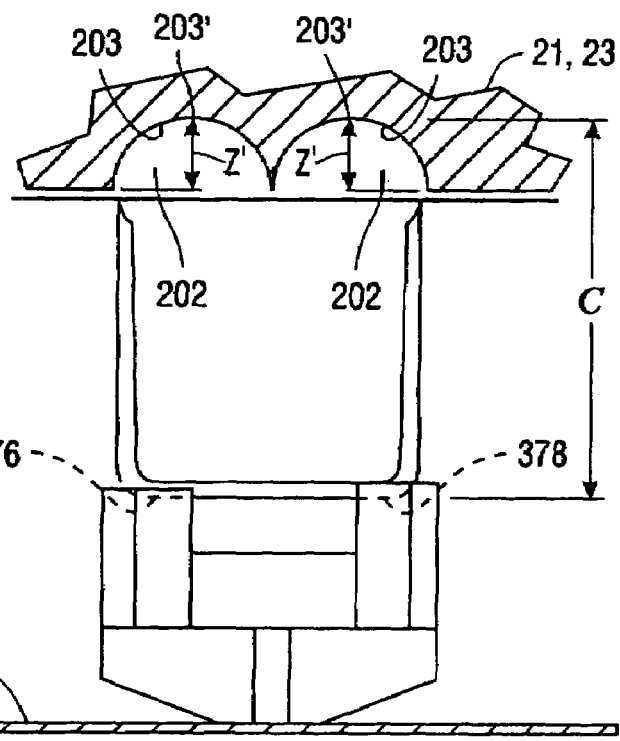

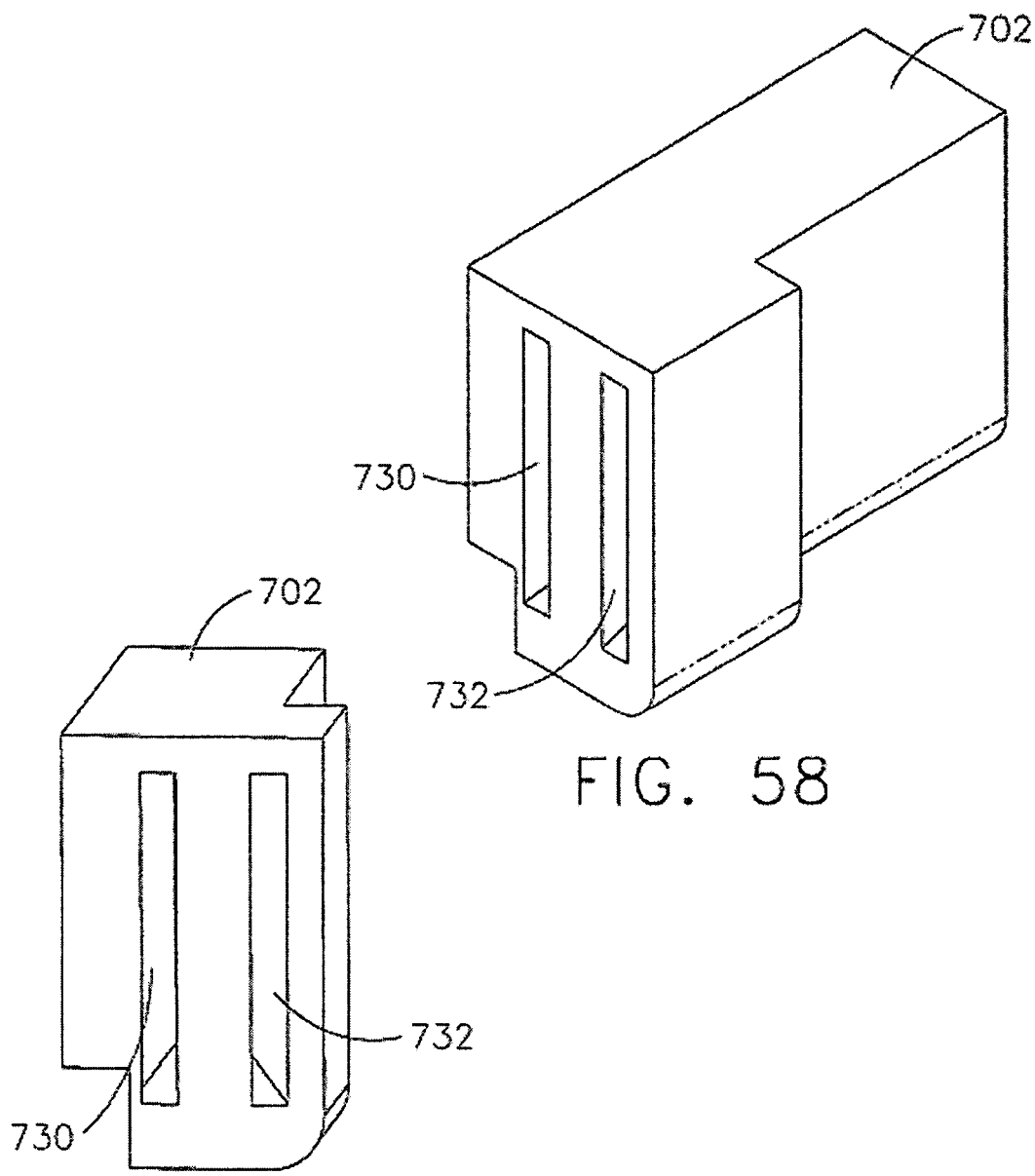
FIG. 58
FIG. 59
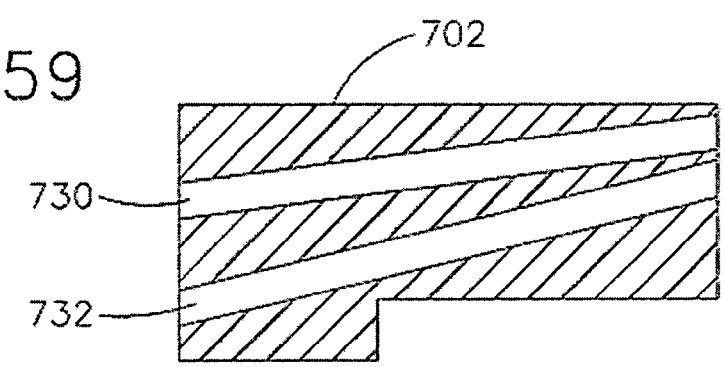
FIG. 60

SURGICAL STAPLING DEVICE WITH MULTIPLE STACKED ACTUATOR WEDGE CAMS FOR DRIVING STAPLE DRIVERS

CROSS-REFERENCE TO RELATED APPLICATIONS

The present application is a continuation-in-part under 35 U.S.C. §120 of U.S. patent application Ser. No. 11/216,562, filed Aug. 31, 2005, entitled "Staple Cartridges For Forming Staples Having Differing Formed Staple Heights," by F. Shelton, which is incorporated herein by reference.

The present application is also related to the following, concurrently-filed U.S. patent applications, which are incorporated herein by reference:
(1) "Surgical Stapling Devices That Produce Formed Staples Having Different Lengths," by J. Hueil et al., U.S. application Ser. No. 11/711,979;
(2) "Surgical Stapling Device With Staple Driver That Supports Multiple Wire Diameter Staples," by J. Swayze et al., U.S. application Ser. No. 11/711,977;
(3) "Surgical Stapling Device With Anvil Having Staple Forming Pockets Of Varying Depth," by J. Morgan et al., U.S. application Ser. No. 11/714,049; and
(4) "Surgical Stapling Device With Staple Drivers Of Different Height," by J. Hueil et al., U.S. application Ser. No. 11/711,975.

FIELD OF THE INVENTION

The present invention relates in general to stapling instruments that are capable of applying lines of staples and, more particularly, to improvements relating to staple cartridges for use with surgical stapling instruments that are capable of applying lines of staples having differing formed staple heights to tissue while simultaneously cutting the tissue.

BACKGROUND OF THE INVENTION

Surgical staplers have been used in the prior art to simultaneously make a longitudinal incision in tissue and apply lines of staples on opposing sides of the incision. Such instruments commonly include a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges that, when driven distally, pass through openings in the staple cartridge and engage drivers supporting the staples to effect the firing of the staples toward the anvil.

An example of a surgical stapler suitable for endoscopic applications is described in U.S. Patent Application No. US 2004/0232196 A1, the disclosure of which is herein incorporated by reference in its entirety. In use, a clinician is able to close the jaw members of the stapler upon tissue to position the tissue prior to firing. Once the clinician has determined that the jaw members are properly gripping tissue, the clinician can then fire the surgical stapler, thereby severing and stapling the tissue. The simultaneous severing and stapling avoids complications that may arise when performing such actions sequentially with different surgical tools that respectively only sever or staple.

Whenever a transsection of tissue is across an area of varied tissue composition, it would be advantageous for the staples that are closest to the cut line to have one formed height that is less than the formed height of those staples that are farthest from the cut line. In practice, the rows of inside staples serve to provide a hemostatic barrier, while the outside rows of staples with larger formed heights provide a cinching effect where the tissue transitions from the tightly compressed hemostatic section to the non-compressed adjacent section. In other applications, it may be useful for the staples in a single line of staples to have differing formed heights. U.S. Pat. Nos. 4,941,623 and 5,027,834 to Pruitt disclose surgical stapler and cartridge arrangements that employ staples that have different prong lengths to ultimately achieve lines of staples that have differing formed heights. Likewise, WO 2003/094747A1 discloses a surgical stapler and cartridge that has six rows of staples wherein the outer two rows of staples comprise staples that are larger than the staples employed in the inner two rows and middle rows of staples. Thus, all of these approaches require the use of different sizes of staples in the same cartridge.

BRIEF SUMMARY OF THE INVENTION

In one general aspect, the present invention is directed to surgical stapling devices that are capable of producing staples of different formed lengths. For example, in such a device that also cuts the tissue being stapled, the inside rows of staples closest to the longitudinal incision line could have a formed height that is less than the formed height of the outer rows of staples. That way, the inside rows of staples may provide a hemostatic barrier, while the outside rows of staples with larger formed heights may provide a cinching effect where the tissue transitions from the tightly compressed hemostatic section to the non-compressed adjacent section.

According to various implementations, the staple cartridge may have staple drivers of different heights to product staples having different formed lengths. The staples driven by the shorter staple drivers would have longer formed lengths (assuming no other differences that would affect the formed heights of the staples). Also, the staple forming pockets in the anvil may have different depths. Staples formed in deeper pockets would tend to be longer than staples formed in shallow pockets. In addition, some of the staple forming pockets may be formed in compliant material portions of the anvil. Staples formed in such pockets would tend to be longer than staples formed in a non-compliant (or less compliant) portion of the anvil. Additionally, the channel may have internal steps that would produce staples having different formed heights. Staples formed with staple drivers starting at a lower step would have a longer formed length that stapled formed with staple drivers starting at a higher step. Also, staples with different wire diameters may be used. Thicker staples would tend to produce staples with longer formed lengths. In that connection, embodiments of the present invention are directed to staple pushers that can accommodate staples of varying wire thicknesses. Also, staples of differing materials could be used. Staples made of stronger, less compliant materials, would tend to produce longer formed staples.

According to other embodiments, the surgical stapling device may comprise a plurality of stacked wedge band sets. Each stacked wedge band set may comprise a number of wedge bands stacked one on another. The wedge bands may be actuated in succession in order to drive the staples in successive stages. That is, for example, in an embodiment having three wedge bands in a stack, the first wedge band may be actuated first to partially deploy the staples, the second wedge band in stack may be actuated next to begin to form the staples, and the third wedge band in the stack may be actuated last to finish the formation of the staples. To produce staples having different formed heights, the heights of the stacks (corresponding to the cumulative height of the wedge bands in the stacks) may be different, for example.

The techniques used to create formed staples of different heights could be used in a variety of different surgical stapling devices. For example, the stapling devices could be devices that cut the clamped tissue or devices that include no cutting instrument. The surgical staplers may be, for example, endocutters, open linear stapler devices, or circular staplers.

BRIEF DESCRIPTION OF THE FIGURES

The accompanying drawings, which are incorporated in and constitute a part of this specification, illustrate by way of example embodiments of the invention, and, together with the general description of the invention given above, and the detailed description of the embodiments given below, serve to explain the principles of the present invention, wherein:

FIG. 1 depicts a partially cut away side elevation view of a surgical stapling and severing instrument in an open position according to various embodiments of the present invention;

FIG. 2 depicts a cross-sectional side elevation detail view along the line 2-2 of FIG. 1 of an end effector of the surgical stapling and severing instrument according to various embodiments of the present invention;

FIG. 12 is a side view of a staple that may be employed with various embodiments of the present invention;

FIG. 13 is a front elevational view of one inside double driver supporting two staples thereon according to various embodiments of the present invention;

FIG. 14 is a top view of the inside double driver and staples of FIG. 13 according to various embodiments of the present invention;

FIG. 16 is a front elevational view of one outside single driver supporting a staple thereon according to various embodiments of the present invention;

FIG. 16A is another front view of the outside single driver of FIG. 16 with portions of the cartridge tray and anvil shown to illustrate the relationships therebetween according to various embodiments of the present invention;

FIG. 17 is a top view of the outside single driver and staple of FIG. 16 according to various embodiments of the present invention;

FIGS. 51-62 depict aspects of a surgical stapling device having stacks of actuatable wedge bands according to various embodiments of the present invention;

DETAILED DESCRIPTION OF THE INVENTION

Figure 3:
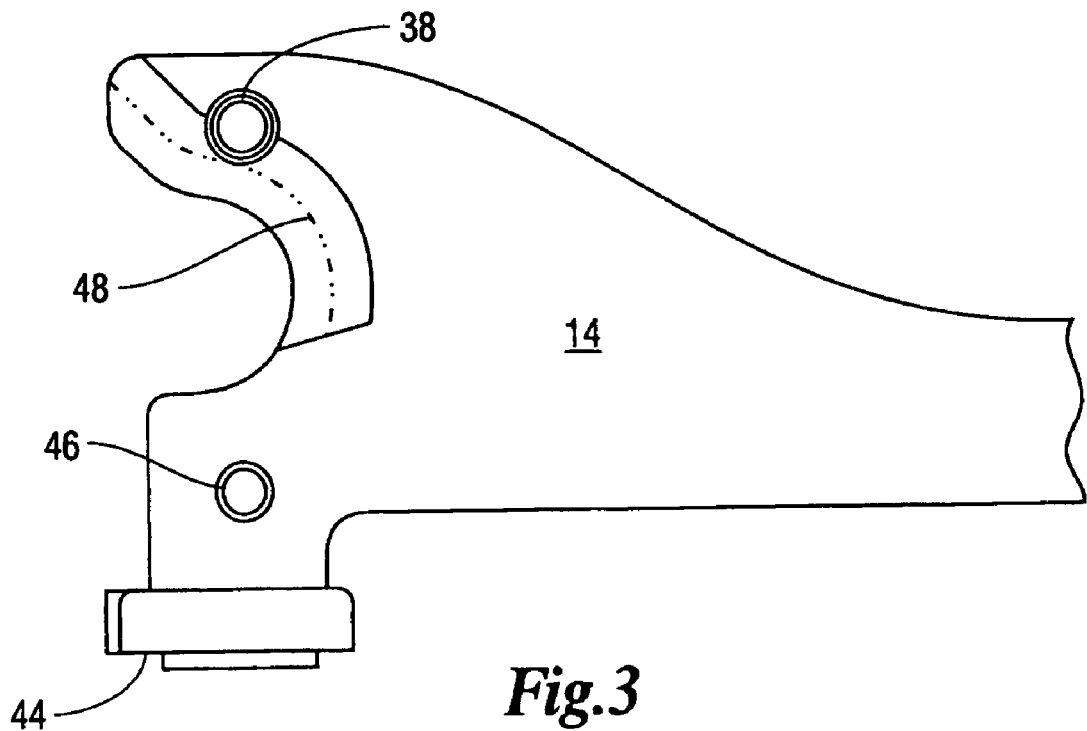
FIG. 3 depicts an enlarged side elevation view of the firing bar of the surgical stapling and severing instrument of FIG. 2 according to various embodiments of the present invention.

Turning to the figures, wherein like numerals denote like components throughout the several views, FIGS. 1 and 2 depict one embodiment of a surgical stapling and severing instrument 10 that is capable of practicing the unique benefits of the present invention. It should be recognized, however, that the unique and novel aspects of the present invention may be advantageously employed in connection with a variety of other staplers and stapler instruments without departing from the spirit and scope of the present invention. Accordingly, the scope of protection afforded to the various embodiments of the present invention should not be limited to use only with the specific type of surgical stapling and severing instruments described herein.

As can be seen in FIGS. 1 and 2, the surgical stapling and severing instrument 10 incorporates an end effector 12 having an actuator or E-beam firing mechanism ("firing bar") 14 that advantageously controls the spacing of the end effector 12. In particular, an elongate channel 16 and a pivotally translatable anvil 18 are maintained at a spacing that assures effective stapling and severing. The problems are avoided associated with varying amounts of tissue being captured in the end effector 12.

It will be appreciated that the terms "proximal" and "distal" are used herein with reference to a clinician gripping a handle of an instrument. Thus, the end effector 12 is distal with respect to the more proximal handle portion 20. It will be further appreciated that for convenience and clarity, spatial terms such as "vertical" and "horizontal" are used herein with respect to the drawings. However, surgical instruments are used in many orientations and positions, and these terms are not intended to be limiting and absolute.

The surgical and stapling and severing instrument 10 includes a handle portion 20 that is connected to an implement portion 22, the latter further comprising a shaft 23 distally terminating in the end effector 12. The handle portion 20 includes a pistol grip 24 toward which a closure trigger 26 is pivotally drawn by the clinician to cause clamping, or closing, of the anvil 18 toward the elongate channel 16 of the end effector 12. A firing trigger 28 is farther outboard of the closure trigger 26 and is pivotally drawn by the clinician to cause the stapling and severing of clamped tissue in the end effector 12.

In practice, closure trigger 26 is actuated first. Once the clinician is satisfied with the positioning of the end effector 12, the clinician may draw back the closure trigger 26 to its fully closed, locked position proximate to the pistol grip 24. Then, the firing trigger 28 is actuated. The firing trigger 28 springedly returns when the clinician removes pressure. A release button 30 when depressed on the proximal end of the handle portion 20 releases any locked closure trigger 26.

A closure sleeve 32 encloses a frame 34, which in turn encloses a firing drive member 36 that is positioned by the firing trigger 28. The frame 34 connects the handle portion 20 to the end effector 12. With the closure sleeve 32 withdrawn proximally by the closure trigger 26 as depicted, the anvil 18 springedly opens, pivoting away from the elongate channel 16 and translating proximally with the closure sleeve 32. The elongate channel 16 receives a staple cartridge 37.

Figure 4:
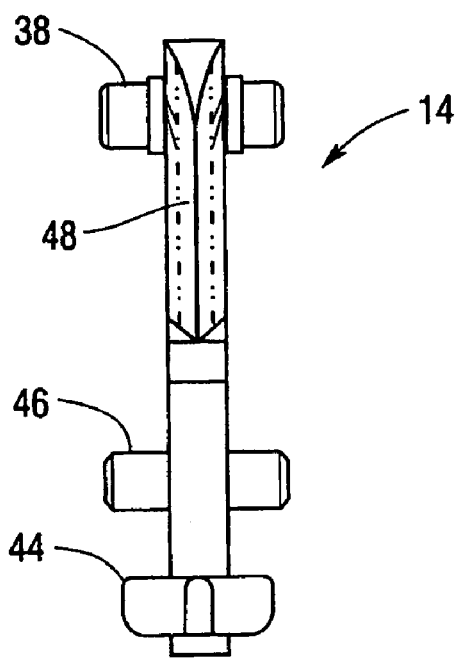
FIG. 4 depicts an enlarged front view of the firing bar of the surgical stapling and severing instrument of FIG. 2 according to various embodiments of the present invention.
Figure 5:
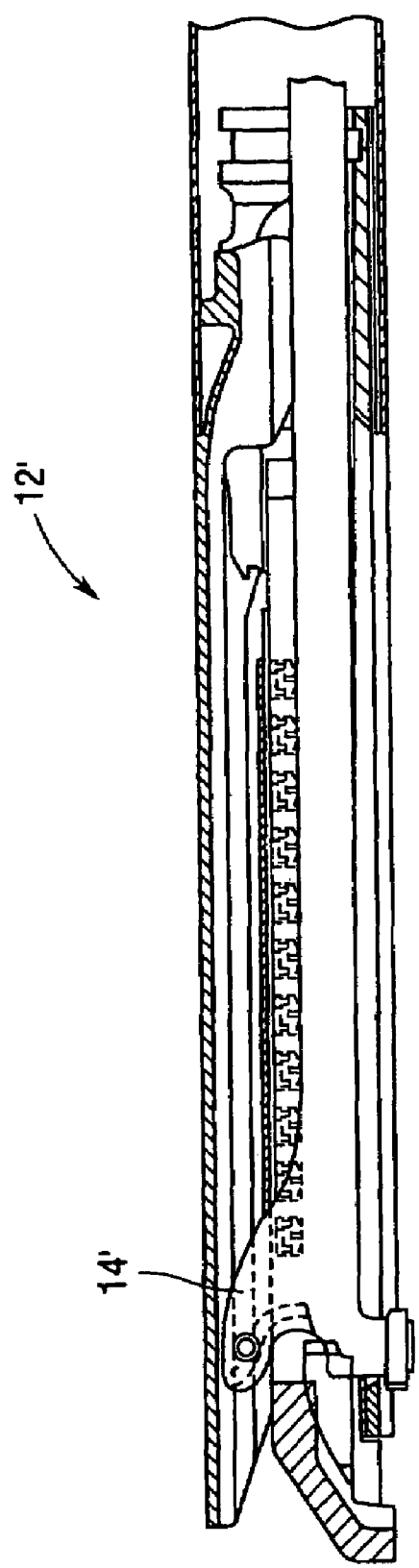
FIG. 5 depicts a cross-sectional side elevation detail view of an alternative end effector for the surgical stapling and severing instrument of FIG. 1, incorporating a firing bar that lacks a middle pin for preventing pinching of the end effector, according to various embodiments of the present invention.

With particular reference to FIGS. 2-4, the firing bar 14 includes three vertically spaced pins that control the spacing of the end effector 12 during firing. In particular, an upper pin 38 is staged to enter an anvil pocket 40 near the pivot between the anvil 18 and elongate channel 16. When fired with the anvil 18 closed, the upper pin 38 advances distally within a longitudinal anvil slot 42 extending distally through anvil 18. Any minor upward deflection in the anvil 18 is overcome by a downward force imparted by the upper pin 38. Firing bar 14 also includes a lowermost pin, or firing bar cap, 44 that upwardly engages a channel slot 45 in the elongate channel 16, thereby cooperating with the upper pin 38 to draw the anvil 18 and the elongate channel 16 slightly closer together in the event of excess tissue clamped therebetween. The firing bar 14 advantageously includes a middle pin 46 that passes through a firing drive slot 47 formed in a lower surface of the cartridge 300 and an upward surface of the elongate channel 16, thereby driving the staples therein as described below. The middle pin 46, by sliding against the elongate channel 16, advantageously resists any tendency for the end effector 12 to be pinched shut at its distal end. To illustrate an advantage of the middle pin 46, FIG. 5 depicts an alternative end effector 12' that lacks a middle pin on a firing bar 14'. In this depiction, the end effector 12' is allowed to pinch shut at its distal end, which tends to impair desired staple formation.

Returning to FIGS. 2-4, a distally presented cutting edge 48 between the upper and middle pins 38, 46 on the firing bar 14 traverses through a proximally presented, vertical slot 49 in the cartridge 37 to sever clamped tissue. The affirmative positioning of the firing bar 14 with regard to the elongate channel 16 and anvil 18 assure that an effective cut is performed. The affirmative vertical spacing provided by the E-Beam firing bar 14 is suitable for the limited size available for endoscopic devices. Moreover, the E-Beam firing bar 14 enables fabrication of an anvil 15 with a camber imparting a vertical deflection at its distal end, similar to the position depicted in FIG. 5. This cambered anvil 15 advantageously assists in achieving the desired gap in the end effector 12 even with an anvil 15 having a reduced thickness, which may be more suited to the size limitations of an endoscopic device.

With reference to FIGS. 6-9, the handle portion 20 is comprised of first and second base sections 50 and 52, which are molded from a polymeric material such as a glass-filled polycarbonate. The first base section 50 is provided with a plurality of cylindrically-shaped pins 54. The second base section 52 includes a plurality of extending members 56, each having a hexagonal-shaped opening 58. The cylindrically-shaped pins 54 are received within the hexagonal-shaped openings 58 and are frictionally held therein for maintaining the first and second base sections 50 and 52 in assembly.

A rotating knob 60 has a bore 62 extending completely through it for engaging and rotating the implement portion 22 about its longitudinal axis. The rotating knob 60 includes an inwardly protruding boss 64 extending along at least a portion of the bore 62. The protruding boss 64 is received within a longitudinal slot 66 formed at a proximal portion of the closure sleeve 32 such that rotation of the rotating knob 60 effects rotation of the closure sleeve 32. It will be appreciated that the boss 64 further extends through frame 34 and into contact with a portion of the firing drive member 36 to effect their rotation as well. Thus, the end effector 12 (not shown in FIGS. 6-9) rotates with the rotating knob 60.

A proximal end 68 of the frame 34 passes proximally through the rotating knob 60 and is provided with a circumferential notch 70 that is engaged by opposing channel securement members 72 extending respectively from the base sections 50 and 52. Only the channel securement member 72 of the second base section 52 is shown. The channel securement members 72, extending from the base sections 50, 52 serve to secure the frame 34 to the handle portion 20 such that the frame 34 does not move longitudinally relative to the handle portion 20.

The closure trigger 26 has a handle section 74, a gear segment section 76, and an intermediate section 78. A bore 80 extends through the intermediate section 78. A cylindrical support member 82 extending from the second base section 52 passes through the bore 80 for pivotably mounting the closure trigger 26 on the handle portion 20. A second cylindrical support member 83 extending from the second base section 52 passes through a bore 81 of firing trigger 28 for pivotally mounting on the handle portion 20. A hexagonal opening 84 is provided in the cylindrical support member 83 for receiving a securement pin (not shown) extending from the first base section 50.

A closure yoke 86 is housed within the handle portion 20 for reciprocating movement therein and serves to transfer motion from the closure trigger 26 to the closure sleeve 32. Support members 88 extending from the second base section 52 and securement member 72, which extends through a recess 89 in the yoke 86, support the yoke 86 within the handle portion 20.

A proximal end 90 of the closure sleeve 32 is provided with a flange 92 that is snap-fitted into a receiving recess 94 formed in a distal end 96 of the yoke 86. A proximal end 98 of the yoke 86 has a gear rack 100 that is engaged by the gear segment section 76 of the closure trigger 26. When the closure trigger 26 is moved toward the pistol grip 24 of the handle portion 20, the yoke 86 and, hence, the closure sleeve 32 move distally, compressing a spring 102 that biases the yoke 86 proximally. Distal movement of the closure sleeve 32 effects pivotal translation movement of the anvil 18 distally and toward the elongate channel 16 of the end effector 12 and proximal movement effects closing, as discussed below.

Figure 8:
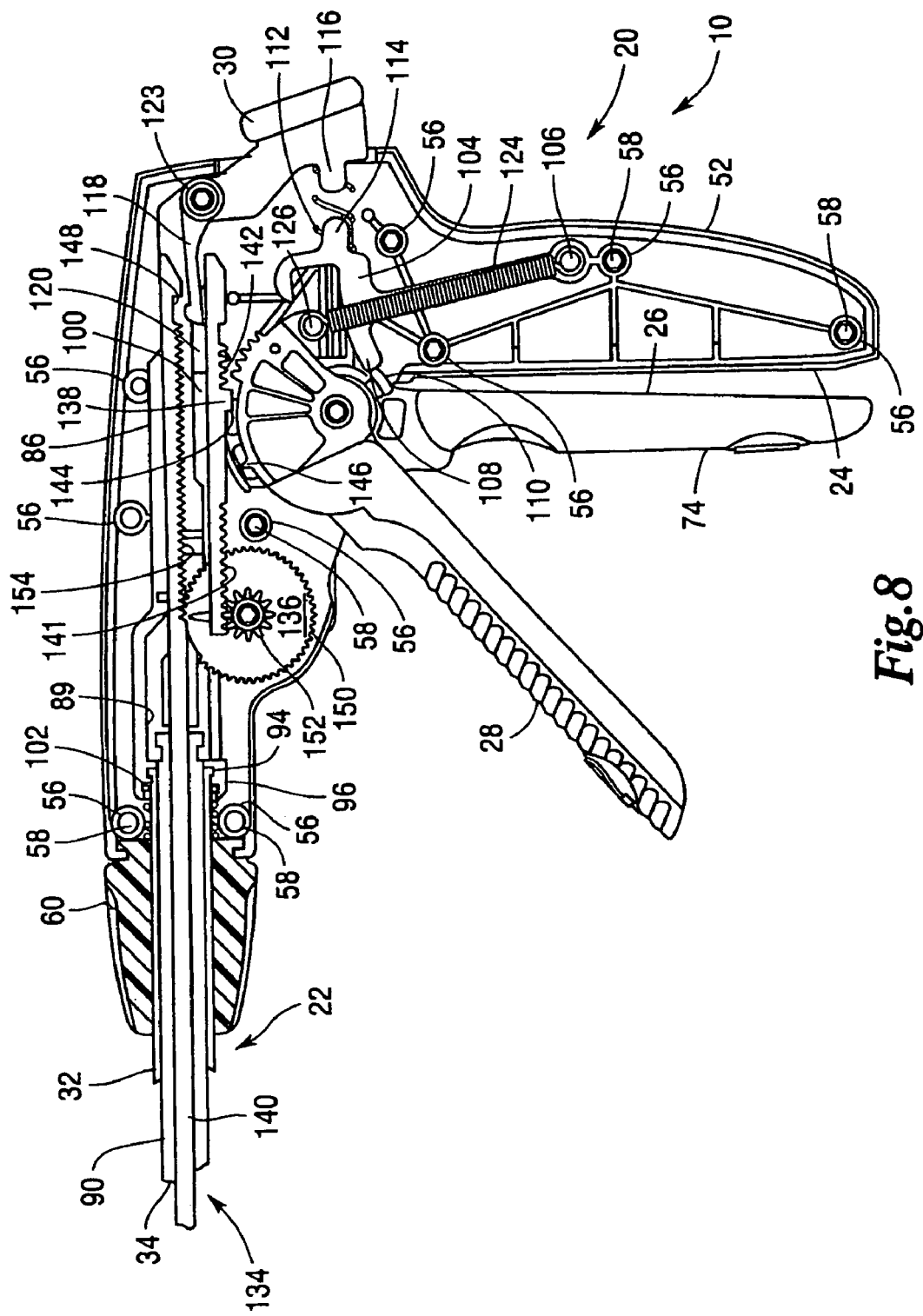
FIG. 8 depicts a side elevational view of the handle portion of the proximal end of the surgical stapling and severing instrument of FIG. 1 with the left side removed to expose interior parts in the closed ("clamped") position according to various embodiments of the present invention.

The closure trigger 26 is forward biased to an open position by a front surface 130 interacting with an engaging surface 128 of the firing trigger 28. Clamp first hook 104 that pivots top to rear in the handle portion 20 about a pin 106 restrains movement of the firing trigger 28 toward the pistol grip 24 until the closure trigger 26 is clamped to its closed position. Hook 104 restrains firing trigger 28 motion by engaging a lockout pin 107 in firing trigger 28. The hook 104 is also in contact with the closure trigger 26. In particular, a forward projection 108 of the hook 104 engages a member 110 on the intermediate section 78 of the closure trigger 26, the member 100 being outward of the bore 80 toward the handle section 74. Hook 104 is biased toward contact with member 110 of the closure trigger 26 and engagement with lockout pin 107 in firing trigger 28 by a release spring 112. As the closure trigger 26 is depressed, the hook 104 is moved top to rear, compressing the release spring 112 that is captured between a rearward projection 114 on the hook 104 and a forward projection 116 on the release button 30. As the yoke 86 moves distally in response to proximal movement of the closure trigger 26, an upper latch arm 118 of the release button 30 moves along an upper surface 120 on the yoke 86 until dropping into an upwardly presented recess 122 in a proximal, lower portion of the yoke 86. The release spring 112 urges the release button 30 outward, which pivots the upper latch arm 118 downwardly into engagement with the upwardly presented recess 122, thereby locking the closure trigger 26 in a tissue clamping position, such as depicted in FIG. 8.

The latch arm 118 can be moved out of the recess 122 to release the anvil 18 by pushing the release button 30 inward. Specifically, the upper latch arm 118 pivots upward about pin 123 of the second base section 52. The yoke 86 is then permitted to move proximally in response to return movement of the closure trigger 26.

A firing trigger return spring 124 is located within the handle portion 20 with one end attached to pin 106 of the second base section 52 and the other end attached to a pin 126 on the firing trigger 28. The firing return spring 124 applies a return force to the pin 126 for biasing the firing trigger 28 in a direction away from the pistol grip 24 of the handle portion 20. The closure trigger 26 is also biased away from pistol grip 24 by engaging surface 128 of firing trigger 28 biasing front surface 130 of closure trigger 26.

As the closure trigger 26 is moved toward the pistol grip 24, its front surface 130 engages with the engaging surface 128 on the firing trigger 28 causing the firing trigger 28 to move to its "firing" position. When in its firing position, the firing trigger 28 is located at an angle of approximately 45° to the pistol grip 24. After staple firing, the spring 124 causes the firing trigger 28 to return to its initial position. During the return movement of the firing trigger 28, its engaging surface 128 pushes against the front surface 130 of the closure trigger 26 causing the closure trigger 26 to return to its initial position. A stop member 132 extends from the second base section 52 to prevent the closure trigger 26 from rotating beyond its initial position.

The surgical stapling and severing instrument 10 additionally includes a reciprocating section 134, a multiplier 136 and a drive member 138. The reciprocating section 134 comprises a wedge sled in the implement portion 22 (not shown in FIGS. 6-9) and a metal drive rod 140. The drive member 138 includes first and second gear racks 141 and 142. A first notch 144 is provided on the drive member 138 intermediate the first and second gear racks 141, 142. During return movement of the firing trigger 28, a tooth 146 on the firing trigger 28 engages with the first notch 144 for returning the drive member 138 to its initial position after staple firing. A second notch 148 is located at a proximal end of the metal drive rod 140 for locking the metal drive rod 140 to the upper latch arm 118 of the release button 30 in its unfired position. The multiplier 136 comprises first and second integral pinion gears 150 and 152. The first integral pinion gear 150 is engaged with a first gear rack 154 provided on the metal drive rod 140. The second integral pinion gear 152 is engaged with the first gear rack 141 on the drive member 138. The first integral pinion gear 150 has a first diameter and the second integral pinion gear 152 has a second diameter which is smaller than the first diameter.

Figure 6:
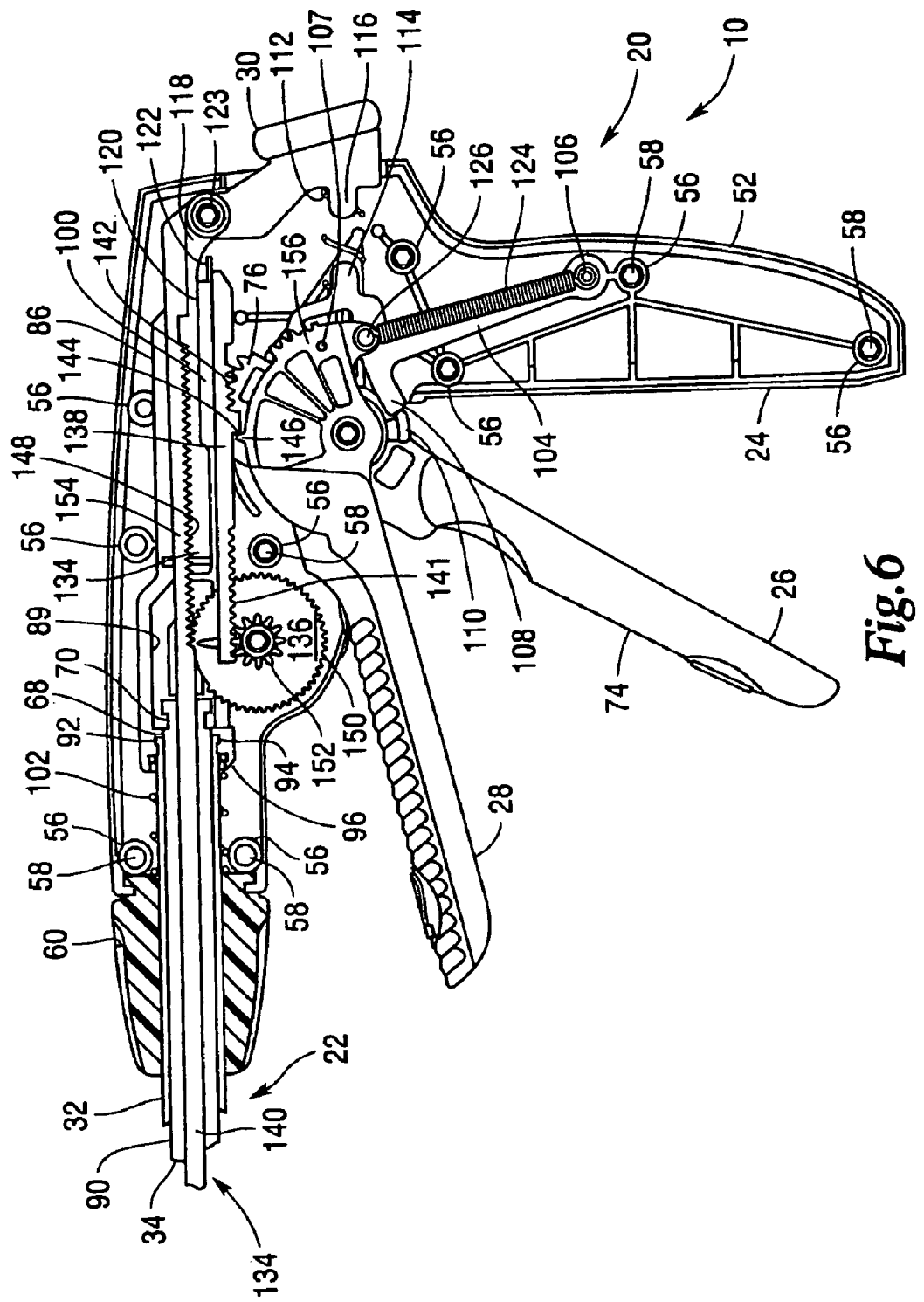
FIG. 6 depicts a side elevational view of a handle portion of a proximal end of the surgical stapling and severing instrument of FIG. 1 with a left side removed to expose interior parts in an unclamped, unfired ("start") position according to various embodiments of the present invention.
Figure 7:
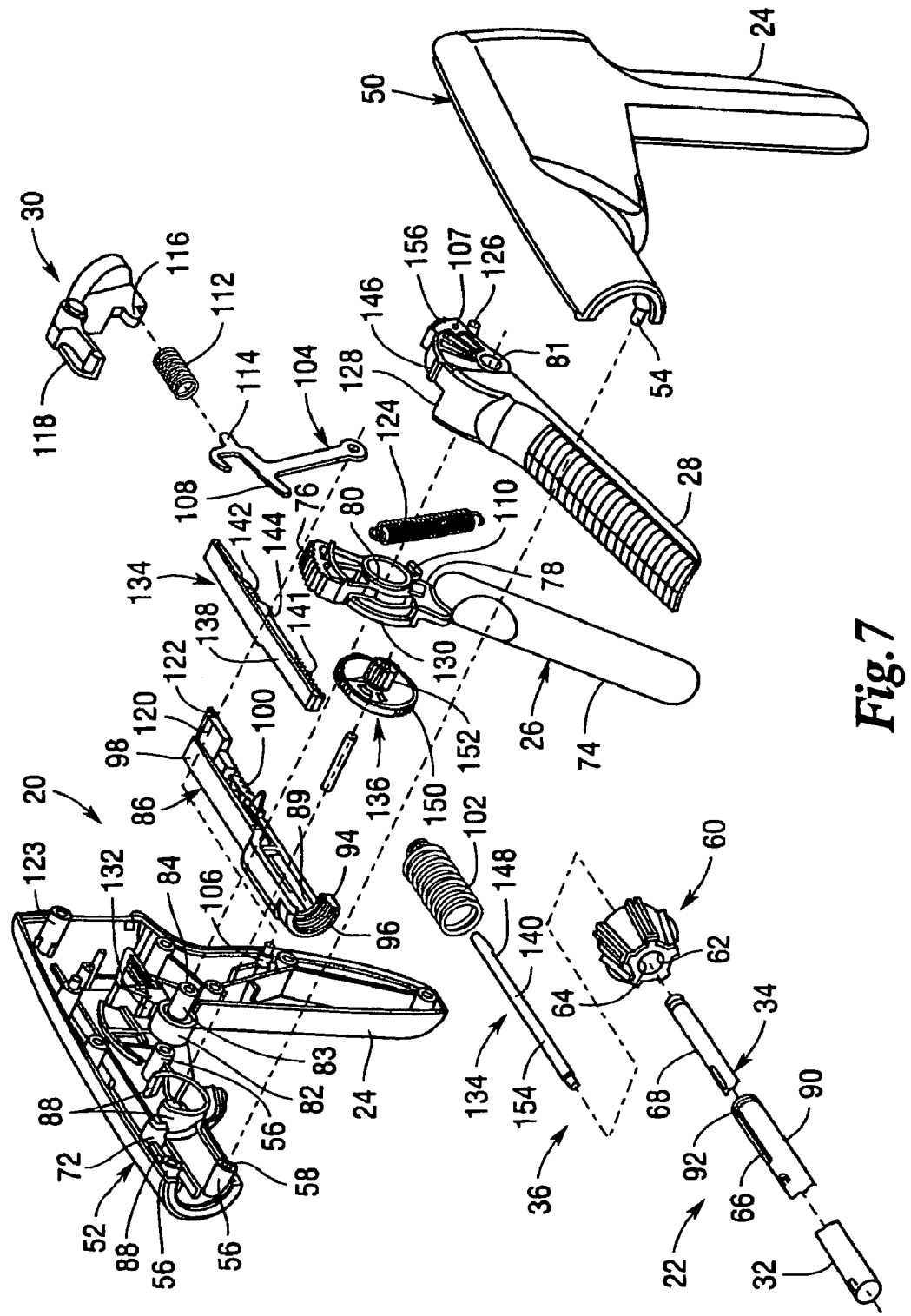
FIG. 7 depicts a perspective, exploded view of the handle portion of the proximal end of the surgical stapling and severing instrument of FIG. 1 according to various embodiments of the present invention.
Figure 9:
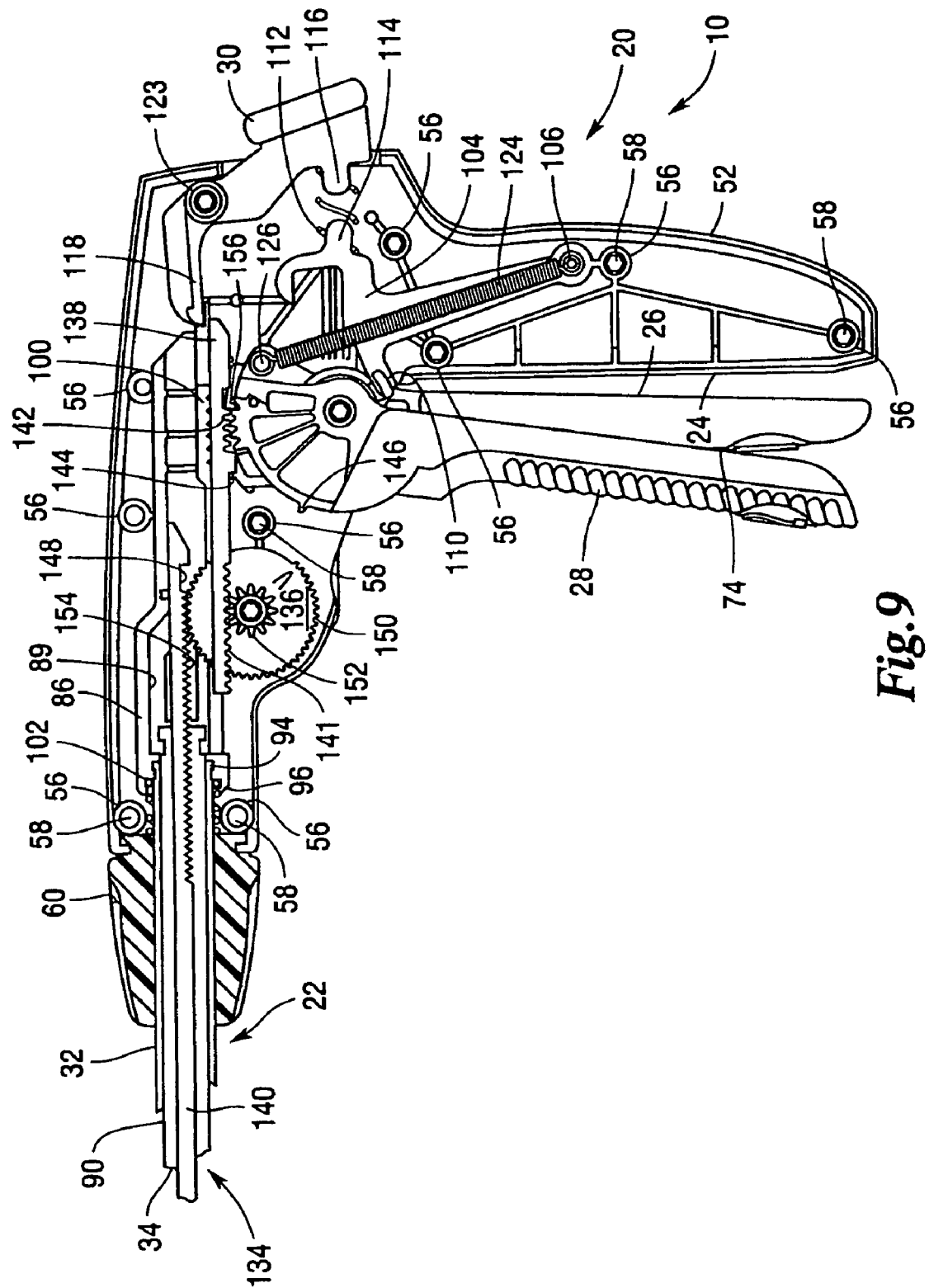
FIG. 9 depicts a side elevational view of the handle portion of proximal end of surgical stapling and severing instrument of FIG. 1 with the left side removed to expose interior parts in the stapled and severed ("fired") position according to various embodiments of the present invention.

FIGS. 6, 8 and 9 depict respectively the handle portion 20 in the start position (open and unfired), a clamped position (closed and unfired) and a fired position. The firing trigger 28 is provided with a gear segment section 156. The gear segment section 156 engages with the second gear rack 142 on the drive member 138 such that motion of the firing trigger 28 causes the drive member 138 to move back and forth between a first drive position, shown in FIG. 8, and a second drive position, shown in FIG. 9. In order to prevent staple firing before tissue clamping has occurred, the upper latch arm 118 on the release button 39 is engaged with the second notch 148 on the drive member 138 such that the metal drive rod 140 is locked in its proximal-most position, as depicted in FIG. 6. When the upper latch arm 118 falls into the recess 122, the upper latch arm 118 disengages with the second notch 148 to permit distal movement of the metal drive rod 140, as depicted in FIG. 9.

Because the first gear rack 141 on the drive member 138 and the gear rack 154 on the metal drive rod 140 are engaged with the multiplier 136, movement of the firing trigger 28 causes the metal drive rod 140 to reciprocate between a first reciprocating position, shown in FIG. 8, and a second reciprocating position, shown in FIG. 9. Since the diameter of the first pinion gear 150 is greater than the diameter of the second pinion gear 152, the multiplier 136 moves the reciprocating section 134 a greater distance than the drive member 138 is moved by the firing trigger 28. The diameters of the first and second pinion gears 150 and 152 may be changed to permit the length of the stroke of the firing trigger 28 and the force required to move it to be varied. It will be appreciated that the handle portion 20 is illustrative and that other actuation mechanisms may be employed. For instance, the closing and firing motions may be generated by automated means.

One embodiment of an end effector 12 of the surgical stapling and severing instrument 10 is depicted in further detail in FIGS. 18, 19, and 23-26. As described above, the handle portion 20 produces separate and distinct closing and firing motions that actuate the end effector 12. The end effector 12 advantageously maintains the clinical flexibility of this separate and distinct closing and firing (i.e., stapling and severing). In addition, the end effector 12 introduces the aforementioned ability to affirmatively maintain the closed spacing during firing after the clinician positions and clamps the tissue. Both features procedurally and structurally enhance the ability of the surgical stapling and severing instrument 10 by ensuring adequate spacing for instances where an otherwise inadequate amount of tissue is clamped and to enhance the clamping in instances where an otherwise excessive amount of tissue has been clamped.

Figure 10:
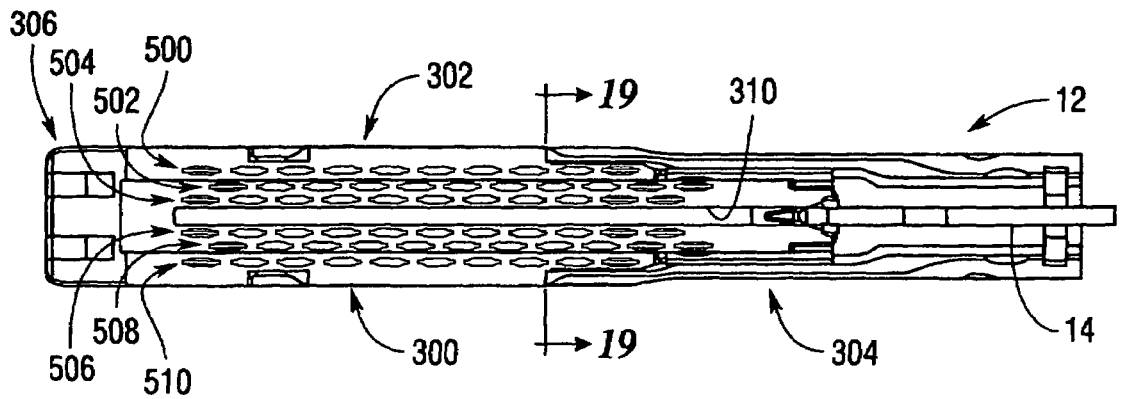
FIG. 10 depicts a plan view of a staple cartridge installed in an end effector according to various embodiments of the present invention.

FIG. 10 depicts a staple cartridge embodiment 300 of the present invention installed in the end effector 12 with the firing bar 14 in its unfired, proximal position. The staple cartridge 300 has a cartridge body 302 that is divided by an elongated slot 310 that extends from a proximal end 304 of the cartridge 300 towards a tapered outer tip 306. A plurality of staple-receiving channels 320a-320f are formed within the staple cartridge body 302 and are arranged in six laterally spaced longitudinal rows 500, 502, 504, 506, 508, 510, with three rows on each side of the elongated slot 310. Positioned within the staple-receiving channels 320a-320f are the staples 222. See FIGS. 10 and 11.

Figure 11:
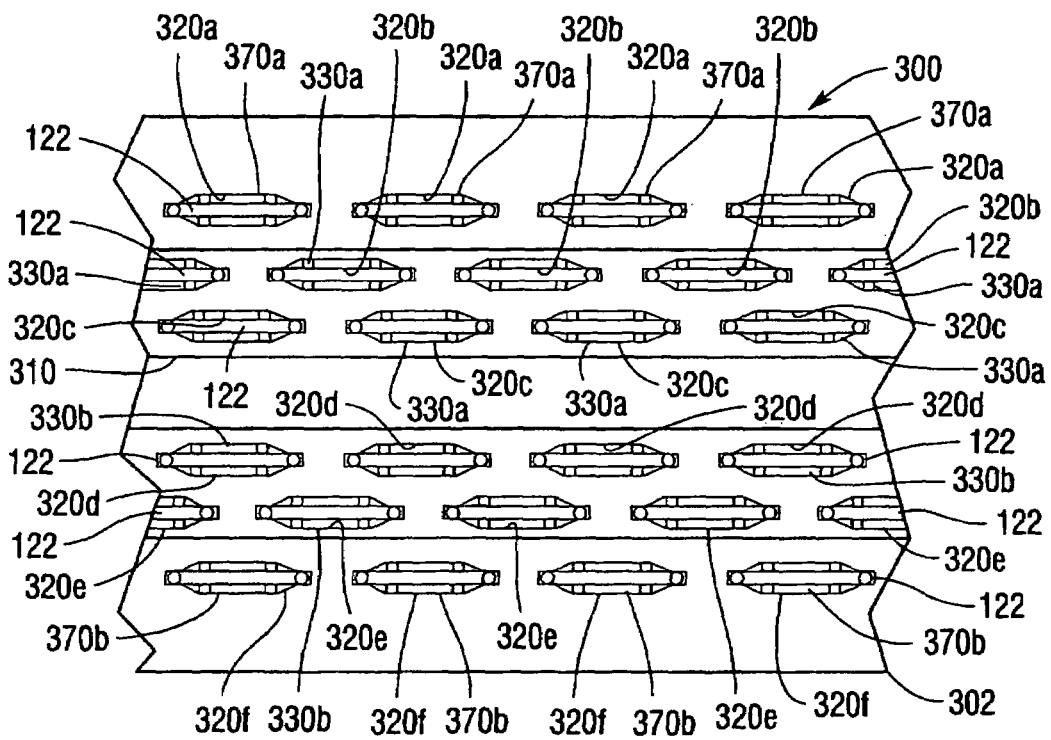
FIG. 11 is an enlarged plan view of a portion of a staple cartridge according to various embodiments of the present invention.

The cartridge 300 further includes four laterally spaced longitudinal rows of staple drivers 330a, 330b, 370a, and 370b as shown in FIG. 11. The "first" inside staple drivers 330a are slidably mounted within corresponding channels 320b and 320c such that each driver 330a supports two staples 222, one in a channel 320b and one in a channel 320c. Likewise, the "second" inside drivers 330b are slidably mounted within channels 320d and 320e such that each driver 330b supports two staples 222, one in a channel 320d and one in a channel 320e. The "outside" drivers 370a and 370b are slidably mounted within the staple-receiving channels 320a and 320f, respectively. Each of the outside drivers 370a and 370b supports a single staple 222. Drivers 370a are referred to herein as "first" outside drivers and drivers 370b are referred to herein as "second" outside drivers.

FIG. 12 illustrates a staple 222 that may be used in connection with the various embodiments of the present invention. The staple 222 includes a main portion 223 and two prongs 225. The prongs 225 each have a length "P" and the main portion has a width "W". The reader will appreciate that a variety of different types of staples may be employed. For example, for a vascular staple, "P" may be approximately 0.102 inches; for a regular staple, "P" may be approximately 0.134 inches; and for a thick tissue staple, "P" may be approximately 0.160 inches. "W" may be approximately 0.012 inches. Other sizes of staples 222 may be employed in the manners discussed below.

The inside staple drivers 330a located on one side of the elongated slot 310 are referred to herein as "first" inside staple drivers and the inside staple drivers 330b located on the other side of the elongated slot 310 are referred to herein as "second" inside staple drivers. As will be discussed in further detail below, in one embodiment, the second inside staple drivers 330b are identical to the first inside staple drivers 330a, except for their orientation in their respective channels in the cartridge body 302.

Figure 14A:
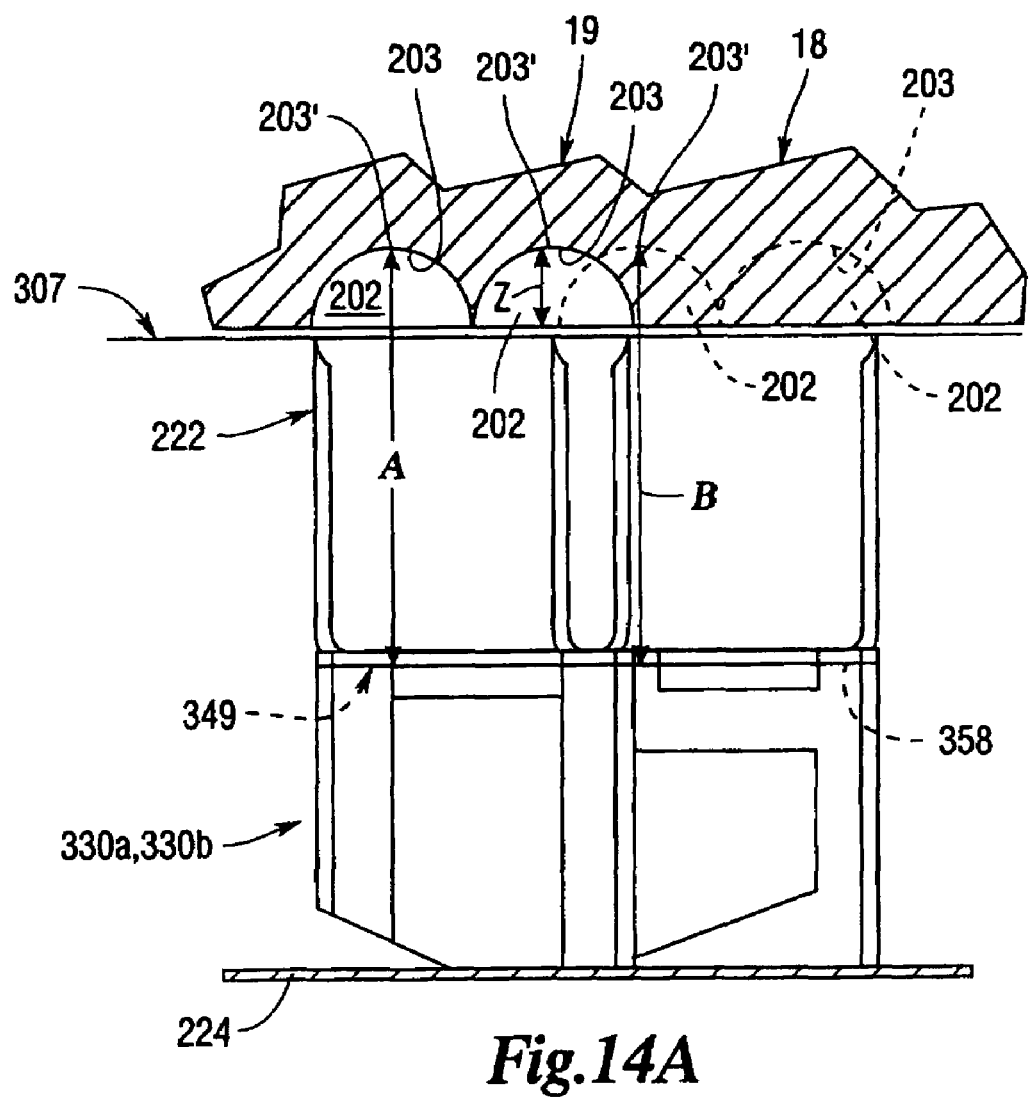
FIG. 14A is an elevational view of the inside double driver of FIG. 13 within a portion of a staple cartridge mounted in the end effector and also illustrating a corresponding portion of the anvil when in a closed position according to various embodiments of the present invention.
Figure 15:
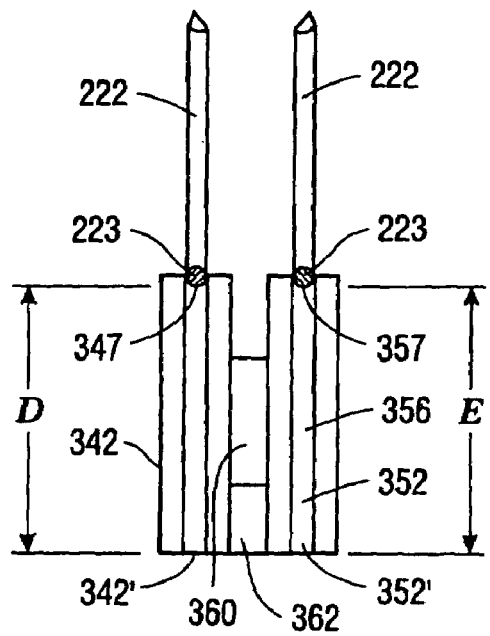
FIG. 15 is a right side elevational view of the inside double driver and staples of FIGS. 13 and 14 according to various embodiments of the present invention.

FIGS. 13-15 illustrate one embodiment of a "first" inside double driver 330a for supporting and driving staples 222. As can be seen in those Figures, the staple driver 330a has a primary driver portion 340 and a secondary driver portion 350 that is connected to the first primary portion 340 by a central base member 360. The primary driver portion 340 has a primary driver base 342 that has a groove 343 therein adapted to mate with a corresponding vertically extending tongue (not shown) in the cartridge body 302 for guiding and stabilizing the driver 330a as it moves within its respective channel. The primary driver portion 340 further has a first forward support column 344 and a first rearward support column 346 protruding upward from the first driver base 342. The first forward support column 344 has a first forward staple-receiving groove 345 therein and the first rearward support column 346 has a first rearwardly staple-receiving groove 347 therein. See FIGS. 13-15. The first forward support column 344 and the first rearward support column 346 are spaced from each other and collectively form a first staple cradle 348 for supporting the main portion 223 of the staple 222 therein in an upright position (i.e., prongs facing the anvil). Similarly, the secondary driver portion 350 has a secondary driver base 352 and a secondary forward support column 354 and a secondary rearward support column 356 protruding out from the second driver base 352. The secondary forward support column 354 has a secondary forward staple-receiving groove 355 therein and the secondary rearward support column 356 has a secondary rearward staple-receiving groove 357 therein. The secondary forward support column 354 and the secondary rearward support column 356 are spaced from each other and collectively form a secondary staple cradle 358 for supporting the main portion 223 of another staple 222 therein.

As can be seen in FIGS. 13 and 15, the central base member 360 has an angled rearwardly facing edge 362 adapted to be engaged by a corresponding sled cam as will be discussed in further detail below. As can be seen in FIGS. 13 and 14, in this embodiment, the secondary forward support column 354 of the secondary driver portion is oriented relative to the first rearward support column 346 such that the staple 222 that is supported in the secondary staple cradle 358 is longitudinally offset from the staple 222 in the first staple cradle 348. The reader will appreciate that the first inside drivers 330a are each installed in one orientation into a corresponding pair of channels 320b and 320c located on one side of the elongated slot 310 in the cartridge body 302. The second inside staple drivers 330b (located on the opposite side of the elongated slot 310 from the first inside staple drivers 330a) comprise inside drivers 330a rotated 180 degrees so that their respective angled surfaces 363 face towards the proximal end 304 of the cartridge 300 to enable them to be installed in pairs of corresponding channels 320d and 320e. Thus, in this embodiment, only one inside driver configuration is employed which thereby eliminates the need for two different inside staple driver configurations for channels on each side of the elongated slot 310.

FIGS. 16 and 17 illustrate one embodiment of a "first" outside staple driver 370a. As can be seen in those Figures, a first outside staple driver 370a has a second base 372 that has an angled rearwardly facing portion 374. Protruding upward from the second base 372 is a second forward support column 375 that has a second forward staple-receiving groove 376 therein. A second rearward support column 377 also protrudes upward from the second base 372 in a spaced-apart relationship with respect to the second forward support column 375. The second rearward support column 377 has a second rearward staple-receiving groove 378 therein. The support columns 375, 377 collectively form a second staple cradle 379 that is configured to support a staple 222 therein in an upright position as illustrated in FIGS. 16 and 17. The staple drivers 370a also have a laterally protruding rib 371 which is received in a corresponding groove (not shown) in the cartridge body 302 for guiding and stabilizing the driver 370a as it moves within its respective channel.

Figure 19:
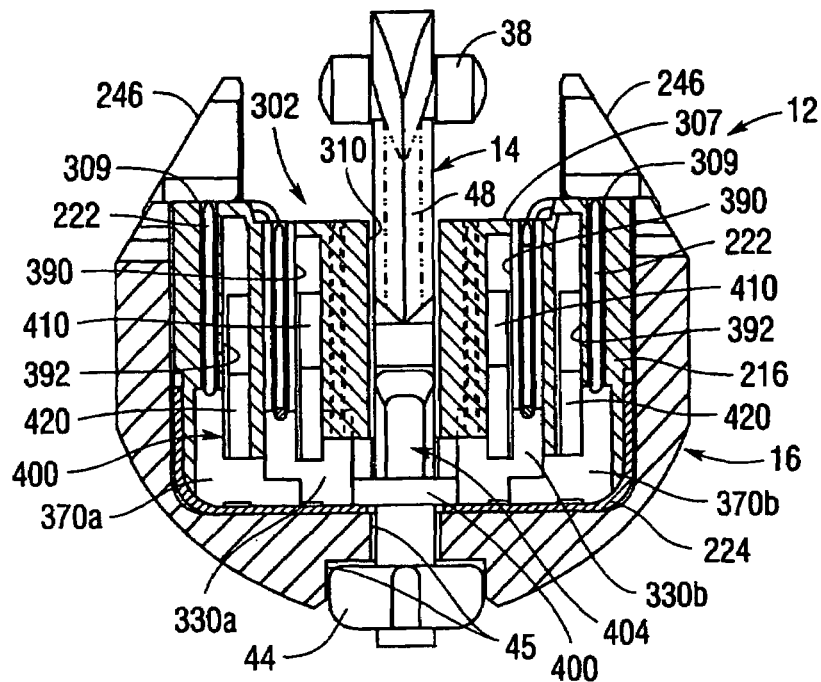
FIG. 19 is a section view taken along line 19-19 of FIG. 10 showing the cross-sectional relationship between the firing bar, elongate channel, wedge sled, staple drivers, staples and staple cartridge according to various embodiments of the present invention.
Figure 19A:
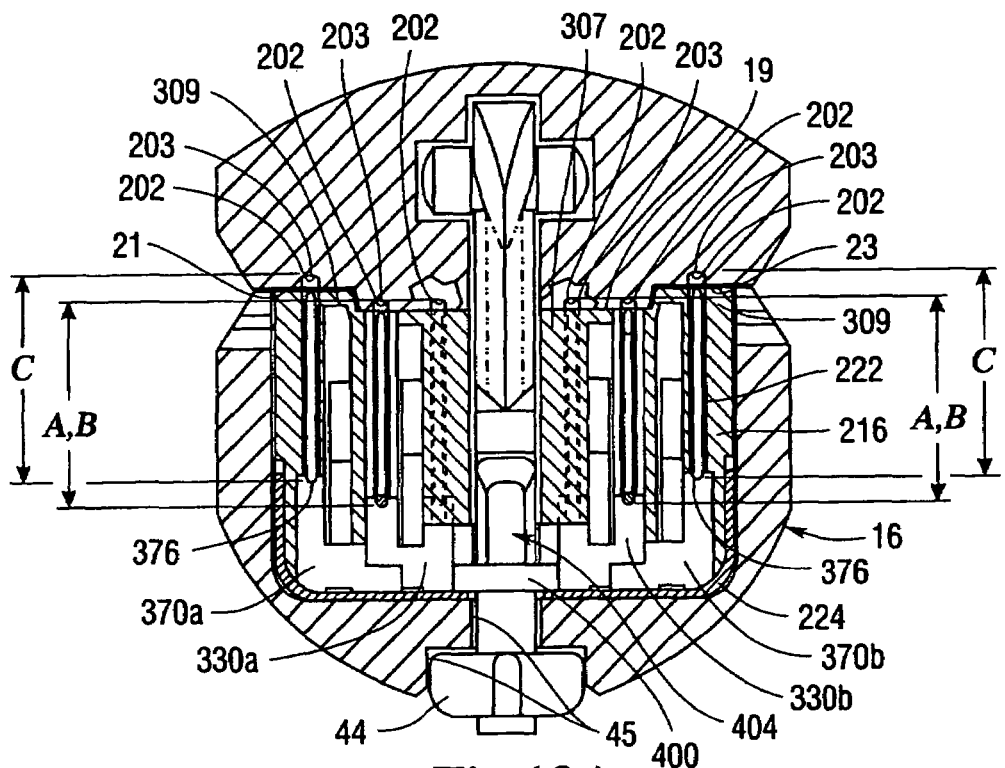
FIG. 19A is another cross-sectional view of an end effector showing the cross-sectional relationship between the firing bar, elongate channel, wedge sled, staple drivers, staples, staple cartridge and anvil according to various embodiments of the present invention.

The reader will appreciate that a first outside driver 370a is installed in one orientation into a corresponding channel 320a on one side of the elongated slot 310. A second outside staple driver 370b (to be located on the opposite side of the elongated slot 310 from the first outside staple drivers 370a) comprises an outside driver 370a rotated 180 degrees so that the angled surface 374' thereon faces toward the proximal end 304 of the cartridge 300 to enable it to be installed in a corresponding channel 320f in the cartridge body 302. Thus, in this embodiment, only one outside staple driver configuration is employed which avoids the need for two different outside staple driver configurations for channels on each side of the elongated slot 310. FIGS. 19 and 19A illustrate in cross-section one embodiment of a staple cartridge of the present invention mounted within one type of end effector 12. The end effector 12 in this embodiment employs a "stepped" anvil 18 of the type illustrated in FIGS. 23-25. In other embodiments, however, the bottom surface of the anvil is planar and not stepped. Other As can be seen in FIGS. 19A, and 23-25, the anvil 18 has a central portion 19 that is offset or not coplanar with the two lateral side portions 21, 23. Accordingly, in this embodiment, the upper surface 306 of the cartridge 300 is provided with a recessed central portion 307 and two lateral side portions 309 that are adapted to closely mate with the corresponding portions 19, 21, 23, respectively, of the anvil 18, when the anvil 18 is in the closed position. See FIG. 19A.

Figure 24:
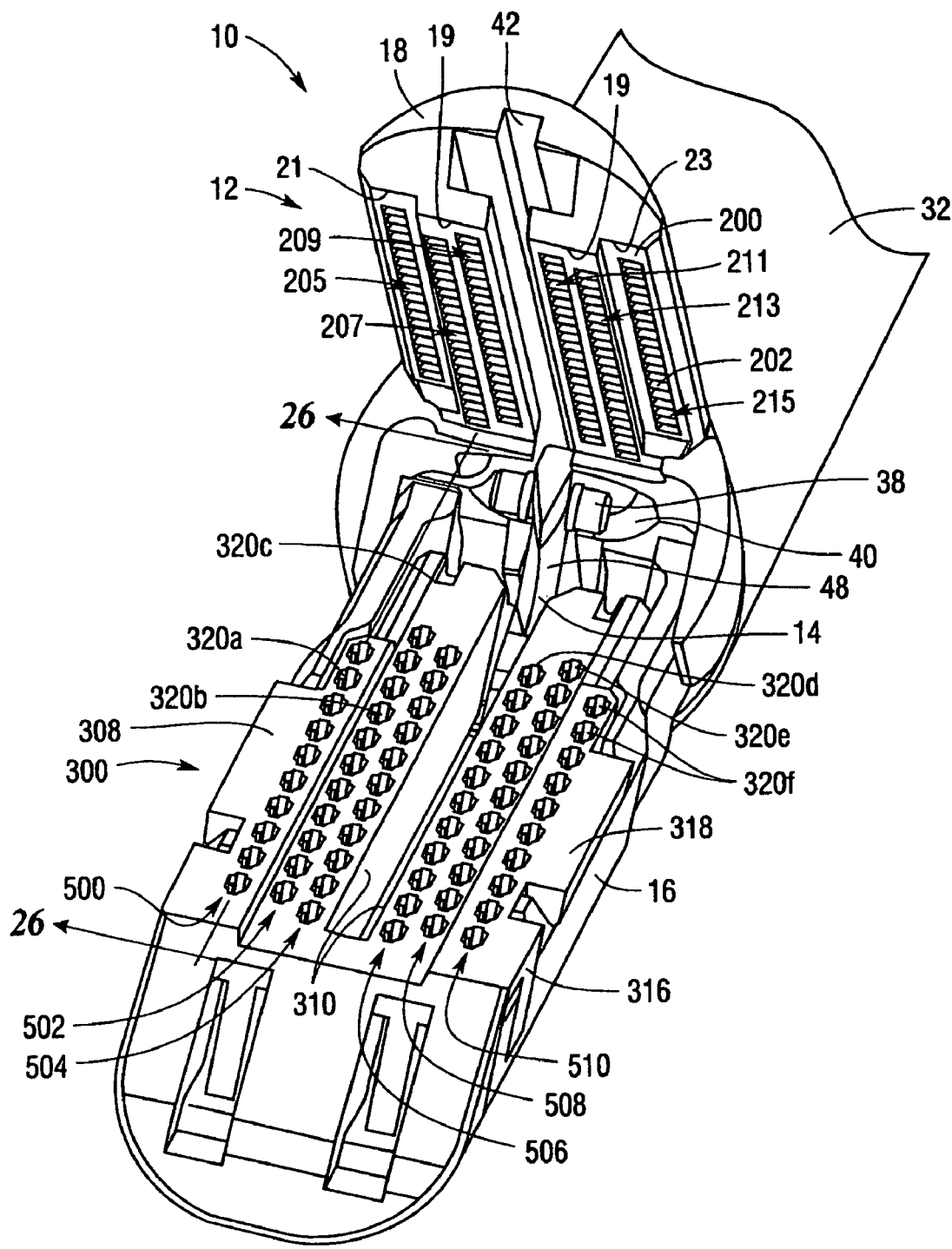
FIG. 24 is an isometric view of the end effector at the distal end of the surgical stapling and severing instrument of FIG. 1 with the anvil in the up or open position exposing the staple cartridge and cutting edge of the firing bar according to various embodiments of the present invention.

As can be seen in FIG. 24, in this embodiment, the under surfaces 200 of anvil 18 are provided with a series of forming pockets 202 that may be arranged in rows that correspond to the rows of channels in the cartridge 300. That is, row 205 of pockets 202 may correspond to channel row 500. Row 207 of pockets may correspond to channel row 502. Row 209 of pockets 202 may correspond to channel row 504. Row 211 of pockets 202 may correspond to channel row 506. Row 213 of pockets 202 may correspond to channel row 508. Row 215 of pockets 202 may correspond to channel row 510. Each pocket 202 has at least one forming surface 203 therein that is adapted to contact the ends of the staple prongs 225 being driven therein to thereby cause the prongs 225 to bend inwardly toward each other. In one embodiment, each pocket 202 has two intersecting arcuate forming surfaces 203 that are oriented as shown in FIG. 14A. Each arcuate forming surface has an apex 203' that defines a maximum pocket depth "Z". However other forming pocket configurations could be employed.

Returning to FIGS. 18 and 19, it can be seen that in one embodiment, the cartridge body 302 is mounted within the cartridge tray 224. As illustrated in FIG. 19, the cartridge body 302 is formed with two inside longitudinally extending slots 390 and two outside longitudinally extending slots 392. Slots 390 and 392 extend from the proximal end 304 of the cartridge to its tapered outer tip 306 (shown in FIG. 10). This embodiment further includes a wedge sled 400 that slidably supported on the cartridge tray 224. One wedge sled embodiment 400 includes a pair of inside sled cams 410, wherein one inside sled cam 410 corresponds to one of the inside longitudinally extending slots 390 and wherein the other inside sled cam 410 corresponds to the other inside longitudinally extending slot 390. See FIG. 19. The wedge sled 400 further includes a pair of outside sled cams 420, wherein one outside sled cam 420 corresponds to one of the outside longitudinally extending slots 392 and the other outside sled cam 420 corresponds to the other outside longitudinally extending slot 392 as shown in FIG. 19. When assembled, the cartridge tray 224 holds the wedge sled 400 and the drivers 330a, 330b, 370a, 370b inside the cartridge body 302.

Figure 18:
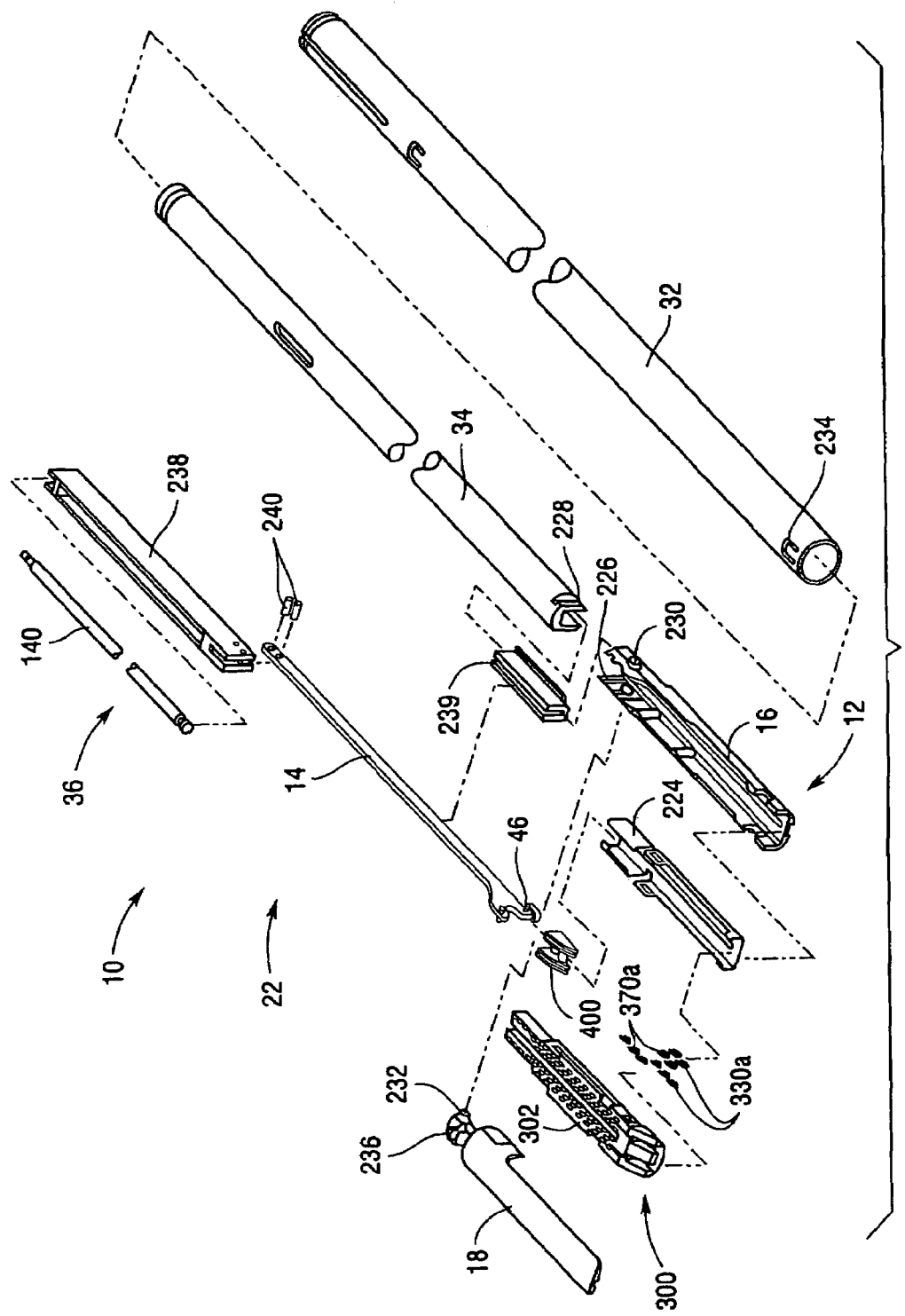
FIG. 18 is an isometric exploded view of the implement portion of the surgical stapling and severing instrument of FIG. 1 according to various embodiments of the present invention.

As can be seen in FIG. 18, the elongate channel 16 has a proximally placed attachment cavity 226 that receives a channel anchoring member 228 on the distal end of the frame .34 for attaching the end effector 12 to the handle portion 20. The elongate channel 16 also has an anvil cam slot 230 that pivotally receives an anvil pivot 232 of the anvil 18. The closure sleeve 32 that encompasses the frame 34 includes a distally presented tab 234 that engages an anvil feature 236 proximate but distal to the anvil pivot 232 on the anvil 18 to thereby effect opening and closing of the anvil 18. The firing drive member 36 is shown as being assembled from the firing bar 14 attached to a firing connector 238 by pins 240, which in turn is rotatingly and proximally attached to the metal drive rod 140. The firing bar 14 is guided at a distal end of the frame by a slotted guide 239 inserted therein.

Figure 20:
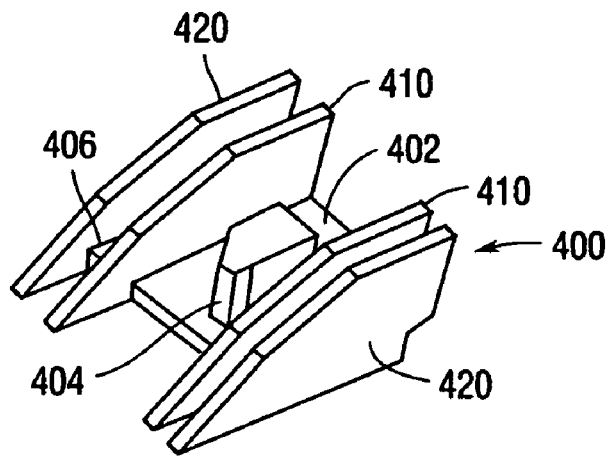
FIG. 20 is a perspective view of one wedge sled according to various embodiments of the present invention.
Figure 21:
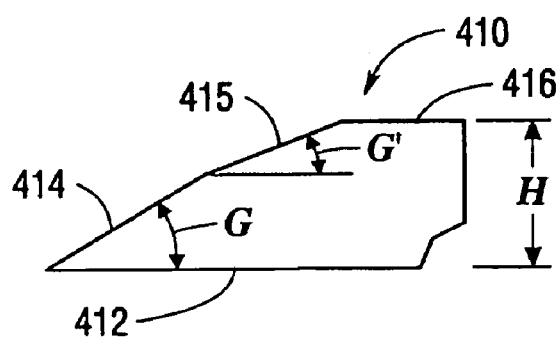
FIG. 21 is a side elevational view of an inside sled cam of the wedge sled depicted in FIG. 20 according to various embodiments of the present invention.
Figure 22:
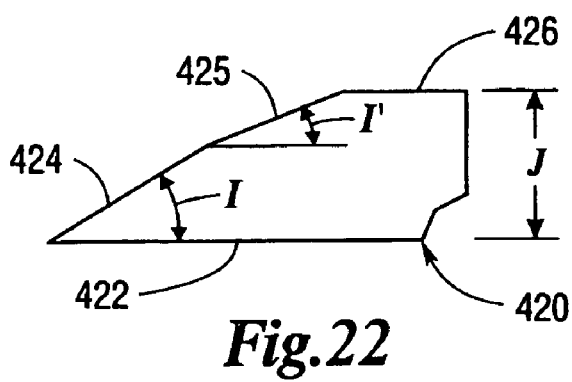
FIG. 22 is a side elevational view of an outside sled cam of the wedge sled depicted in FIG. 20 according to various embodiments of the present invention.
Figure 23:
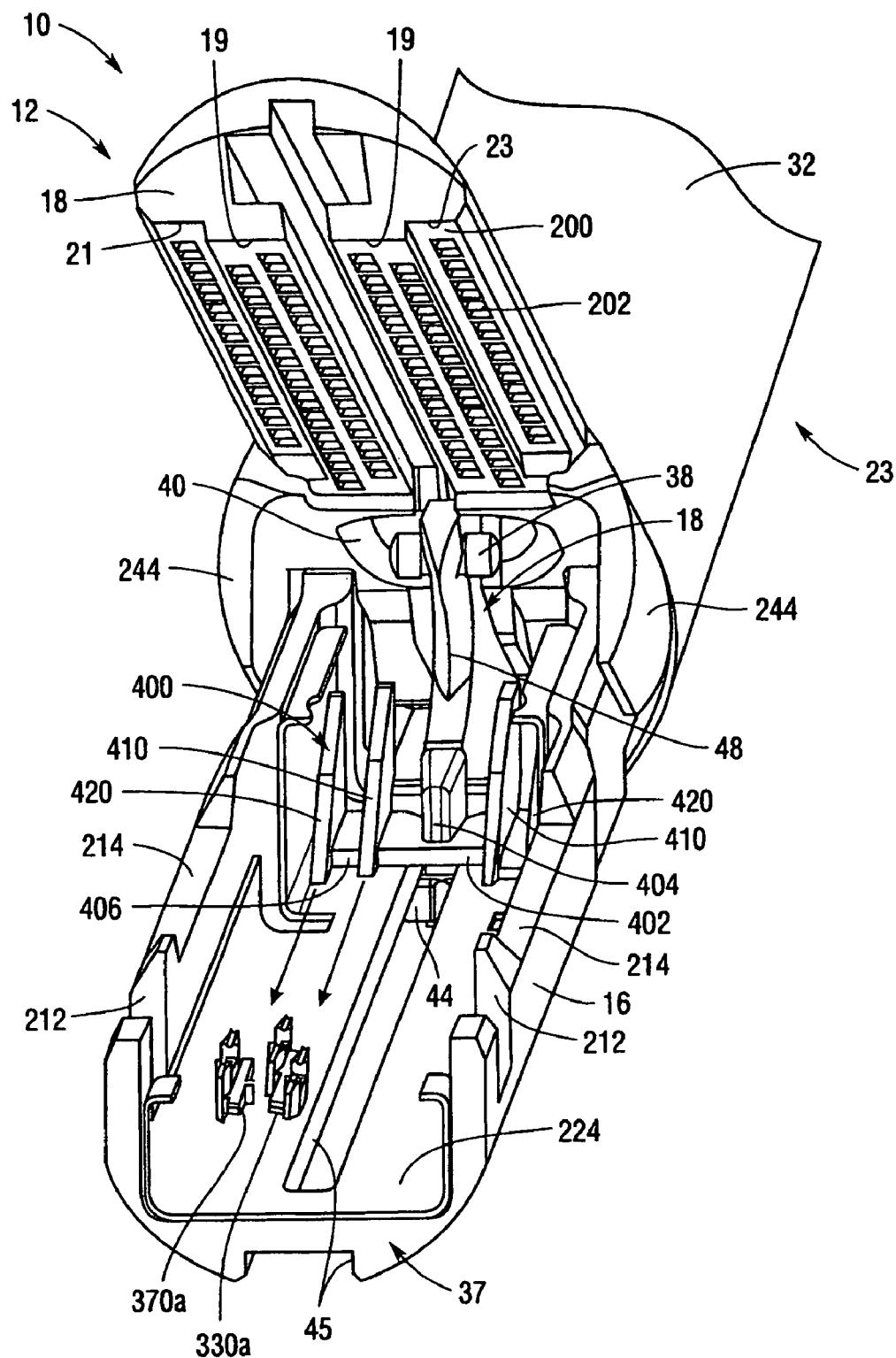
FIG. 23 is an isometric view of the end effector at the distal end of the surgical stapling and severing instrument of FIG. 1 with the anvil in the up or open position with the cartridge largely removed exposing a single staple driver and a double staple driver as exemplary and the wedge sled in its start position against a middle pin of the firing bar according to various embodiments of the present invention.

FIGS. 20-23 illustrate one embodiment of the wedge sled 400 of the present invention. As can be seen in FIGS. 20 and 23, the wedge sled 400 includes a central spacer portion 402 that extends between the inside sled cams 410. A pusher block 404 is formed on the central spacer portion 402 for engagement with the middle pin 46 of the firing bar 14. A side profile of one embodiment of an inside sled cam 410 is depicted in FIG. 21. As can be seen in that Figure, the inside sled cam 410 has a bottom surface 412, and a first camming surface 414 that forms an angle "G" with the bottom surface 412 and a second camming surface 415 that extends to a top surface 416. In one embodiment, for example, the angle "G" may be 35 degrees and the angle "G'" may be 20 degrees. The height of the inside sled cam 410 (the distance between the bottom surface 412 and the top surface 416) is represented as "first" sled cam height "H". In one embodiment, distance "H" is approximately 0.173 inches and the length of the top surface 416 may vary from embodiment to embodiment. As will be further evident as the present Detailed Description proceeds, the first sled cam height represents the vertical distance that the inside sled cams 410 will drive the corresponding inside drivers 330a, 330b toward the anvil 18 during operation.

The wedge sled 400 further comprises lateral spacer portions 406 that extend between the inside sled cams 410 and the outside sled cams 420 as shown in FIGS. 20 and 23. A side profile of one embodiment of an outside sled cam 420 is depicted in FIG. 22. In this embodiment, the outside sled cam 420 has a bottom surface 422 and a first camming surface 424 that forms an angle "I" with respect to the bottom surface 422 and a second canning surface 425 that to a top surface 426. In one embodiment, angle "I" may be approximately 35 degrees and angle "I'" may be approximately 20 degrees. The height of the outside sled cam 420 (the distance between the bottom surface 412 and the top surface 416) is represented as the "second" sled cam height "J". In one embodiment, distance "J" is approximately 0.163 inches. The second sled cam height represents the vertical distance that the outside sled cams 420 will drive the corresponding outside drivers 370a, 370b toward the anvil 18 during operation. The reader will understand that the above-recited dimensions are illustrative of one embodiment and may vary for other embodiments.

With particular reference to FIG. 23, a portion of the staple cartridge 300 is removed to expose portions of the elongate channel 16, such as recesses 212, 214 and to expose some components of the staple cartridge 300 in their unfired position. In particular, the cartridge body 302 (shown in FIG. 18) has been removed. The wedge sled 400 is shown at its proximal, unfired position with a pusher block 404 contacting the middle pin 46 (not shown in FIG. 23) of the firing bar 14. The wedge sled 400 is in longitudinal sliding contact upon the cartridge tray 224 and includes wedges sled cams 410, 420 that force upward the double drivers 330a, 330b and the single drivers 370b, 370b as the wedge sled 400 moves distally. Staples 222 (not shown in FIG. 23) resting upon the drivers 330a, 330b, 370a, 370b are thus also forced upward into contact with the anvil forming pockets 202 in anvil 18 to form closed staples. Also depicted is the channel slot 45 in the elongate channel 16 that is aligned with the elongated slot 310 in the staple cartridge 300.

FIG. 24 depicts the end effector 12, which is in an open position by a retracted closure sleeve 32, with a staple cartridge 300 installed in the elongate channel 16. The firing bar 14 is at its proximal position, with the upper pin 38 aligned in a non-interfering fashion with the anvil pocket 40. The anvil pocket 40 is shown as communicating with the longitudinal anvil slot 42 in the anvil 18. The distally presented cutting edge 48 of the firing bar 14 is aligned with and proximally from removed from the vertical slot 49 in the staple cartridge 300, thereby allowing removal of a spent cartridge and insertion of an unfired cartridge, which may be "snapfit" into the elongate channel 16. Specifically, in this embodiment, extension features 316, 318 of the staple cartridge 300 engage recesses 212, 214, respectively (shown in FIG. 23) of the elongate channel 16.

Figure 25:
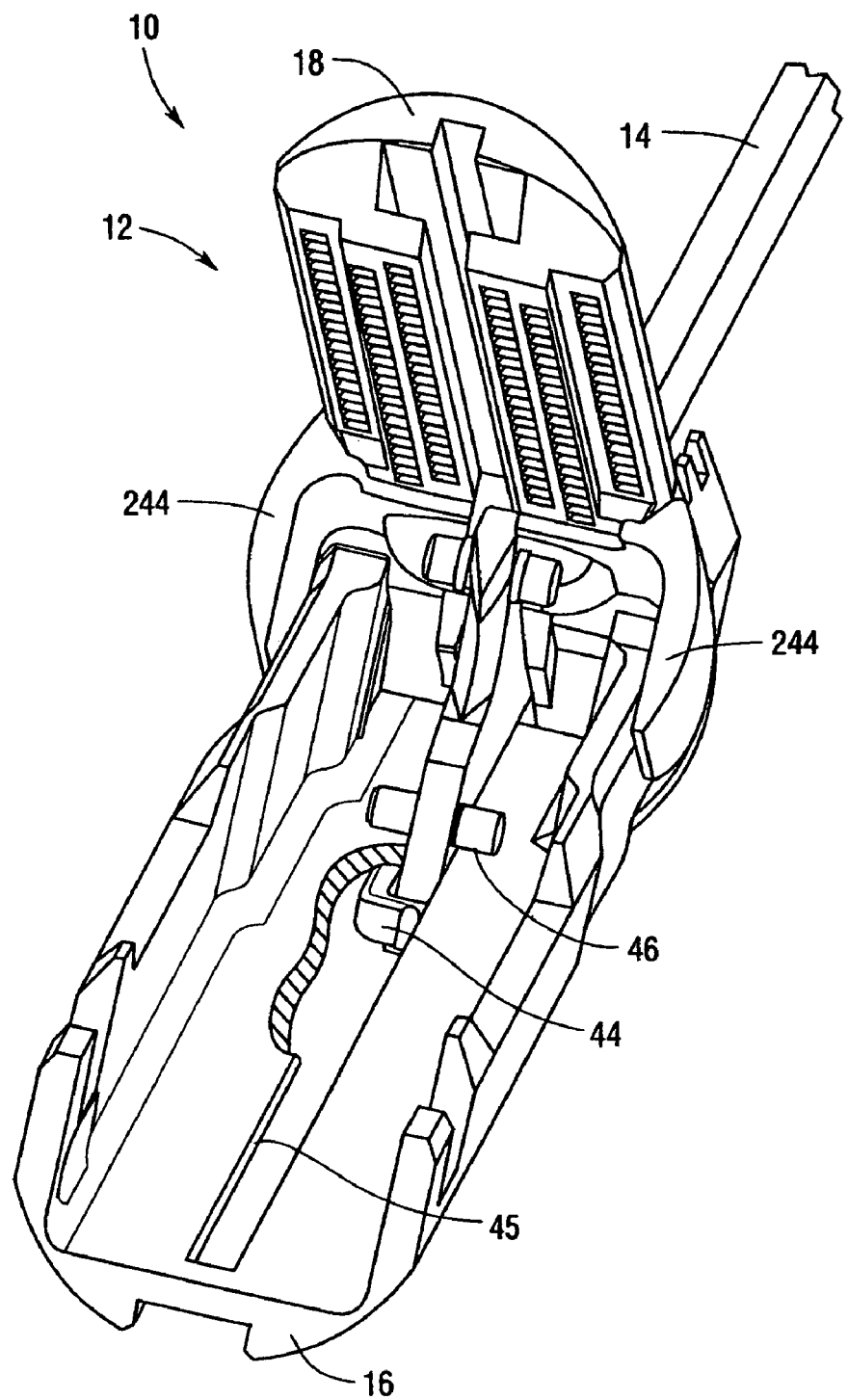
FIG. 25 is an isometric view of the distal end of the surgical stapling and severing instrument of FIG. 1 with the anvil in the up or open position with the staple cartridge completely removed and a portion of an elongate channel removed to expose a lowermost pin of the firing bar according to various embodiments of the present invention.
Figure 26:
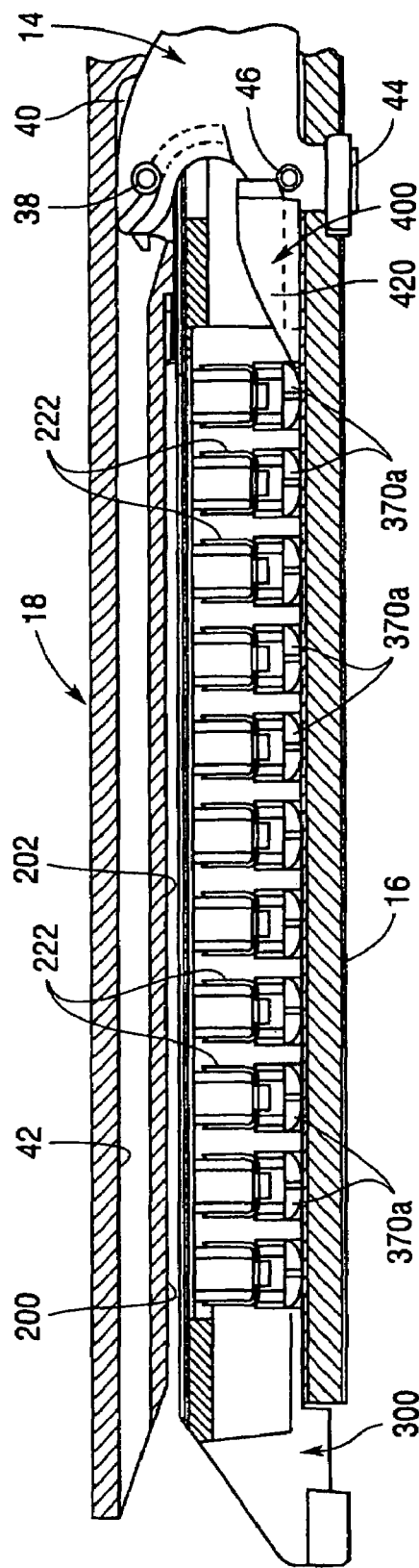
FIG. 26 is a side elevation view in section showing a mechanical relationship between the anvil, elongate channel, and staple cartridge in the closed position of the surgical stapling and severing instrument of FIG. 1, the section generally taken along lines 26-26 of FIG. 24 to expose wedge sled, staple drivers and staples but also depicting the firing bar along the longitudinal centerline according to various embodiments of the present invention.

FIG. 25 depicts the end effector 12 of FIG. 23 with all of the staple cartridge 300 removed to show the middle pin 46 of the firing bar 14 as well as portion of the elongate channel 16 removed adjacent to the channel slot 45 to expose the firing bar cap 44. In addition, portions of the shaft 23 are removed to expose a proximal portion of the firing bar 14. Projecting downward from the anvil 18 near the pivot is a pair of opposing tissue stops 244 which serve to prevent tissue from being positioned too far up into the end effector 12 during clamping. FIG. 26 depicts the end effector 12 in a closed position with the firing bar 14 in an unfired position. The upper pin 38 is in the anvil pocket 40 and is vertically aligned with the anvil slot 42 for distal longitudinal movement of the firing bar 14 during firing. The middle pin 46 is positioned to push the wedge sled 400 distally so that the sled cams 410, 420 contact and lift double drivers 330a, 330b and the single drivers 370a, 370b, respectively, to drive them upwardly toward the anvil 18.

Figure 15A:
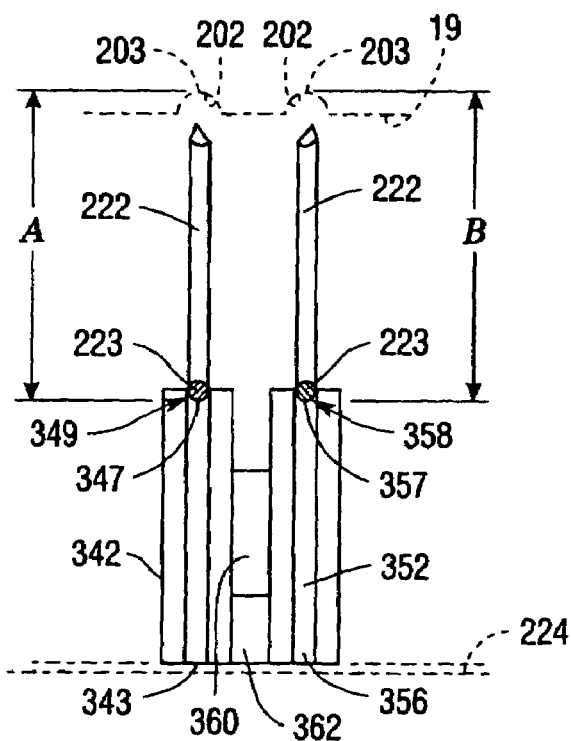
FIG. 15A is another side elevational view of the inside double driver of FIG. 15 wherein corresponding portions of the cartridge tray and anvil are illustrated in broken lines to depict the relationships therebetween according to various embodiments of the present invention.

As can be appreciated from reference to FIGS. 14A, 15A and 19A, in one embodiment of the present invention, the distance between the bottom of the first staple-receiving grooves 345, 347 forming the first staple cradle 349 and the apex 203' of forming surfaces 203 of the corresponding forming pocket 202 of anvil 18, when the anvil 18 is in the closed position and when the inside driver 330a, 330b is supported on the cartridge tray 224, is referred to herein as the first staple forming distance "A". The distance between the bottom of the secondary staple-receiving grooves 345, 347 forming the secondary staple cradle 349 and the apex 203' of the forming surface 203 of the corresponding forming pocket 202 in the anvil 18 when the anvil 18 is in the closed position and the inside driver 330a, 330b is supported on the cartridge tray 224 is referred to herein as the secondary staple forming distance "B". In one embodiment, the first staple forming distance "A" and the secondary staple forming distance "B" are substantially equal to each other. In other embodiments, those distances "A" and "B" may differ from each other.

As illustrated in FIGS. 16A and 19A the distance between the bottom of the second staple-receiving grooves 376, 378 that form the second staple cradle 379 and the apex 203' of the forming surface 203 of a corresponding forming pocket 202 in anvil 18 when the anvil 18 is in the closed position and the outside drivers 370a, 370b are supported on the cartridge channel 224, is referred to herein as a "second" staple forming distance "C".

Figure 27:
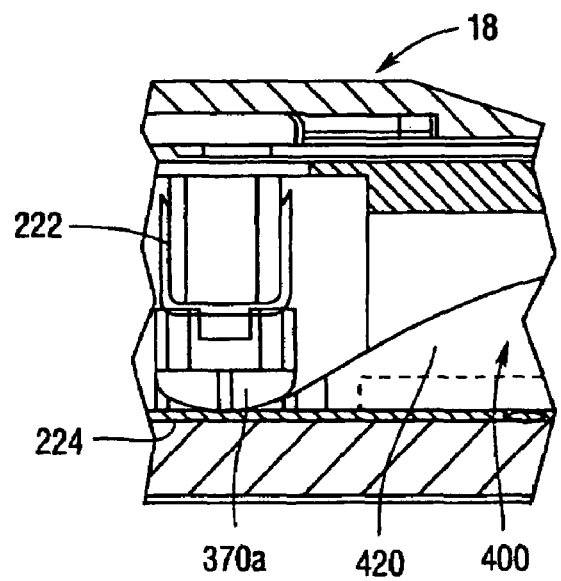
FIG. 27 is a cross-sectional view of a portion of a staple cartridge wherein an outside cam of a wedge is adjacent to an outside single driver according to various embodiments of the present invention.
Figure 28:
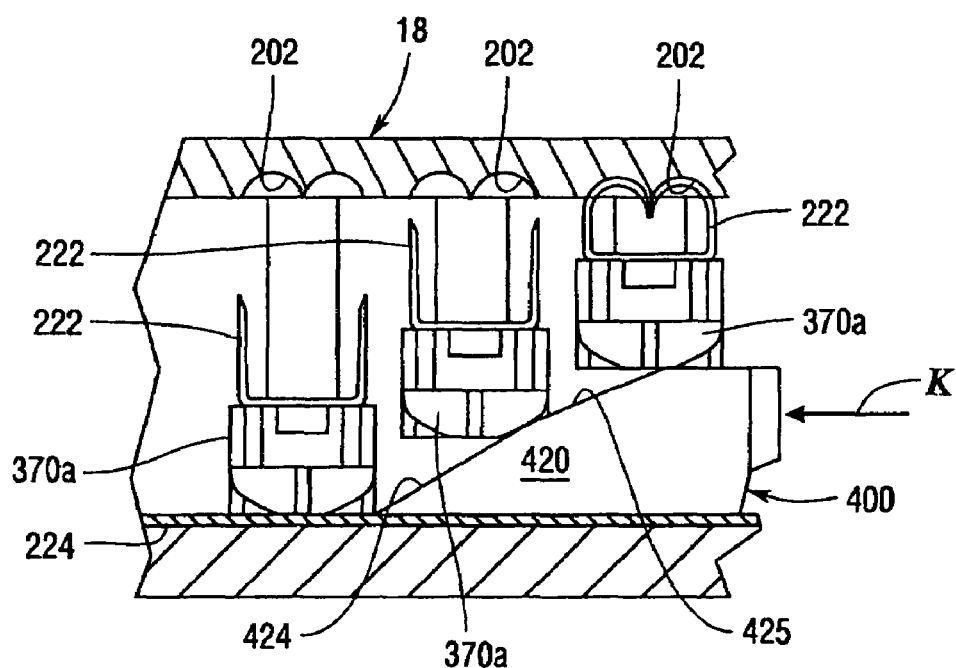
FIG. 28 is a cross-sectional view of a portion of a staple cartridge wherein an outside cam of a wedge sled is engaging three outside single drivers according to various embodiments of the present invention.

FIGS. 27 and 28 illustrate the forming of staples supported on some of the first outside drivers 370a. In FIG. 27, one of the outside sled cams 420 of the wedge sled 400 is initially contacting one of the outside drivers 370a. As the wedge sled 400 continues in the driving direction represented by arrow "K" in FIG. 28, the outside sled cam 420 causes the outside drivers 370a drive the staples 222 supported thereby into the staple forming pockets 202 in the anvil 18. Likewise, as the wedge sled 400 is driven in the driving direction "K", the inside sled cams 410 contact the inside drivers 330a, 330b and causes them to drive the staples 222 supported thereby into the corresponding staple forming pockets 202 in the anvil 18.

As indicated above, in some applications involving an area of varied tissue composition, it can be desirable to form rows of staples wherein the formed (final) heights of the staples in a row that is the farthest distance away from the cut line are greater than the formed (final) heights of those staples in the row that is closest to the cut line. In other applications, it may be desirable for the formed heights of the staples in a single row to increase (or decrease) from staple to staple. Another clinical benefit would be to have the formed heights of the staples in the outermost rows larger than formed heights of the staples in the inside rows. The various embodiments of the subject invention can provide these results while employing identical staples in all of the rows.

In the description to follow, those staples 222 in the outermost rows 520, 530 of staples (those staples formed using the outside staple drivers 370a, 370b) will be referred to hereinafter as staples 222' and those staples in the innermost rows 522, 524, 526, 528 of staples (those staples formed using the inside staple drivers 330a, 330b) will be referred to hereinafter as staples 222". It will be understood, however, that staples 222' and 222" are identical to each other prior to being formed by the various embodiments of the present invention. That is, staples 222' and 222" each have identical prong lengths "P" and widths "W". Returning to FIGS. 14A-16A and 21 and 22, the above desired effects may be attained by altering the staple forming distances "A", "B", and "C" relative to each other and/or the sled cam heights "H" and "J". In one embodiment of the subject invention, for example, the height "H" of each of the inside sled cams 410 is substantially equal to the sled height "J" of each of the outside sled cams 420. See FIGS. 21 and 22. In this embodiment, the staple forming distances "A" and "B" are substantially equal to each other, but distances "A" and "B" are less than the staple forming distance "C". The distance "D" between the bottoms of the first staple-receiving grooves 345, 347 and the bottom surface 342' of the primary driver base 342 is substantially equal to the distance "E" between the bottoms of the secondary staple-receiving grooves 356, 357 and the bottom surface 352' of the secondary driver base portion 352. See FIG. 15. Also in this embodiment, the distance "F" between the bottoms of the second staple-receiving grooves 376 and 378 and the bottom surface 373 of the third base 372 of the outside drivers 370a, 370b (FIG. 16) is less than distances "D" and "E" (FIG. 15). Because the forming distance "C" is greater than the forming distances "A" and "B", the staples 222 supported and formed by the outside drivers 370a, 370b are not compressed as much as the staples supported and formed by the inside drivers 330a, 330b. It will be understood that similar results may be attained on the opposite side of the elongated slot 310 and the cut line 600 formed in the tissue by using the same arrangements and sizes of inside drivers 330b and outside drivers 370b. In an alternative embodiment, the same effect may be achieved by altering the depths of the forming pockets 202 corresponding to the drivers 330a and 370b such that forming distance "C" is greater than the forming distances ""A" and "B". That is, the depth (distance "Z'" in FIG. 16A) of the forming pockets 202 corresponding to the outside drivers 370a. 370b may be greater than the depth (distance "Z" in FIG. 14A) of the forming pockets 202 that correspond to the inside drivers 330a, 330b.

Figure 29:
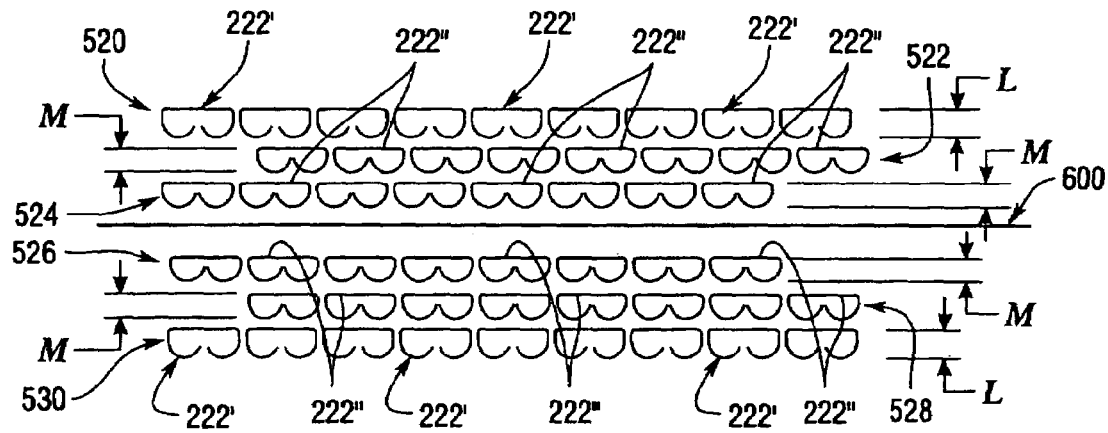
FIG. 29 is a diagrammatic representation of lines of staples installed on each side of a cut line using a surgical stapling and severing instrument according to various embodiments of the present invention.
Figure 31:
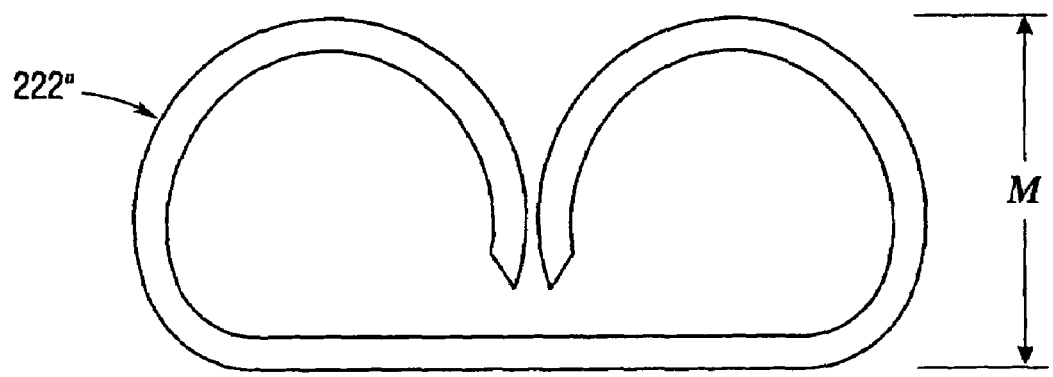
FIG. 31 depicts another staple formed by one outside driver according to various embodiments of the present invention.
Figure 30:
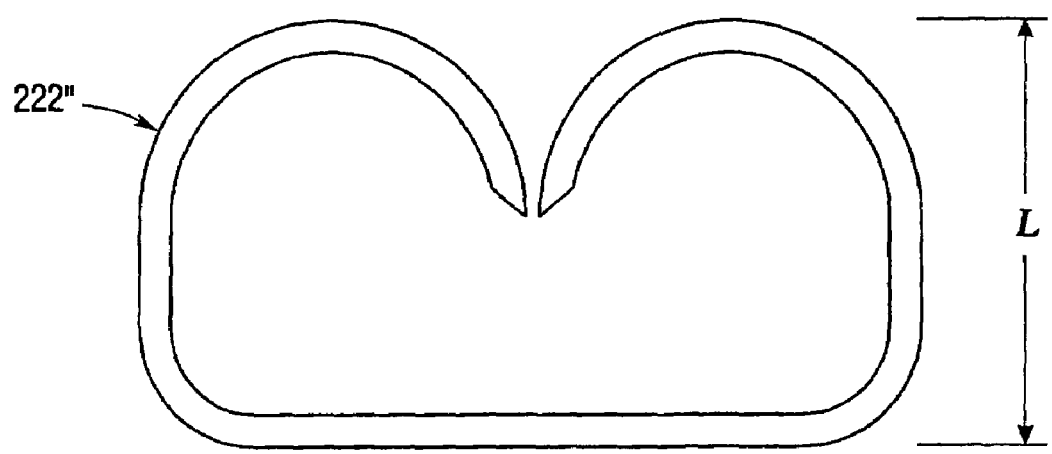
FIG. 30 depicts a staple formed by one inside driver according to various embodiments of the present invention.

FIG. 29 illustrates the rows of staples formed on each side of a cut line 600 utilizing this embodiment of the present invention wherein the forming distances "A" and "B" are equal to each other and the forming distance "C" is greater than the forming distances "A" and "B". For example, if forming distance "C" is 0.020" greater than forming distances "A" and "B", the formed height of the outside staples 222' (represented as dimension "L" in FIG. 30) in rows 520 and 530 would be 0.020 inches is greater than the formed height of the inside staples 222" (represented as dimension "M" in FIG. 31) in rows 522, 524, 526, 528.

The same result may be achieved by utilizing another embodiment of the present invention wherein the forming distances "A", "B" and "C" are essentially equal. In this embodiment, however, the height of each of the inside sled cams 410 (distance "H" in FIG. 21) is greater than the height of each of the outside sled cams 420 (distance "J" in FIG. 22). Thus, because the height "H" of the inside sled cams 410 is greater than the height "J'" of the outside sled cams 420, the inside sled cams 410 will drive the corresponding inside drivers 330a, 330b further towards the anvil than the outside sled cams 420 will drive the corresponding outside drivers 370a, 370b. Such driving action will cause the staples supported by the inside drivers 330a, 330b to be compressed to a greater extent than those staples supported by the outside drivers 370a, 370b. For example, if distance "H" is 0.020 inches greater than distance "J", the formed height of staples 222' in lines 520, 530 would be 0.020" greater than the formed height of staples 222" in lines 522, 524, 526, 528.

Figure 32:
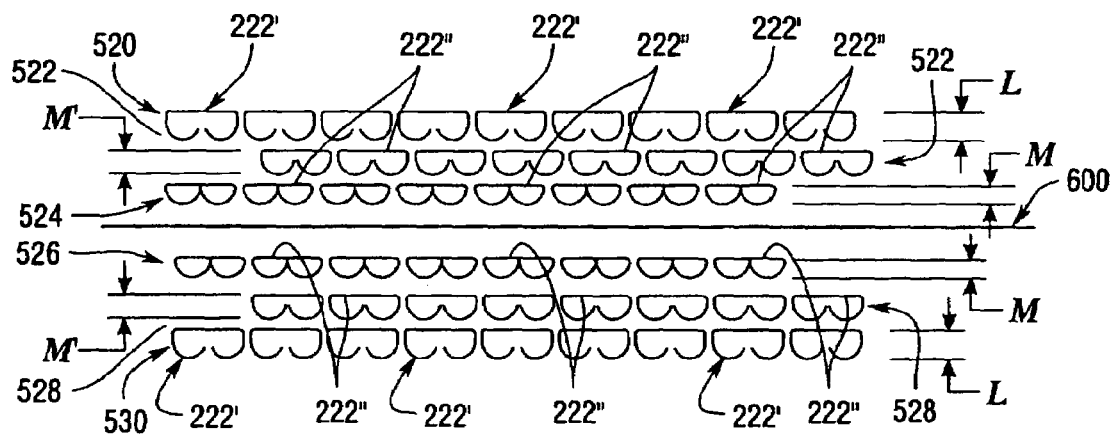
FIG. 32 is a diagrammatic representation of lines of staples installed on each side of a cut line using a surgical stapling and severing instrument according to various embodiments of the present invention.

When employing yet another embodiment of the present invention, the outside rows 520, 530 of staples 222' and the inside rows 522, 528 of staples 222" may be formed with heights that are greater than the formed heights of the staples 222" in the inside rows 524, 526. See FIG. 32. This result is achieved by making the forming distances "C" greater than the forming distance "A" and making forming distance "A" greater than secondary forming distance "B".

Figure 33:
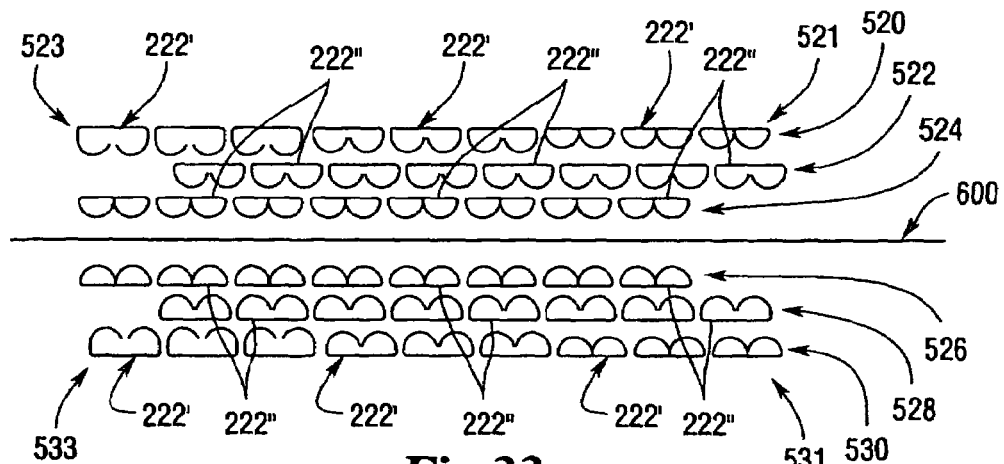
FIG. 33 is a diagrammatic representation of lines of staples installed on each side of a cut line using a surgical stapling and severing instrument according to various embodiments of the present invention.
Figure 34:
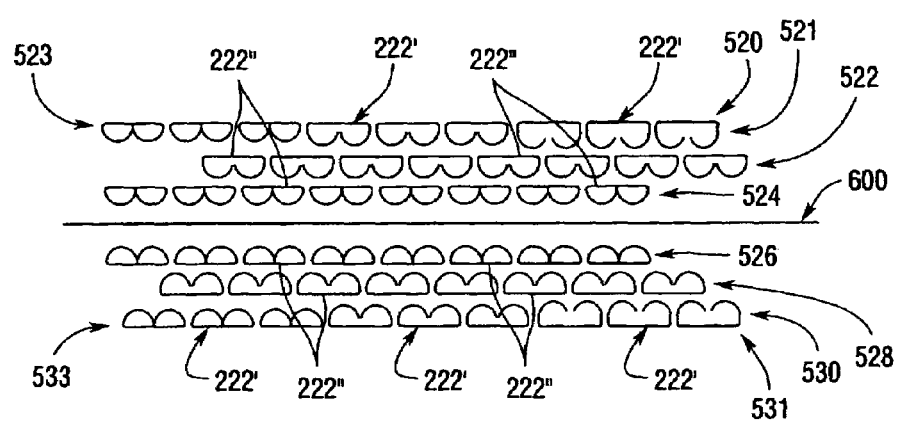
FIG. 34 is a diagrammatic representation of lines of staples installed on each side of a cut line using a surgical stapling and severing instrument according to various embodiments of the present invention.

Another embodiment of the present invention can be used to install staples where it is desirable for the formed heights of staples in a single row to vary. One such arrangement is depicted in FIG. 33. As can be seen in FIG. 33, the formed heights of the staples 222' in the outside rows 520, 530 increase when moving from the proximal ends 521, 531 of each row 520, 530, respectively to the distal ends 523, 533 of each row 520, 530, respectively. This effect may be accomplished by decreasing the forming distance "C" for each succeeding driver 370a, 370b. That is, the driver 370a closest the proximal end of the cartridge 300 would be sized to establish a forming distance "C" that is greater than the forming distance "C" achieved by the adjacent driver 370a and so on to achieve a condition wherein each succeeding staple 222' (moving in the direction from the proximal end to the distal end of the cartridge 300) would have larger formed heights. This result could also be attained in the staples 222" in rows 522, 524, 526, 528 by similarly altering the forming distances "A" and/or "B" attained by each driver 330a, 330b. Likewise, formed heights of the staples 222' in the outside rows 520, 530 could be made to decrease when moving from the proximal ends 521, 531 of each row 520, 530, respectively, to the distal ends 523, 533 of each row 520, 530, respectively. This result may be attained by increasing the forming distance of each succeeding driver 370a, 370b. That is, the driver 370a closest the proximal end of the cartridge 300 would have a forming distance "C" that is less than the forming distance "C" of the adjacent driver 370a and so on to achieve a condition wherein each succeeding staple 222' (moving in the direction from the proximal end to the distal end of the cartridge) would have smaller formed heights. See FIG. 34.

Figure 35:
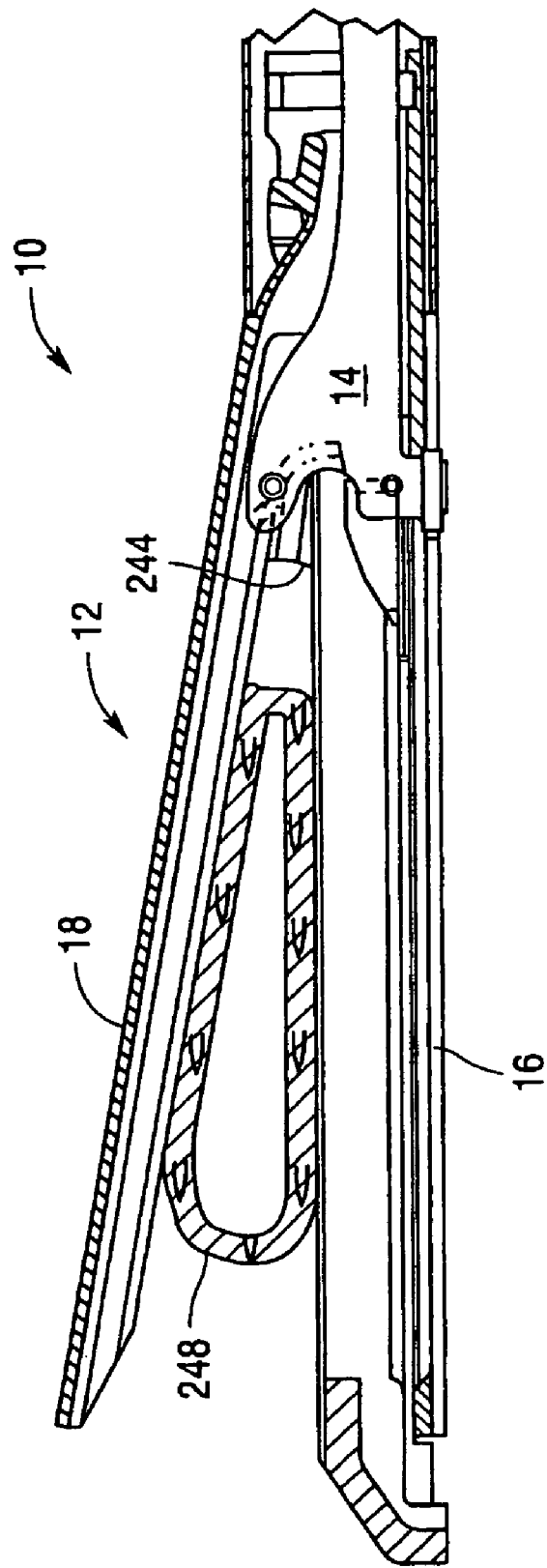
FIG. 35 is a side elevation section view of the surgical stapling and severing instrument of FIG. 1 taken along the longitudinal centerline of the end effector in a partially closed but unclamped position gripping tissue according to various embodiments of the present invention.
Figure 36:
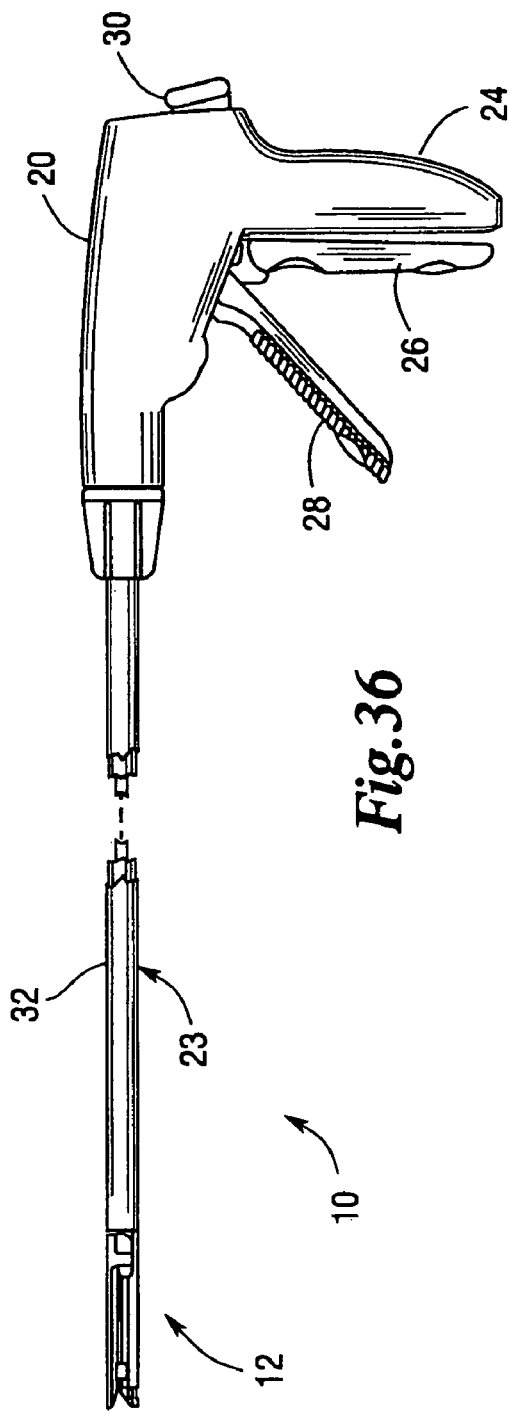
FIG. 36 depicts a partially cut away side elevational view of the surgical stapling and severing instrument of FIG. 1 in the closed or clamped position according to various embodiments of the present invention.
Figure 37:
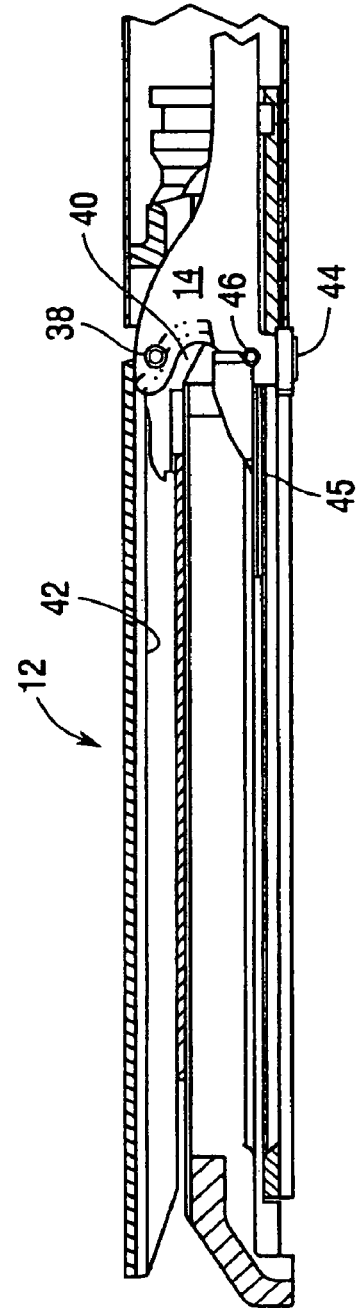
FIG. 37 depicts a side elevation view of the surgical stapling and severing instrument of FIG. 1 in the closed or clamped position with tissue properly compressed according to various embodiments of the present invention.

In use, the surgical stapling and severing instrument 10 is used as depicted in FIGS. 1-2 and 35-41. In FIGS. 1-2, the instrument 10 is in its start position, having had an unfired, fully loaded staple cartridge 300 snap-fitted into the distal end of the elongate channel 16. Both triggers 26, 28 are forward and the end effector 12 is open, such as would be typical after inserting the end effector 12 through a trocar or other opening into a body cavity. The instrument 10 is then manipulated by the clinician such that tissue 248 to be stapled and severed is positioned between the staple cartridge 300 and the anvil 18, as depicted in FIG. 35. With reference to FIGS. 36 and 37, the clinician then moves the closure trigger 26 proximally until positioned directly adjacent to the pistol grip 24, locking the handle portion 20 into the closed and clamped position. The retracted firing bar 14 in the end effector 12 does not impede the selective opening and closing of the end effector 12, but rather resides within the anvil pocket 40. With the anvil 18 closed and clamped, the E-beam firing bar 14 is aligned for firing through the end effector 12. In particular, the upper pin 38 is aligned with the anvil slot 42 and the elongate channel 16 is affirmatively engaged about the channel slot 45 by the middle pin 46 and the firing bar cap 44.

Figure 38:
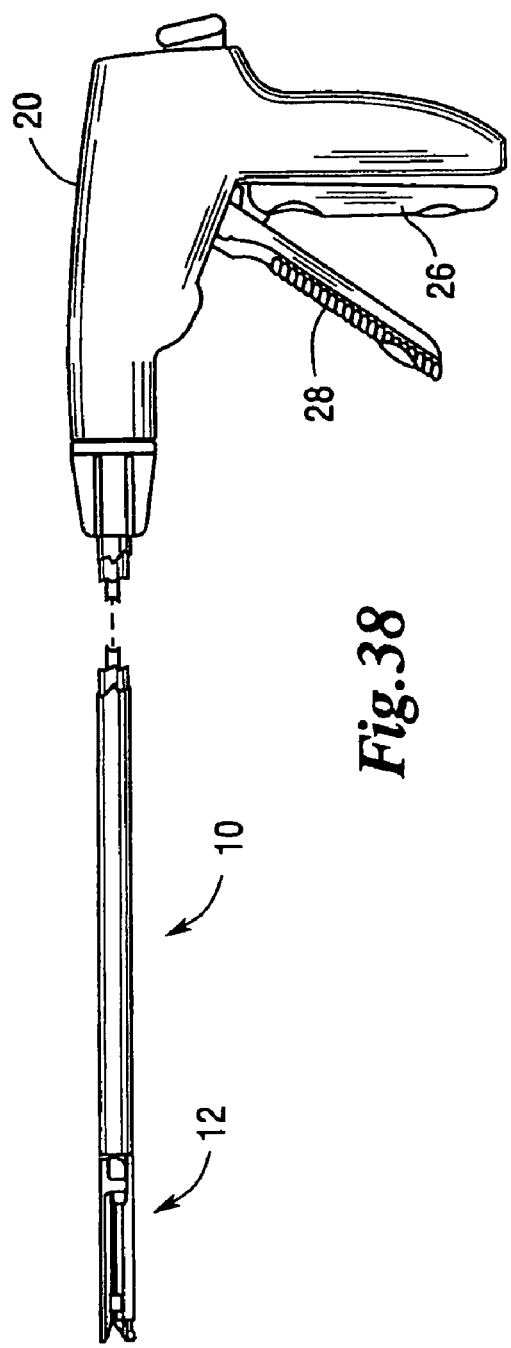
FIG. 38 depicts a view in centerline section of the distal end of the surgical stapling and severing instrument of FIG. 1 in a partially fired position according to various embodiments of the present invention.
Figure 39:
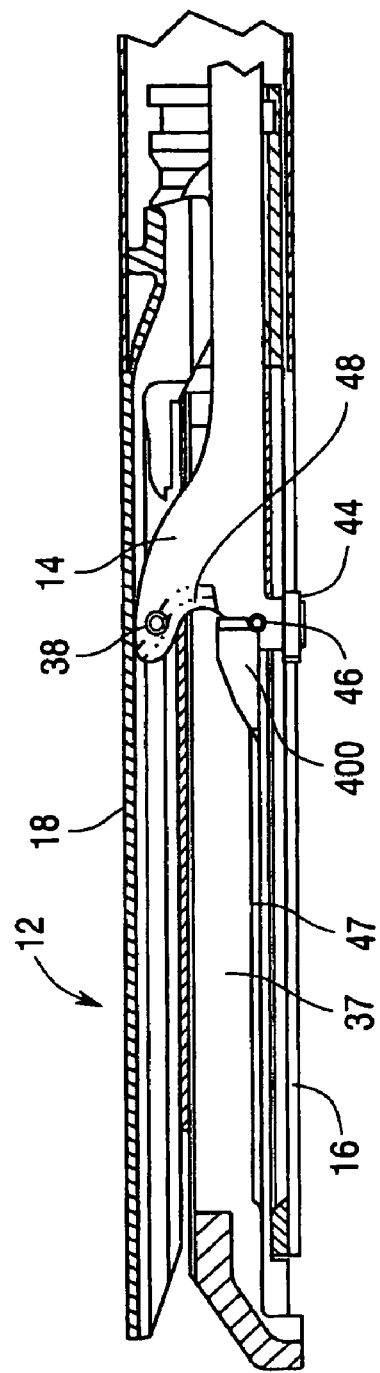
FIG. 39 depicts a partially cut away side elevation view of the surgical stapling and severing instrument of FIG. 1 in a partially fired position according to various embodiments of the present invention.

With reference to FIGS. 38 and 39, after tissue clamping has occurred, the clinician moves the firing trigger 28 proximally causing the firing bar 14 to move distally into the end effector 12. In particular, the middle pin 46 enters the staple cartridge 300 through the firing drive slot 47 to affect the firing of the staples 222 (not shown in FIGS. 38 and 39) via wedge sled 400 toward the anvil 18. The lowermost pin, or firing bar cap 44, cooperates with the middle pin 46 to slidingly position cutting edge 48 of the firing bar 14 to sever tissue. The two pins 44, 46 also position the upper pin 38 of the firing bar 14 within longitudinal anvil slot 42 of the anvil 18, affirmatively maintaining the spacing between the anvil 18 and the elongate channel 16 throughout its distal firing movement.

Figure 40:
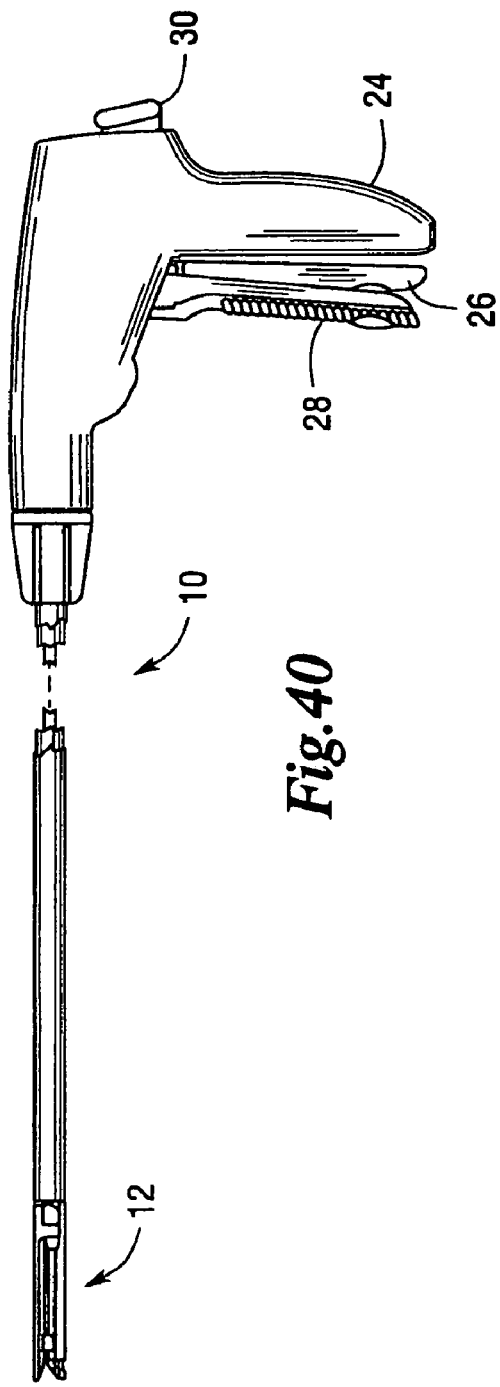
FIG. 40 depicts a view in centerline section of the distal end of the surgical stapling and severing instrument of FIG. 1 in a fully fired position according to various embodiments of the present invention.
Figure 41:
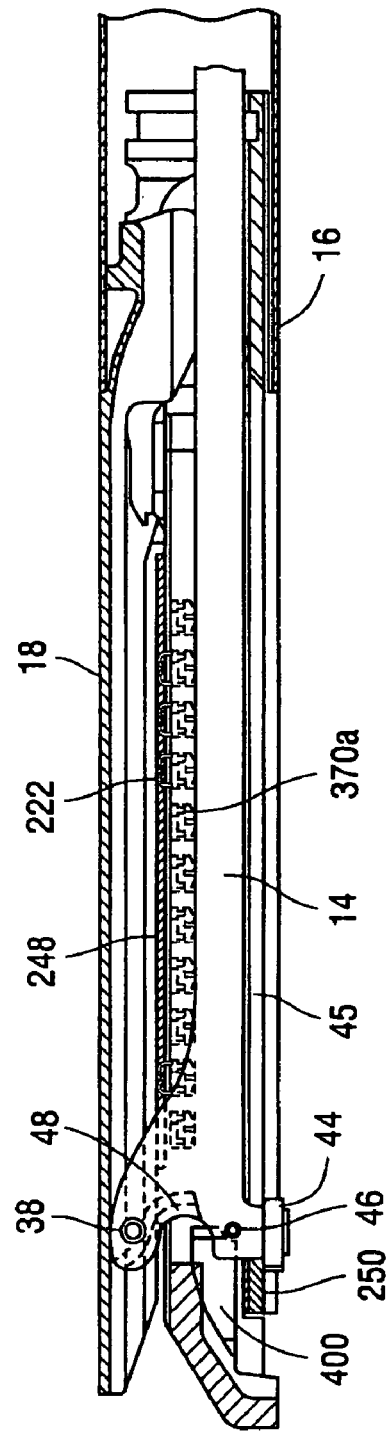
FIG. 41 is a partially cut-away side elevational view of the surgical stapling and severing instrument of FIG. 1 in a full fired position according to various embodiments of the present invention.

With reference to FIGS. 40 and 41, the clinician continues moving the firing trigger 28 until brought proximal to the closure trigger 26 and pistol grip 24. Thereby, all of the ends of the staples 222 are bent over as a result of their engagement with the anvil 18. The firing bar cap 44 is arrested against a firing bar stop 250 projecting toward the distal end of the channel slot 45. The cutting edge 48 has traversed completely through the tissue. The process is complete by releasing the firing trigger 28 and by then depressing the release button 30 while simultaneously squeezing the closure trigger 26 to open the end effector 12.

Figure 42:
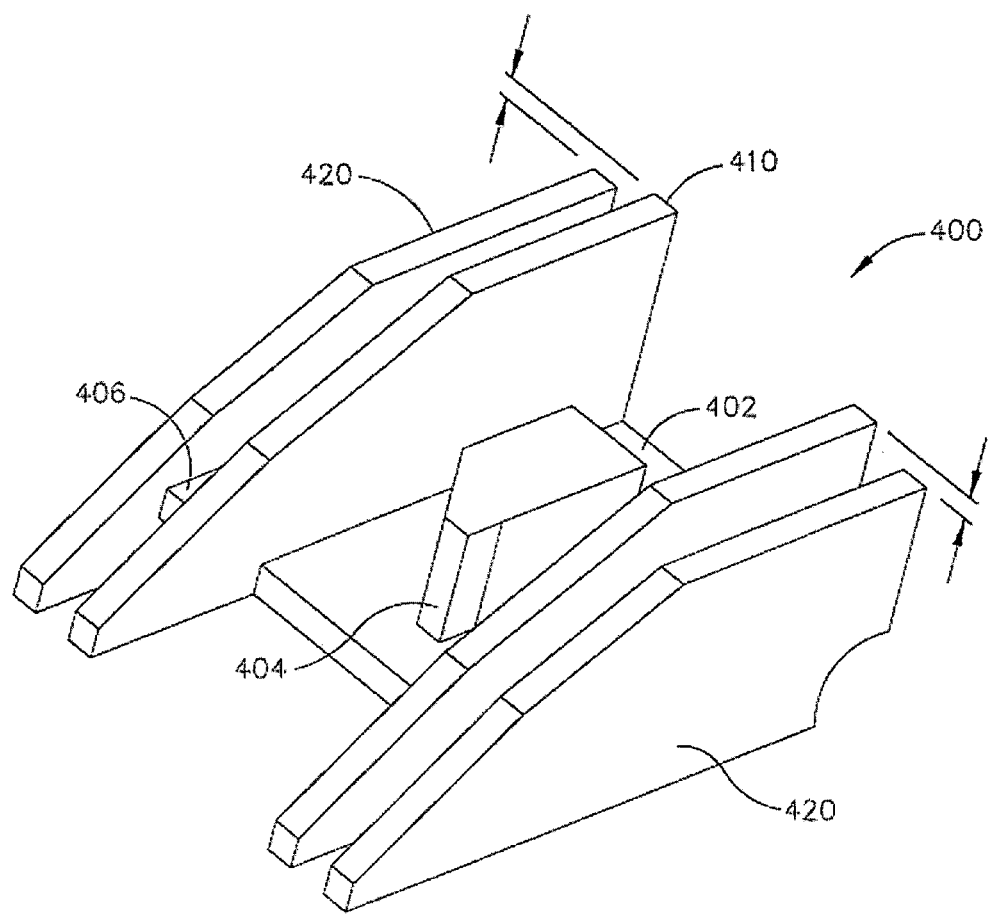
FIGS. 42-44 depict aspects of an end effector having a sled with multiple sled cams where one sled cam is taller than another according to various embodiments of the present invention.
Figure 43:
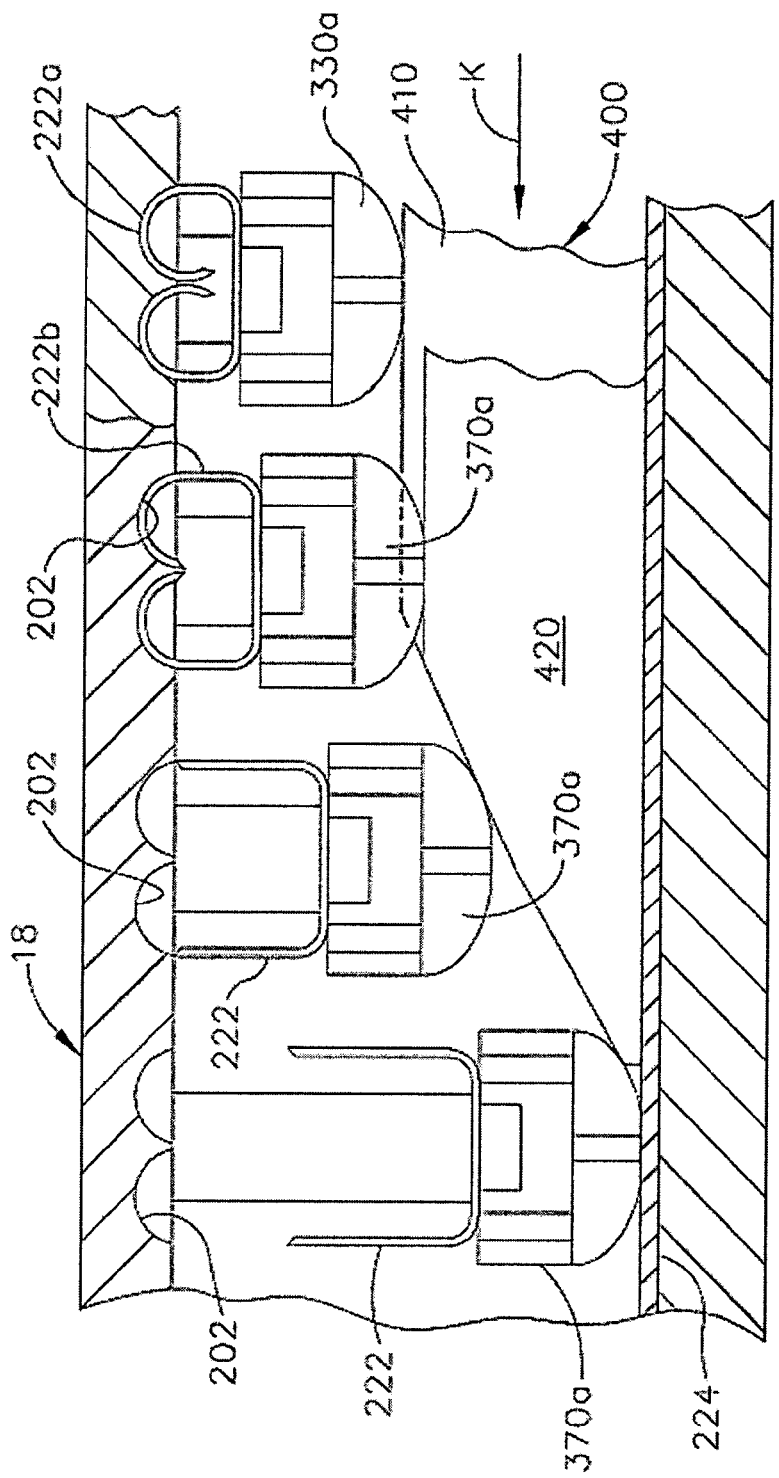

FIGS. 42-43 show the inside and outside sled cams 410, 420 of the sled 400 having different heights so that the staples, when formed, may have different formed heights. In particular, as shown in FIG. 42 the outside sled cam 420 may be shorter than the inside sled cam 410. That way, the outside staples may have a greater formed height than the inside staples. FIG. 42 is a perspective view of the sled 400 with the different heights for the inside and outside sled cams 410, 420. FIG. 43 is a side view of the end effector 12 showing various stages of driving the staples 222 with a sled 400 having different heights for the inside and outside sled cams 410, 420. As can be seen in FIG. 43, the formed staple 222b may have a greater formed height than the formed staple 222a because the staple 222b was driven by the outside cam sled 420 and the staple 222a was driven by the taller inside cam sled 410.

Figure 44:
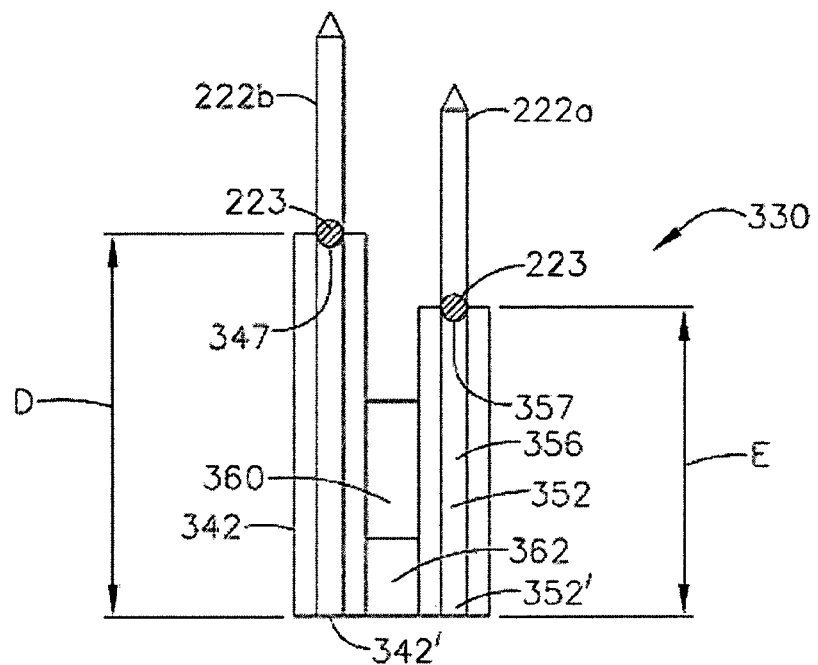

In another embodiment, as shown in FIG. 44, the heights of the driver portions 342, 352 of a double driver 330 may vary so that the staples, when formed, may have different heights. In particular, as shown in FIG. 44, the secondary driver portion 352 may be shorter (having height "E") than the primary driver portion 342 (having height "D"). That way, the staple 222a driven by the secondary driver portion 352 may have a greater formed height than the staple 222b driven by the primary driver portion 342. In various embodiments, some or all of the inside double drivers 330 could have primary and secondary driver portions 342 of different heights. Further, the heights differential need not be all the same. Different inside double drivers 330 could have different height differentials.

In addition, the height of the primary and secondary driver portions 342, 352 may be the same as or different from the height of the driver portions 372 of the outside staple drivers 370. That is, in various embodiments, the driver height of the outside staple driver portion 372 may be (1) different from the height of both driver portions 342, 352 of the inside double driver 330 when the driver portions 342, 352 are the same height, (2) different from the height of both driver portions 342, 352 when they are different heights, or (3) the same as the height for one of the driver portions 342, 352 when the driver portions 342, 352 have different heights. Also, the heights of the driver portions 372 of the outside staple drivers 370 need not be all the same. Different outside staple drivers 370 could have different heights.

Figure 45:
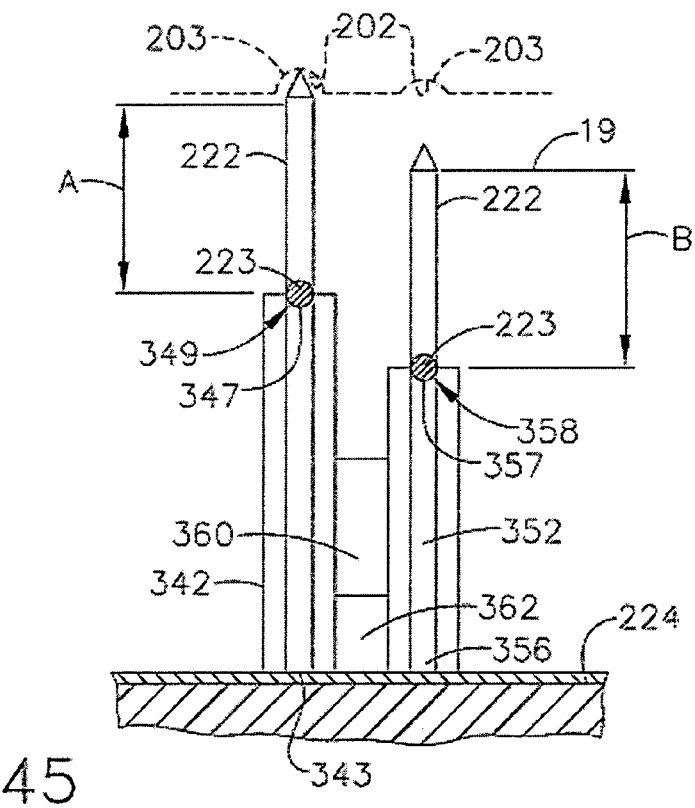
FIG. 45 depicts aspects of an end effector with staple forming pockets having varying depths according to various embodiments of the present invention.

FIG. 45 shows an embodiment having different height drivers (e.g., the primary driver portion 342 taller than the secondary driver portion 352) and with different depth anvil pockets 202. Varying the depth of the anvil pockets 202 can also affect the height of the formed staples. All things being equal, deeper pockets should result in longer formed staples. In the illustrated embodiment, the pockets 202 corresponding to the primary driver portion 342 are deeper than the pockets 202 corresponding to the secondary driver portion 352. Some or all of the pockets 202 for each staple row 500-510 could be deeper. Also, the depth differentials need not be the same. A multitude of different depths could be used in a single row 500-510 or across rows 500-510.

Figure 46:
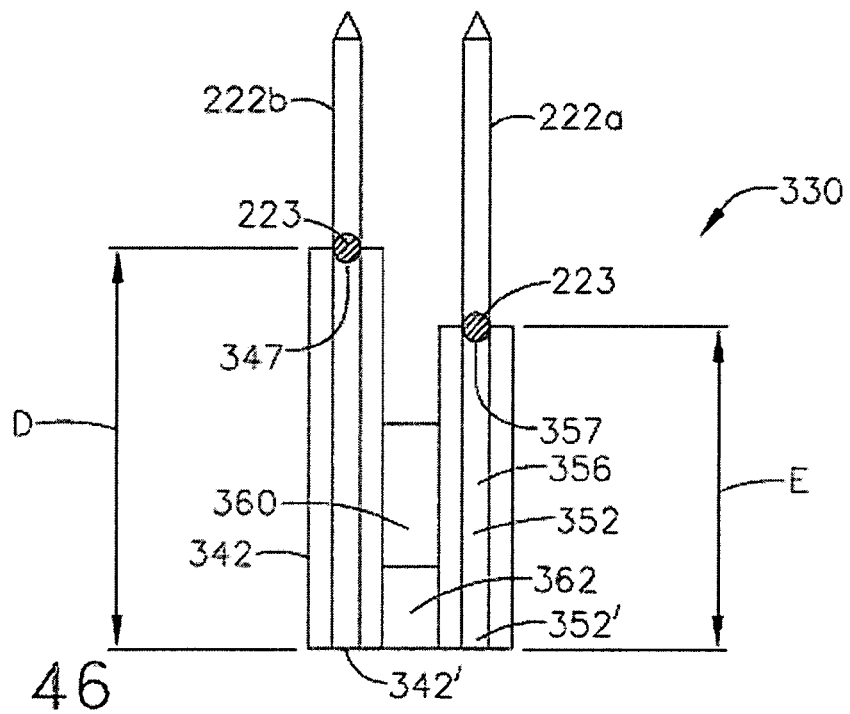
FIGS. 46-47 depict a double staple driver having staples of different pre-formation lengths according to various embodiments of the present invention.
Figure 47:
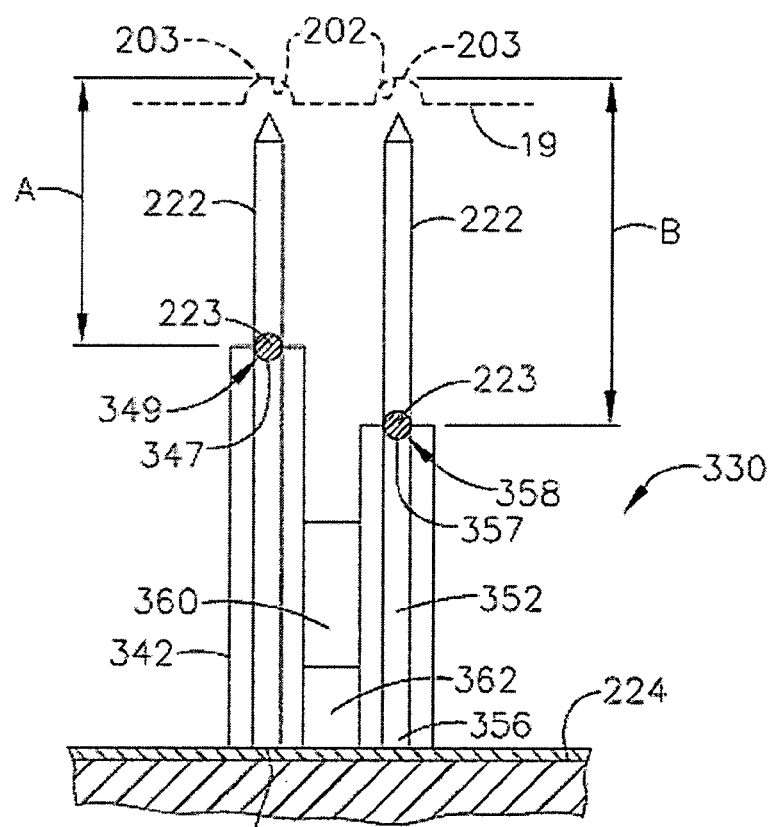

In addition, as shown in FIG. 46, staples 222 with differing pre-formation prong heights ("P") may be used. In the illustrated embodiment, the longer staple 222a is used with the shorter, secondary driver portion 352 of an inside double driver 330 in comparison with staple 222b driven by the primary driver portion 342. The pre-formation staple prong lengths may vary within a staple row 500-510 or across staple rows. That is, for example, all of the staples in the inside rows 504-506 could have the same pre-formation prong length x, all of the staples in the intermediate rows 502, 508 could be longer (e.g., a length 1.10x), and all of the staples in the outer rows 500, 510 could be still longer (e.g., a length of 1.20x). As shown in FIG. 47, the anvil pockets 202 could have the same depth. In other embodiments, varying anvil pocket depths could be used.

Figure 48:
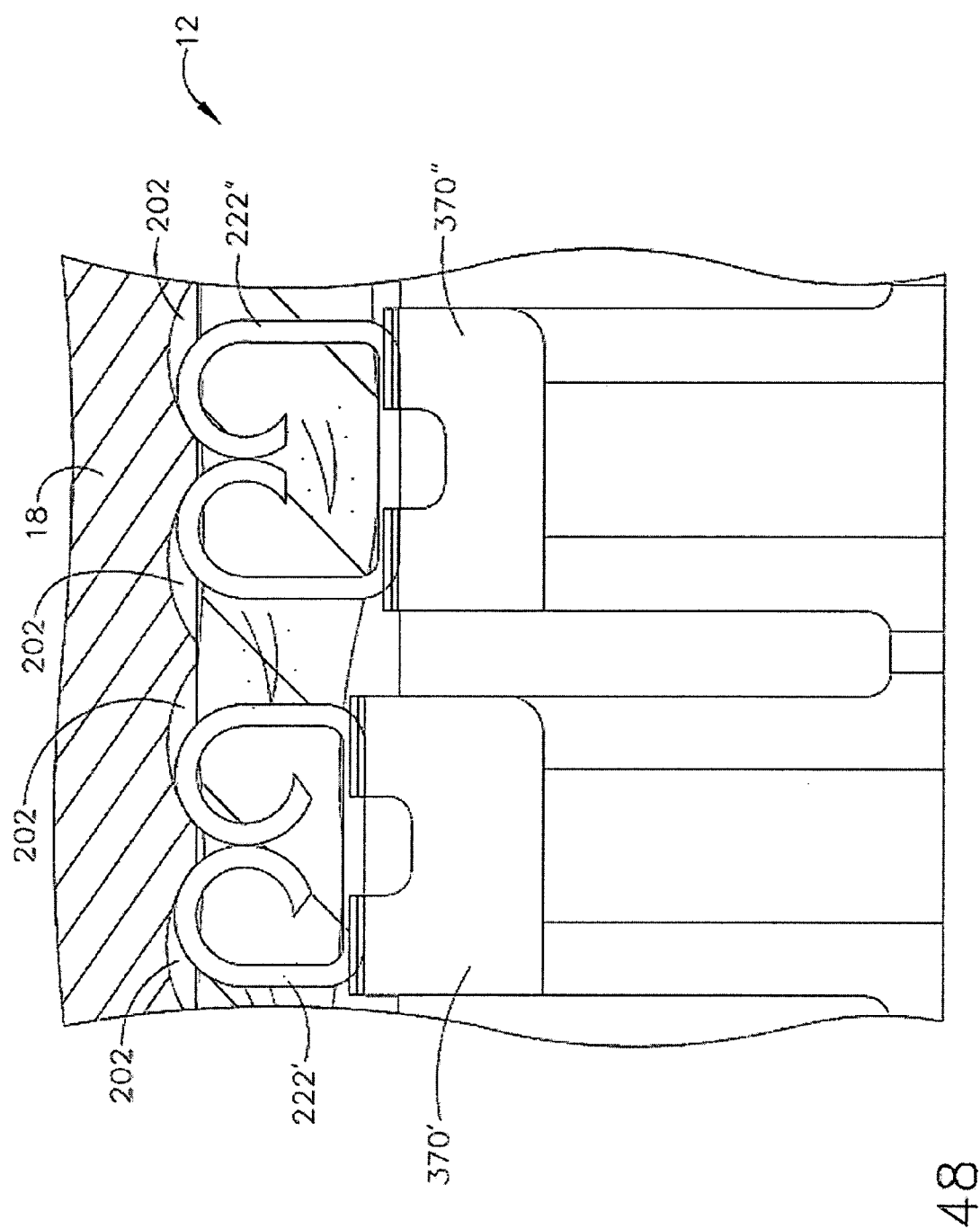
FIG. 48 depicts a side-view of an end effector having a double staple driver having different staple driver heights according to various embodiments of the present invention.

FIG. 48 is a side view of the end effector 12 in an embodiment where the outside staple drivers 370 have different heights. In particular, in the illustrated embodiment, the first staple driver 370' is taller than the second staple driver 370". In the illustrated embodiment, the staples 222 have the same pre-formation prong length and the corresponding anvil pockets 202 have the same depth. As such, the formed staple 222" formed with the second outside staple driver 370" is longer than the formed staple 222' formed with the first outside staple driver 370'.

Figure 49:
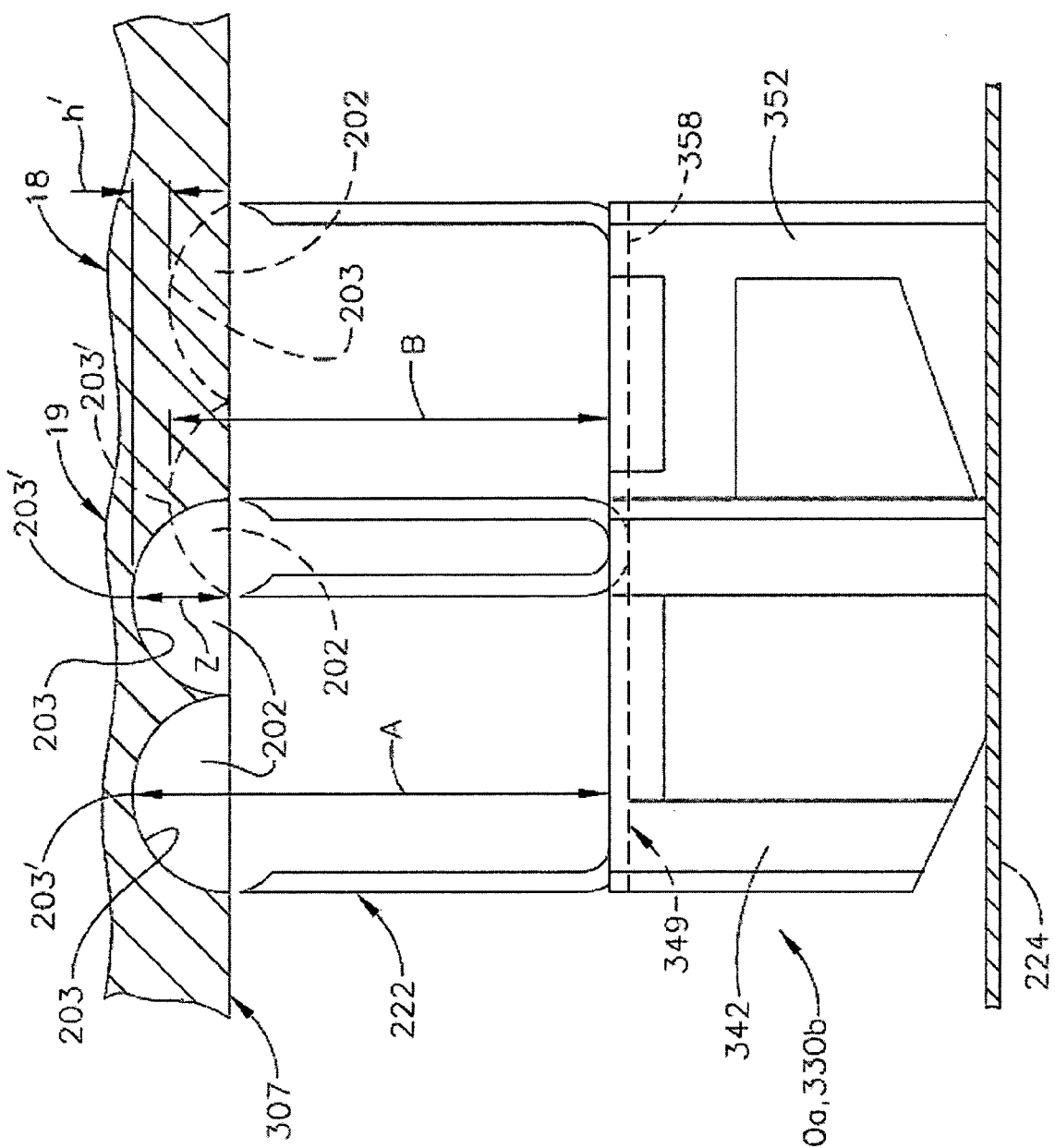
FIGS. 49-50 depict a side-view of an end effector having staple forming pockets of varying depths according to various embodiments of the present invention.
Figure 50:
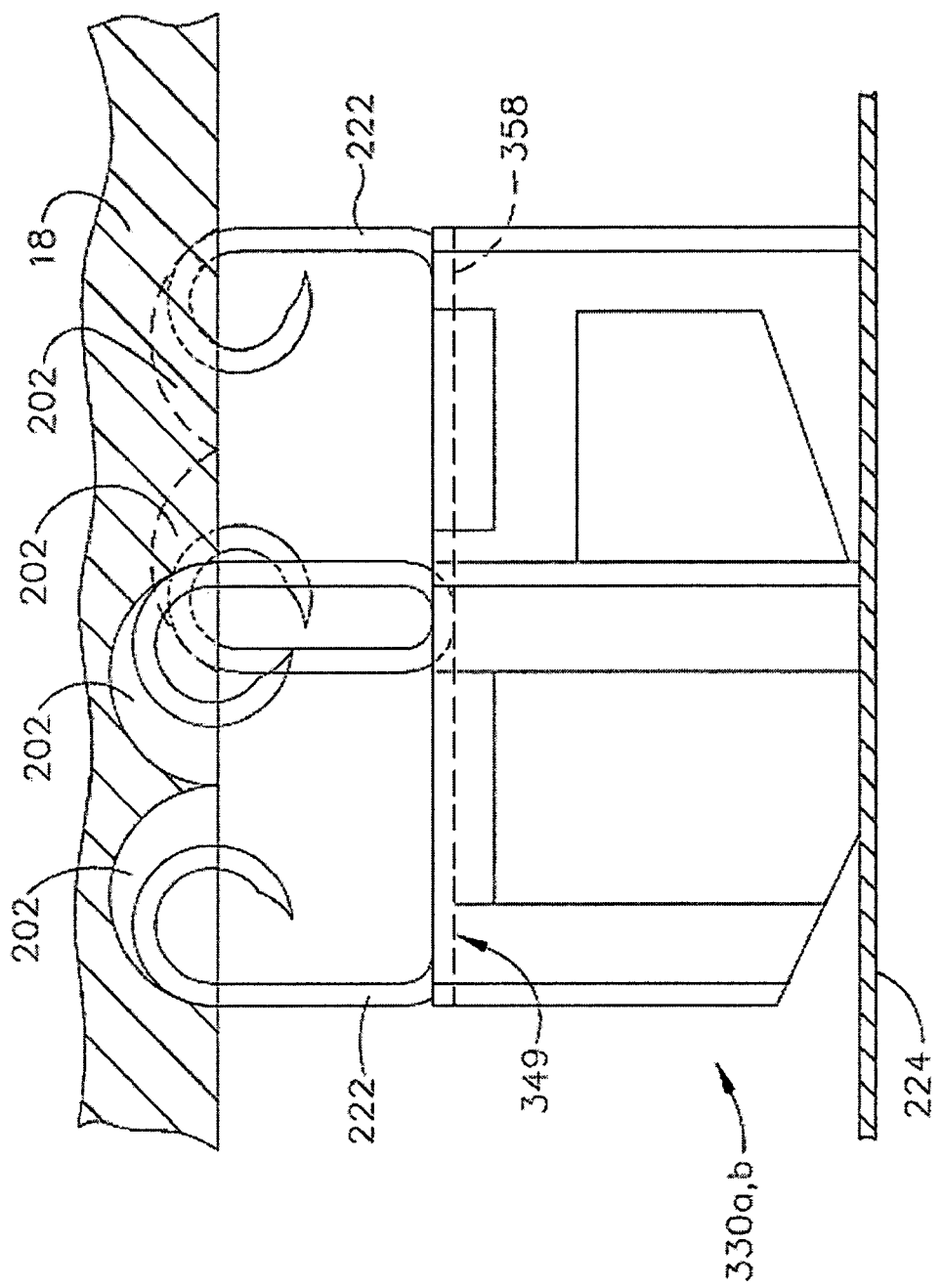

FIG. 49 is a side view of the end effector 12 where the anvil 18 has pockets 202 of different depth for the staples 222 driven by a inside double driver 330. In the illustrated embodiment, the pockets 202 corresponding to the primary driver portion 342 are deeper than the corresponding pockets 202 for the secondary driver portion 352. In this embodiment, the primary and secondary driver portions 342, 352 are the same height and the staples 222 have the same pre-formation prong length. The distance between the top of the primary driver portion 342 and the top of the corresponding anvil pockets 202 is height "A" and the corresponding height for the secondary portion 352 is height "B," where "A" is greater than "B" by a height differential "h'". This should result in longer formed staples for the primary driver portion 342, as shown in FIG. 50.

Figure 51:
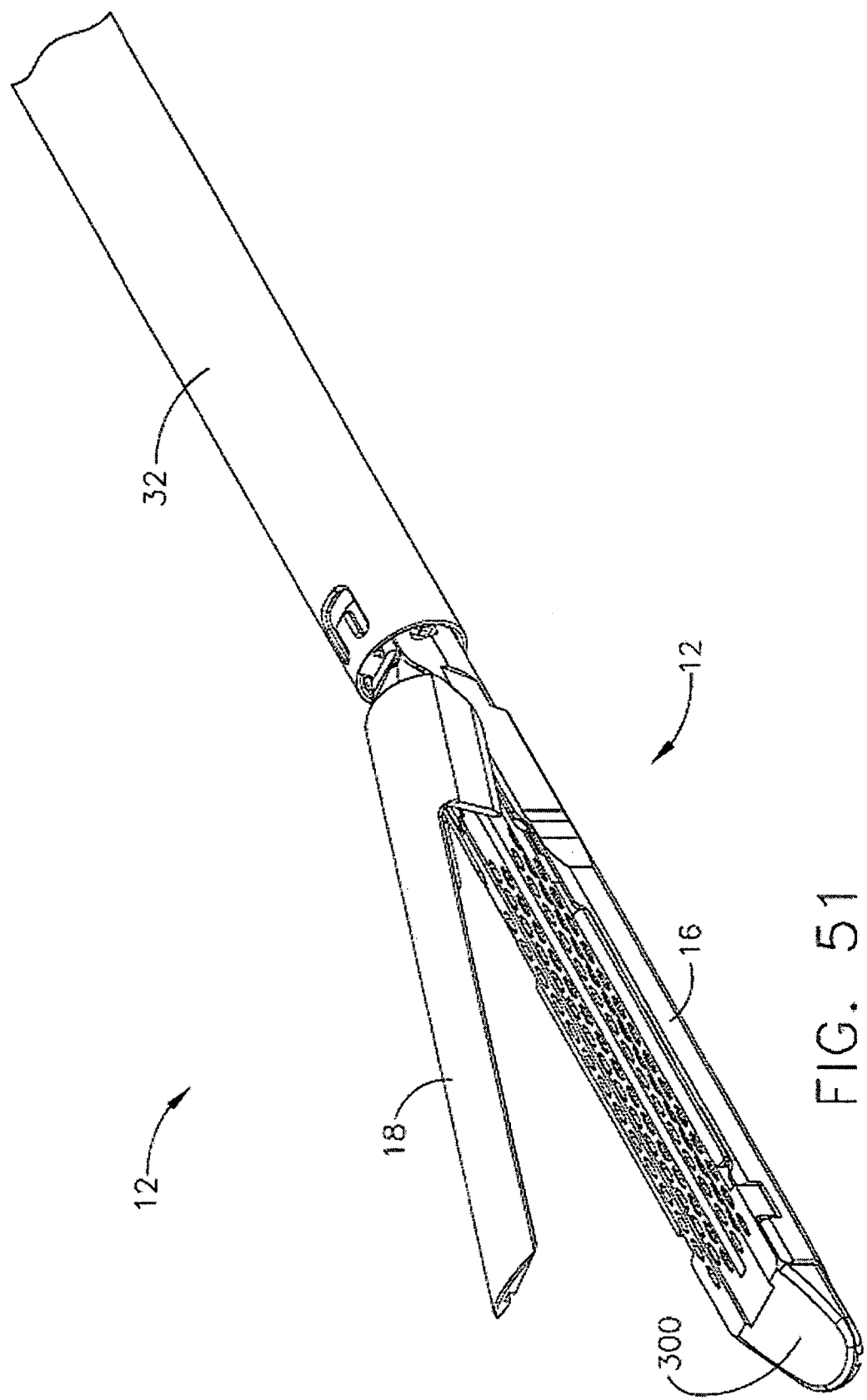
Figure 52:
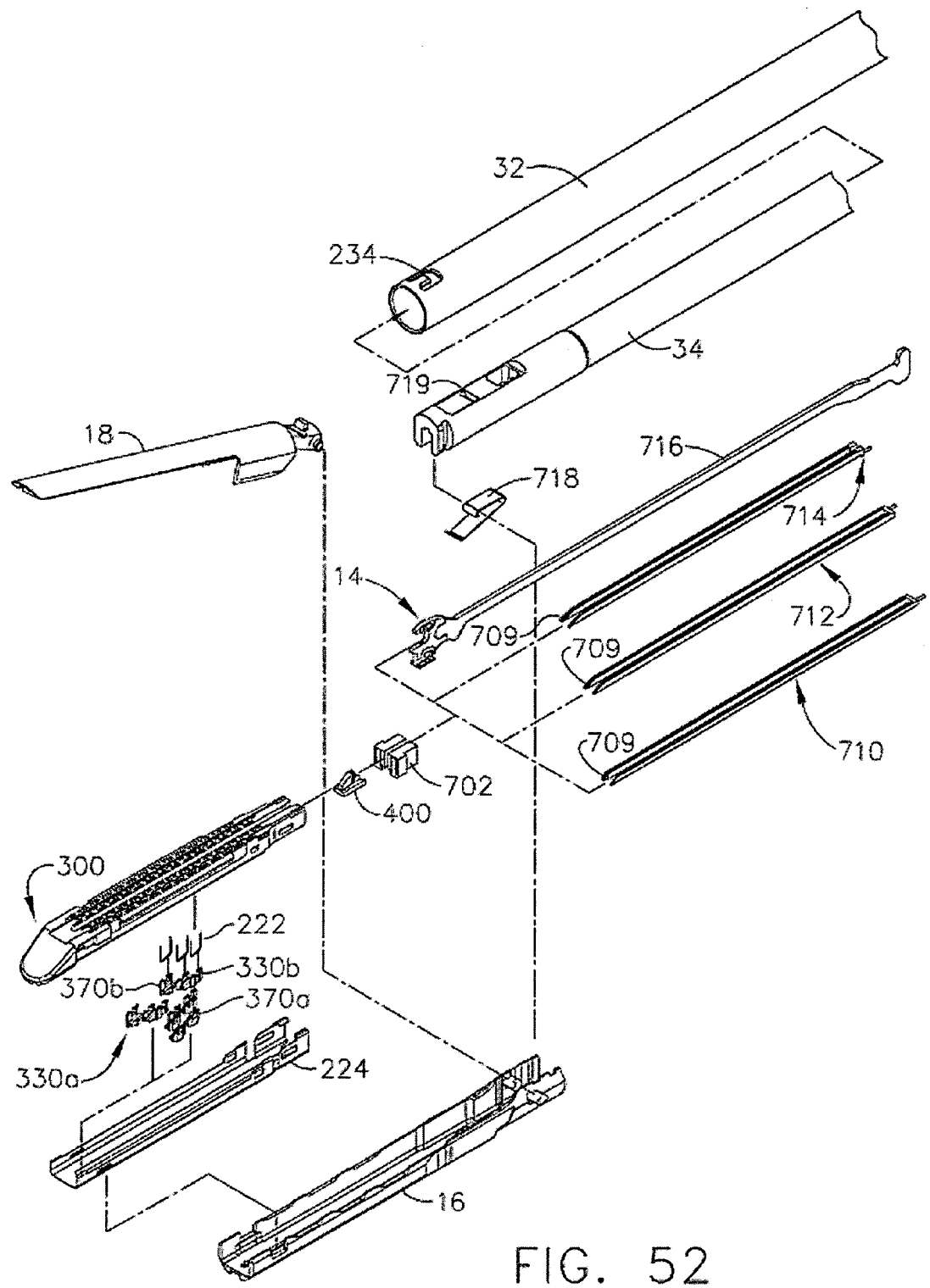
Figure 55:
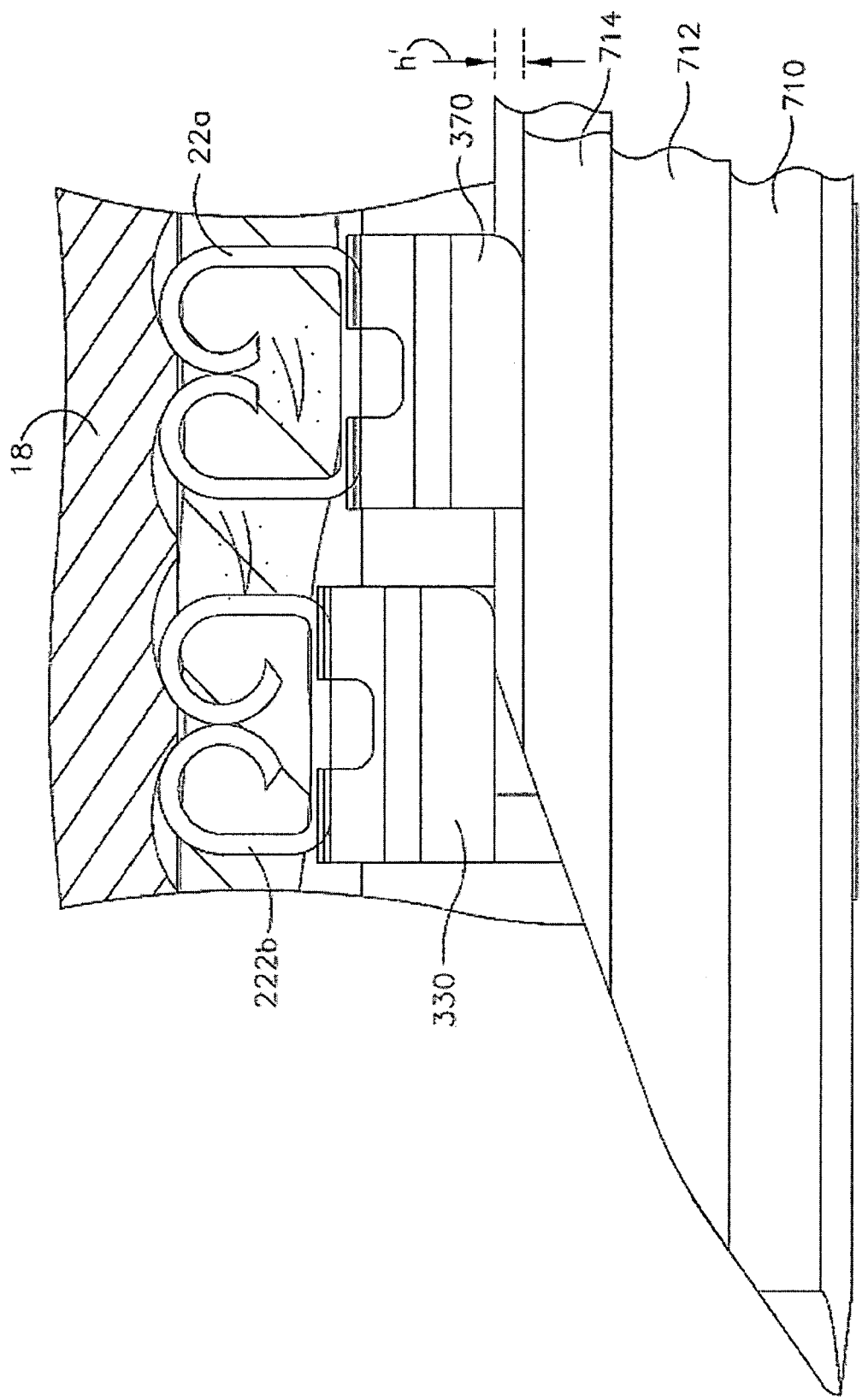
Figure 56:
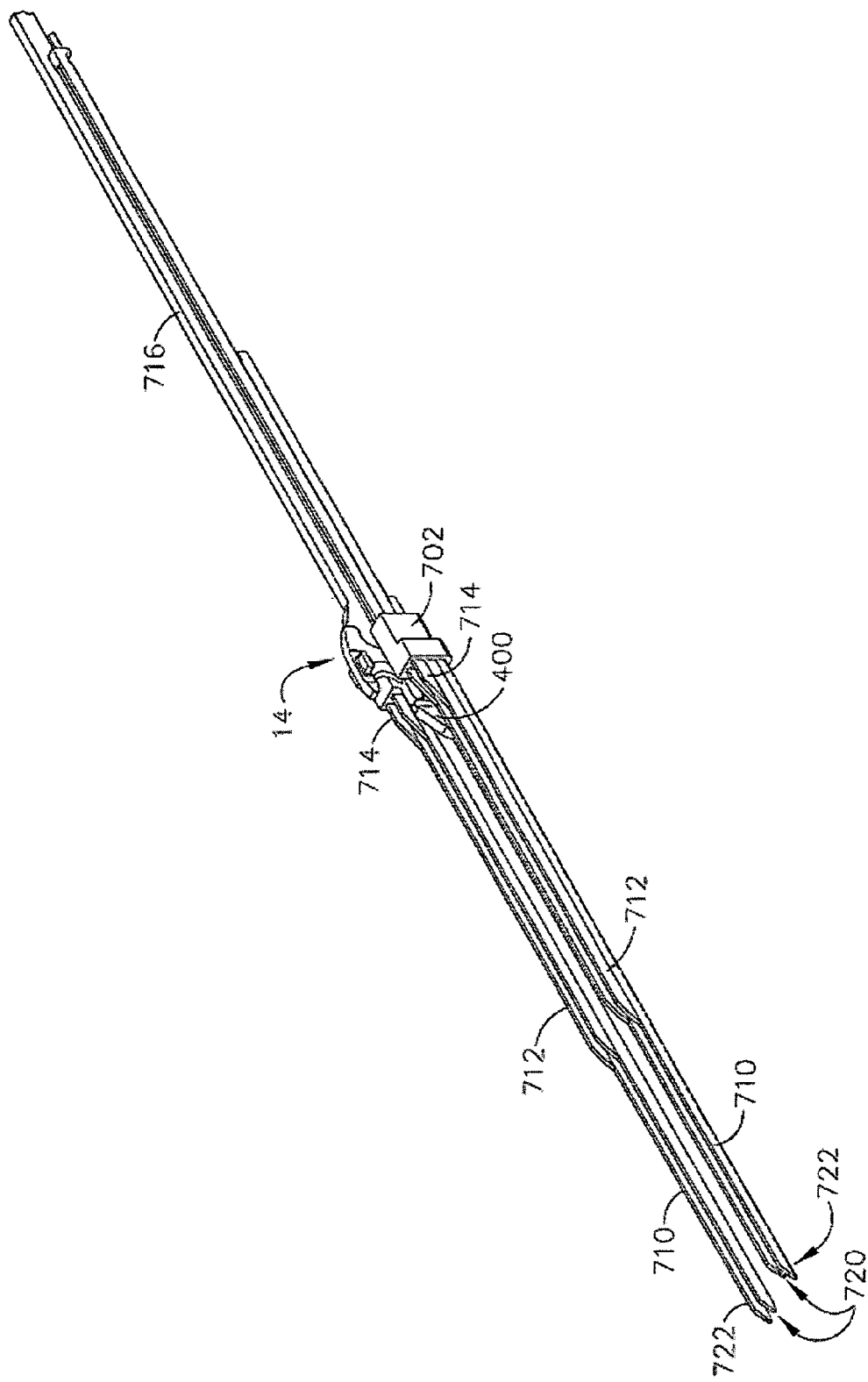
Figure 57:
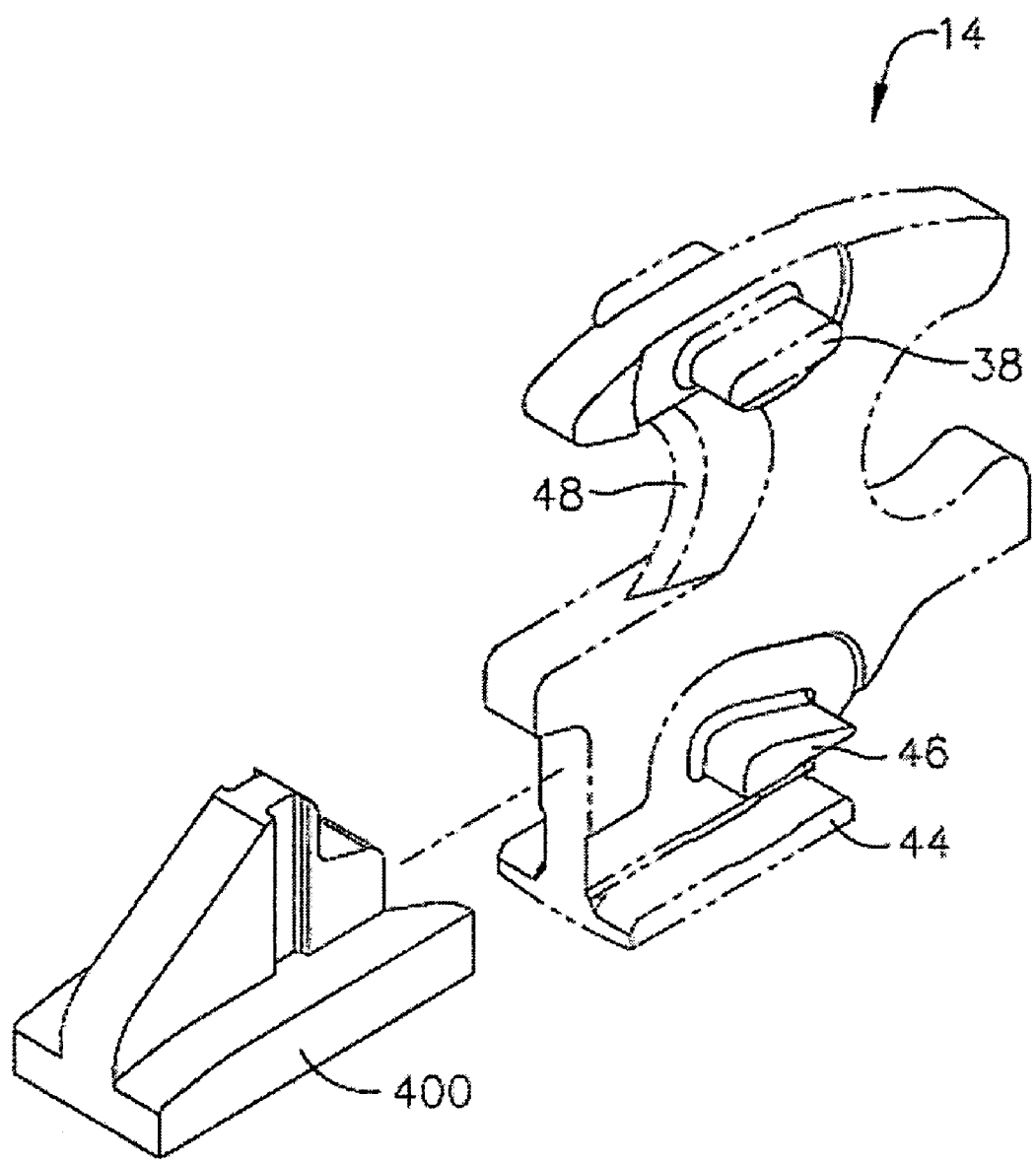

FIGS. 51 and 60 show aspects of an end effector 12 according to other embodiments that can be used to produce staples of different formed lengths. In the illustrated embodiment, the staple drivers 330, 370 are driven in stages by a plurality of actuator wedge cams 709 at the distal end of a plurality of wedge band sets 710, 712, 714. In the illustrated embodiment, each wedge band set comprise four wedge bands (shown best in FIG. 56); two 720 for actuating the inner drivers 330a,b and two 722 for actuating the outer drivers 370a,b. The wedge bands of the wedge band sets 710, 712, 714 may be actuated in serial order and may ride on top of one another in a stack to drive the staple drivers 330a,b, 370a,b (and hence the staples 222) in serial stages. For example, the wedge bands of the lowermost actuator wedge band set 710 may be fired (or actuated) first, and may partially deploy the staples 222. The middle wedge band set 712, which rides on top of the lowermost wedge band set 710 as shown in FIGS. 53-56, may be actuated next, which may have the effect of beginning to form the staples 222. Then the uppermost wedge band set 714, which rides on the middle wedge band set 712, may be actuated, which finishes the formation of the staples 222. FIG. 56 illustrates this operation. In FIG. 56, the lowermost wedge band sets 710 have been fired, the middle wedge band sets 712 have been partially fired, and the uppermost wedge band set 714 has not yet been fired. Thus, such an embodiment may comprise a plurality (in this case four) of stacked wedge band sets, each stack comprising a wedge band from the lowermost set 710, the middle set 712, and the uppermost set 714.

The firing bar 716, with the e-beam firing mechanism 14, may then be fired to cut the tissue clamped by the end effector 12. A hold down spring 718, which may be connected to the frame 34 at a crossbar 719, may engage and urge the firing bar 716 downward.

Figures 53, 54:
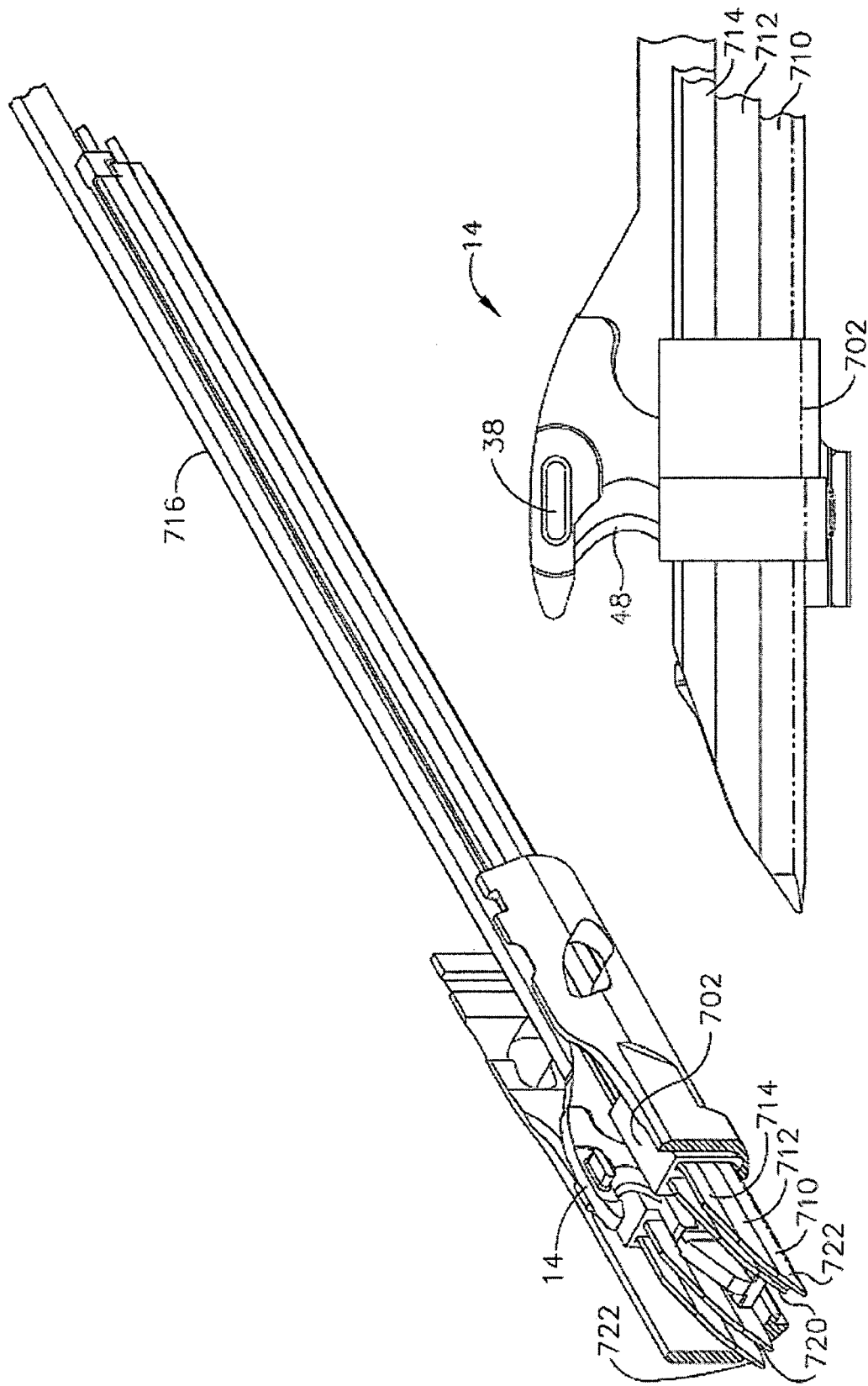
Figure 61:
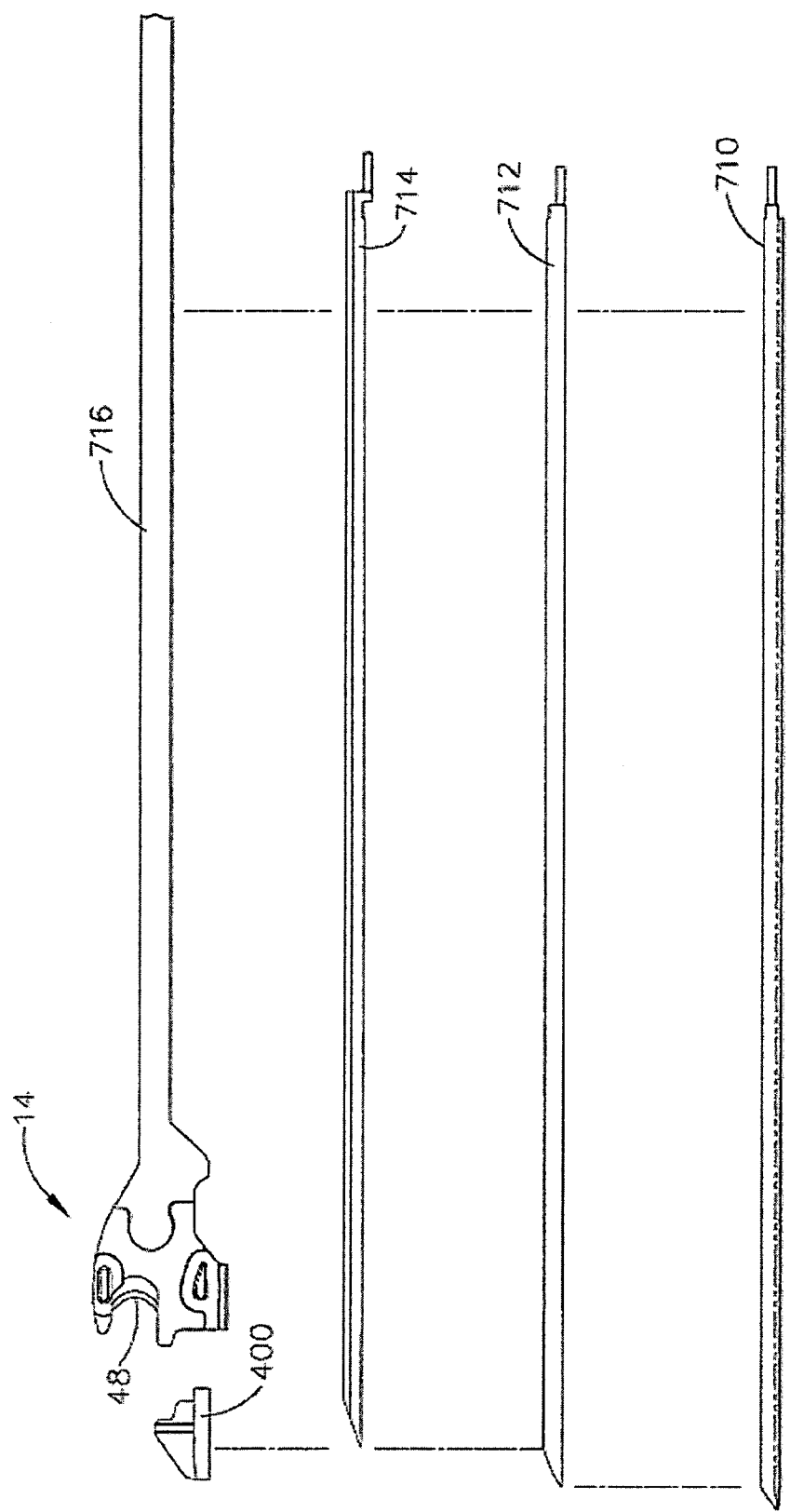

As can be seen best in FIGS. 54 and 56, the cumulative height of the wedge band stacks of inner row 720 or may be greater than the cumulative height of the wedge band stacks of the outer row 722 (by a height differential h'). That way, the outer row of staples may have a greater formed length than the inner row of formed staples, as shown in the example of FIG. 55, where the outer row staple 222a has a greater formed length than the inner row staple 222b. As shown the example of FIG. 61, according to one embodiment, the wedge bands of the lowermost and middle wedge bands sets 710, 712 may be the same height, and the height of the wedge bands for the outer row 722 of the uppermost wedge band set 714 may be less than the height of the wedge bands of the inner row 720 of the uppermost wedge band set 714 to provide the height differential for the different wedge band stacks.

The end effector 12 in such an embodiment may still comprise a sled 400, but without the sled cams 410, 420, to keep the firing mechanism 14 out of the lockout in the channel (see FIGS. 3-4 and related text).

The inner and outer wedge band stacks 720, 722 may be tightly spaced within the frame 34. Accordingly, the end effector 12 may further comprise an actuator wedge band respective guide 702 for spreading out the wedge band stacks 720, 722 when they enter the end effector 12 to align with the staple drivers 330, 370. The wedge band guide 702 may include wedge band channels for each of the inner and outer wedge band stacks 720, 722. That is, in the illustrated embodiment, the wedge band guide 702 may comprise four wedge band channels—two of the inner rows 720 and two for the outer rows 722. FIGS. 58-60 show one side of the wedge band guide 702 in more detail. As shown in FIG. 60, the wedge band channels 730, 732 may force the wedge band stacks 720, 722 outward as they enter the end effector 12. The inner wedge band channel 730 may direct the inner wedge band stack 720 so that the inner wedge band stack 720 aligns with the inner staple drivers 330 and the outer wedge band channel 732 may direct the outer row wedge band stack 722 so that the outer wedge band stack aligns with the outer staple drivers 370. In the illustrated embodiment, the channels 730, 732 are straight. In other embodiments, one or both of the channels 730, 732 may comprise curved portions.

Figure 62:
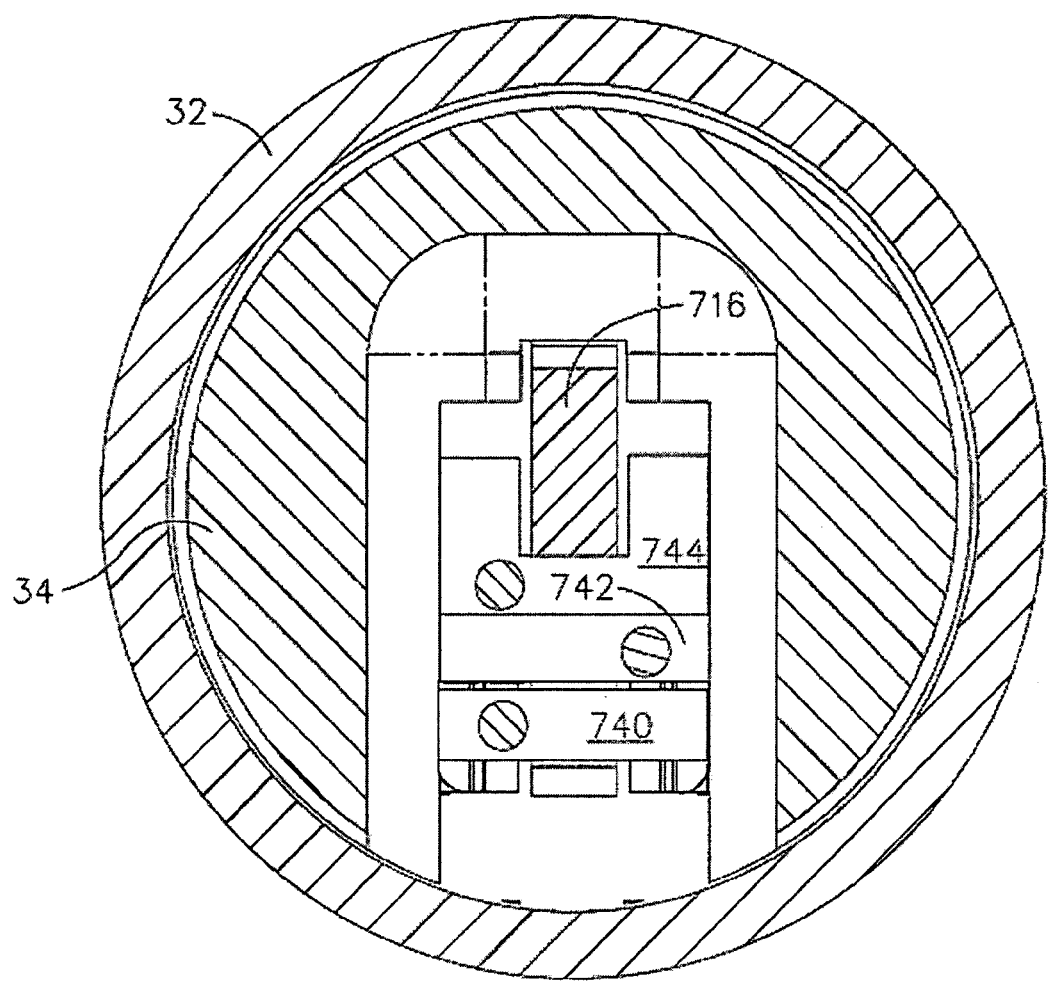
Figure 63:
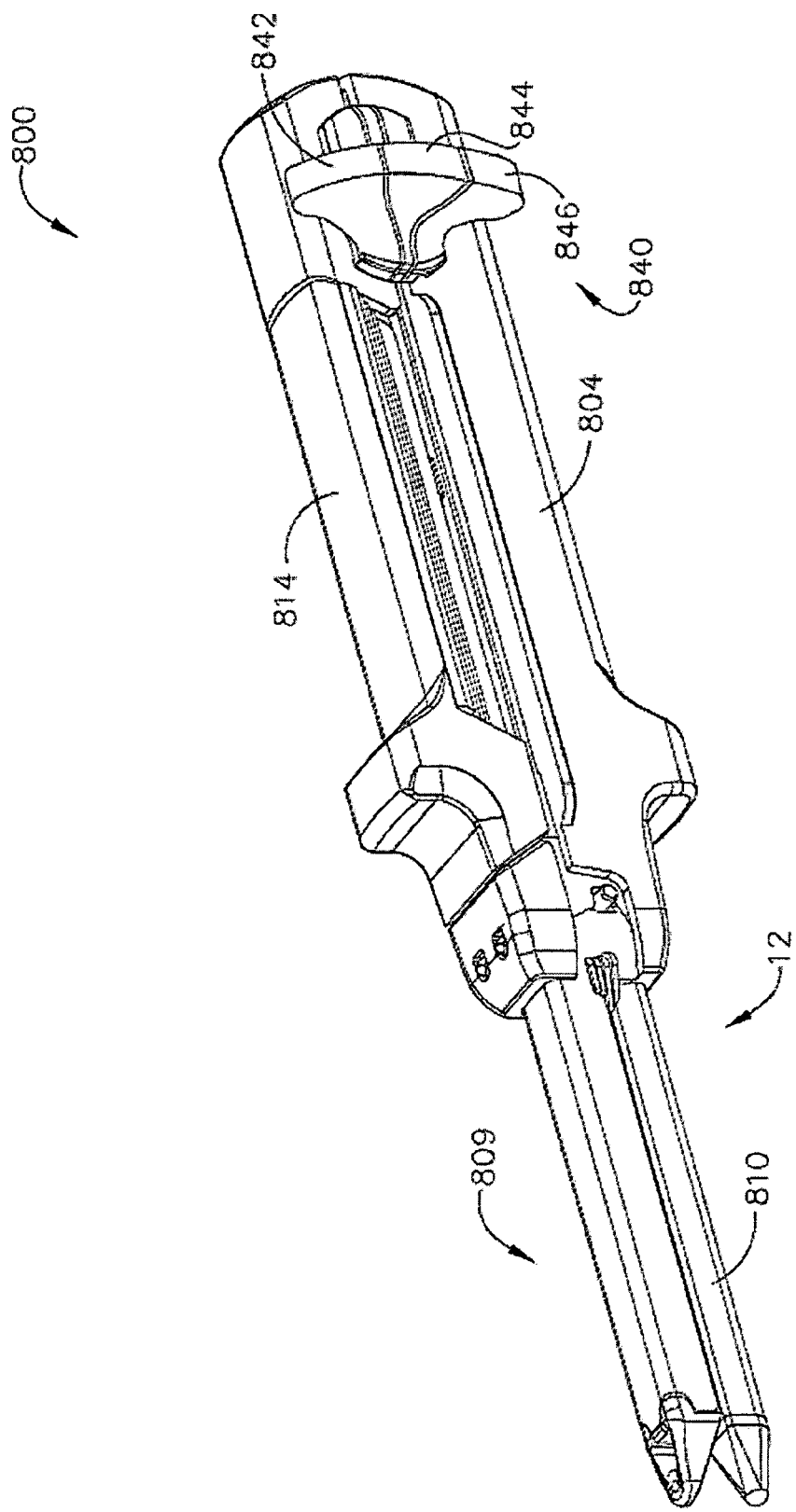
FIGS. 63-69 depict aspects of an open linear surgical stapling device according to various embodiments of the present invention.
Figure 64:
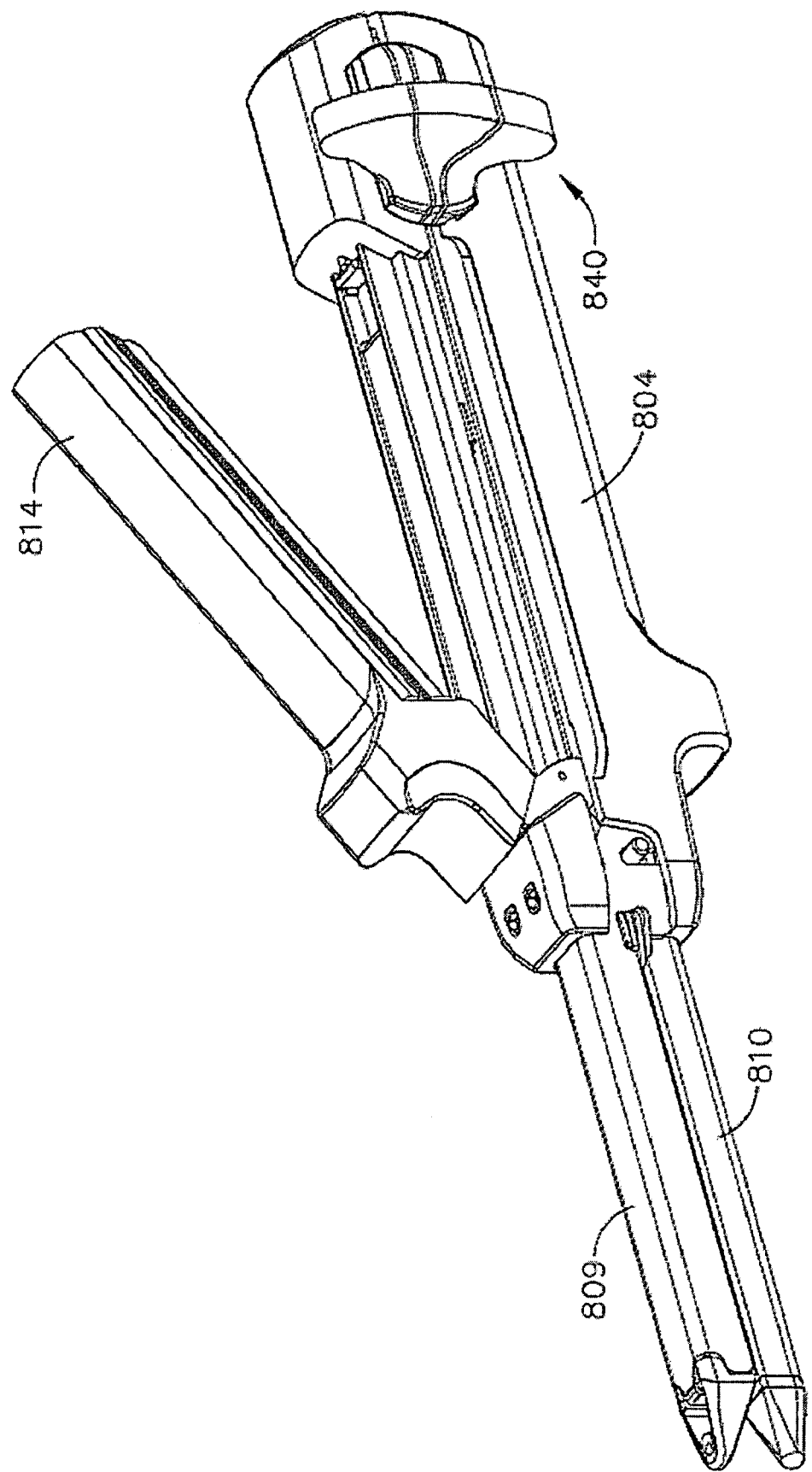
Figure 65:
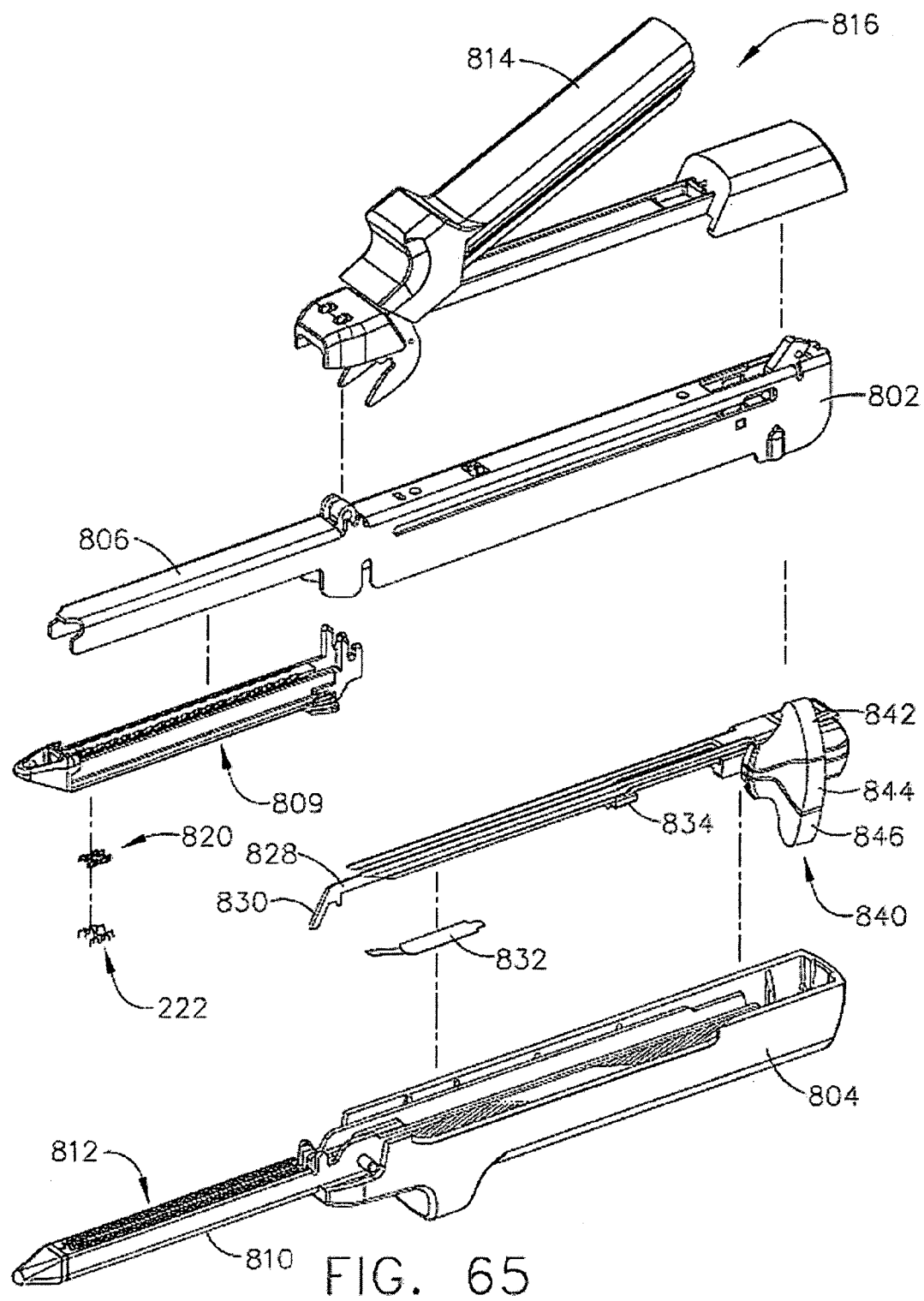

FIG. 62 is a cross-sectional view of the shaft assembly 10 according to such an embodiment. As shown in FIG. 62, each wedge band set 710-714 may have its own actuation (or firing) bar. The lowermost actuation bar 740 may actuate the wedge bands of the lowermost wedge band set 710, the middle actuation bar 742 may actuate the wedge bands of the middle wedge band set 712, and the uppermost actuation bar 744 may actuate the wedge bands of the uppermost wedge band set 714. The firing bar 716 for actuating the cutting instrument 14 may be connected to the uppermost wedge band set 714 so that the cutting instrument 14 is actuated with the uppermost (last) wedge band set 714. In other embodiments, the firing bar 716 may have its own actuation mechanism so that is may be actuated separately.

In practice, the clinician may choose (or select) to actuate less than all of the wedge band sets 710-714 before actuating the firing rod 716 to cut the tissue to thereby exercise some choice in the length of the staples to be formed. For example, in various embodiments, the clinician may select to actuate the lowermost and middle wedge band sets 710, 712—and not the uppermost wedge band set 714—before cutting.

FIGS. 63-69 illustrate an embodiment of an open linear stapling and cutting device 800 that may use multiple stacked wedge band sets to produce staples of different formed lengths. In the illustrated embodiment, the anvil 810 is below the channel 809. As such, the staples are driven down through tissue clamped in the end effector 12 as part of the stapling operation.

The device 800 may include an upper body piece 802 and a lower body piece 804. The upper body piece 802 may include a channel 806 in which the staple cartridge 809 is inserted. The anvil 810 may be connected to the lower body piece 804 and face the staple cartridge 809 so that the staples 222 can be formed against the staple forming surface 812 of the anvil 810. When the clinician is satisfied with the position of the tissue between the cartridge 809 and the anvil 810, the clinician may lock the device 800 using a clamp lever 814 of a clamp lever assembly 816 connected to the upper body piece 802.

The staple drivers 820 in the cartridge 809 may be actuated in stages using multiple staged wedge band stacks. Because the staples 222 are driven down in this embodiment, the wedge bands of the uppermost wedge band set 822 may be actuated first to partially deploy the staples 222. Next, the wedge bands of the middle wedge band set 824, which ride on the uppermost wedge band set 822, may be actuated to begin forming the staples 222. Then the wedge bands of the lowermost wedge band set 826, which ride on the middle wedge band set 824, may be actuated, which finishes the formation of the staples 222.

In the illustrated embodiment, the firing bar 828, with the knife 830 at is distal end, is connected to the lowermost wedge band set 826 and is fired with the lowermost wedge band set 826. A hold down spring 832 may engage and urge the firing bar 828 upward. A knife retainer 834 may retain the firing bar 828 with the lowermost wedge band set 826.

Figure 67:
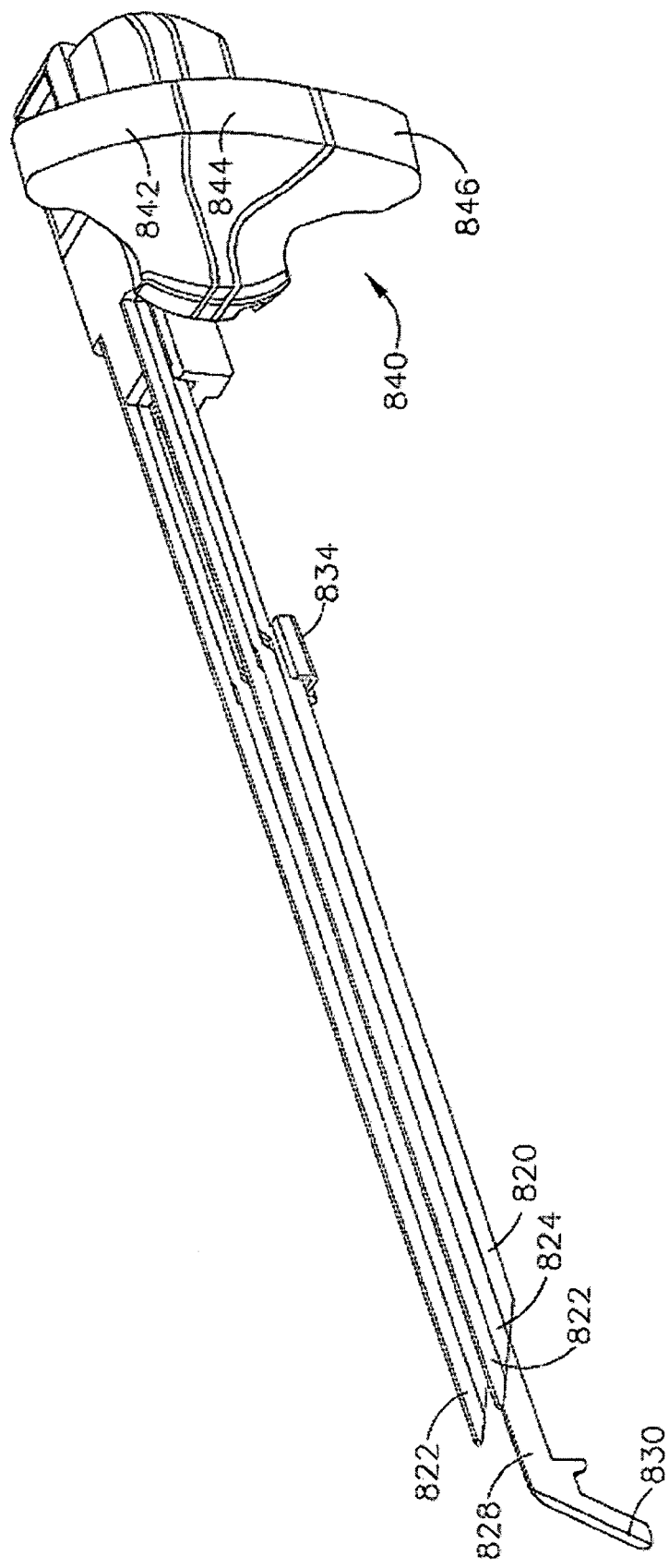
Figure 68:
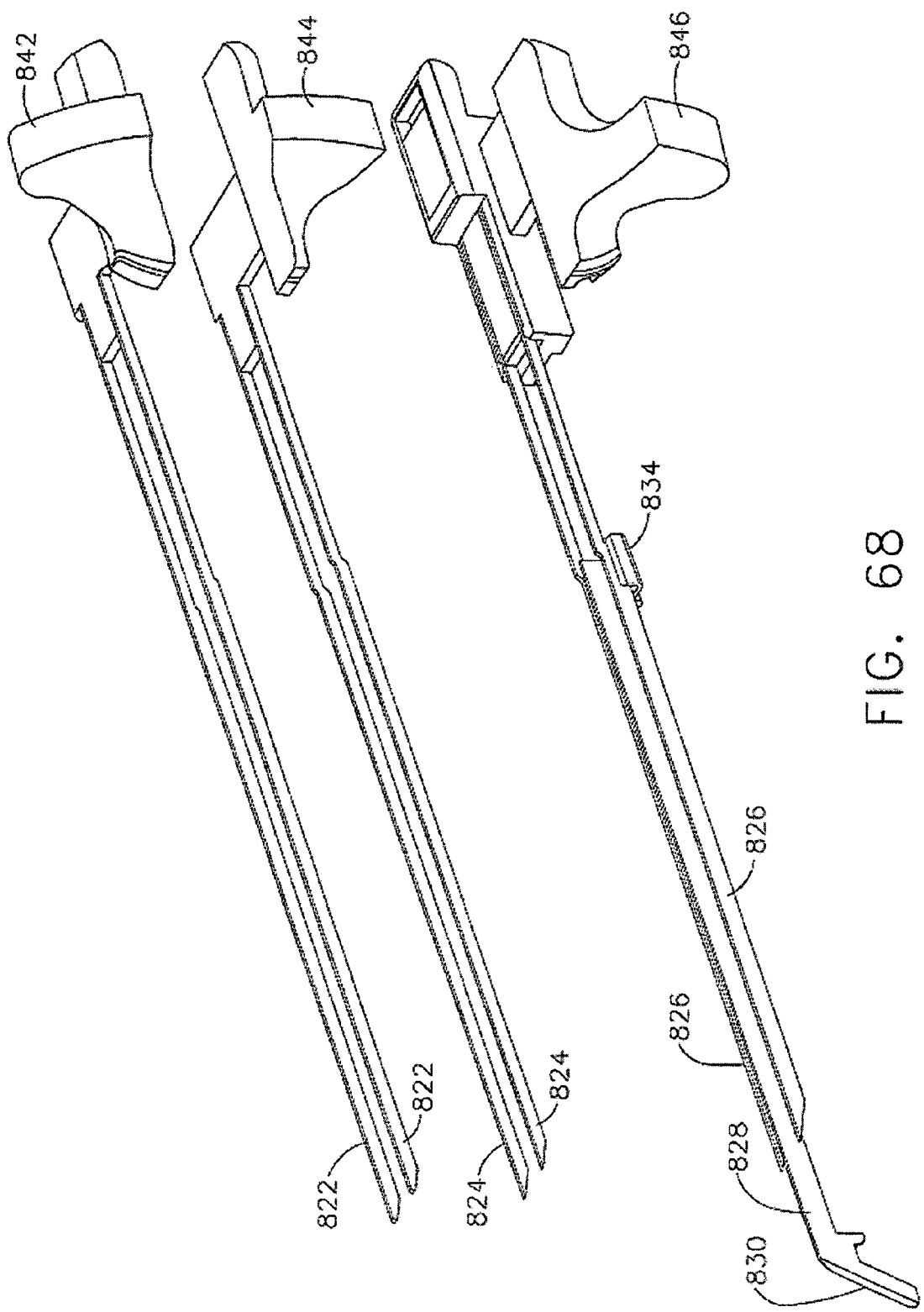
Figure 69:
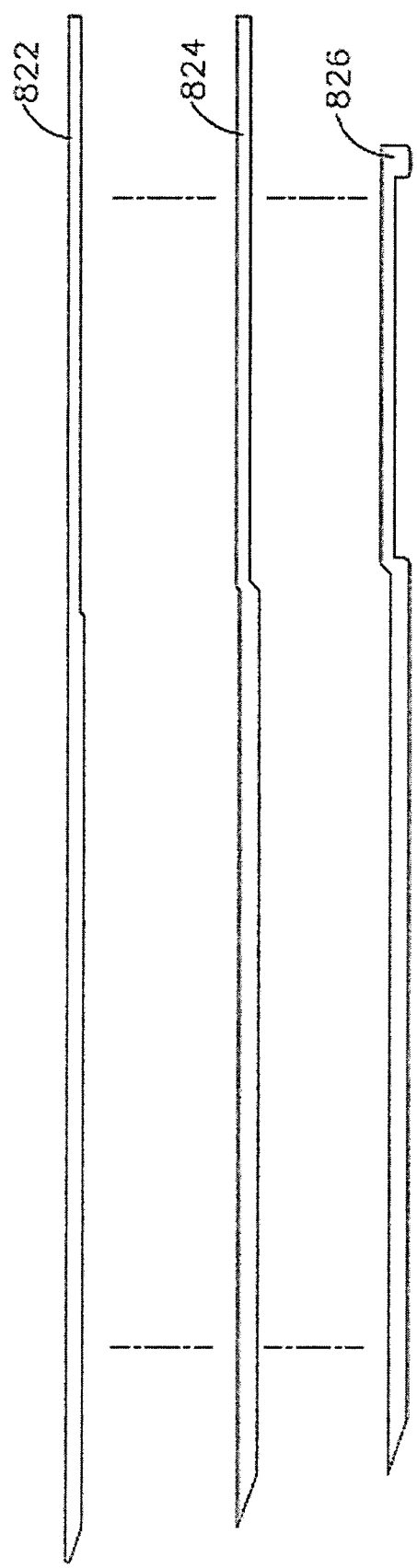

As best shown in FIGS. 67-68, the clinician may actuate the wedge band sets using a three-part actuation slide bar 840. The upper piece 842 may actuate the uppermost (initial) wedge band set 822. The middle piece 844 may actuate the middle wedge band set 824. The lower piece 846 may actuate the lowermost (last) wedge band set 826.

Figure 66:
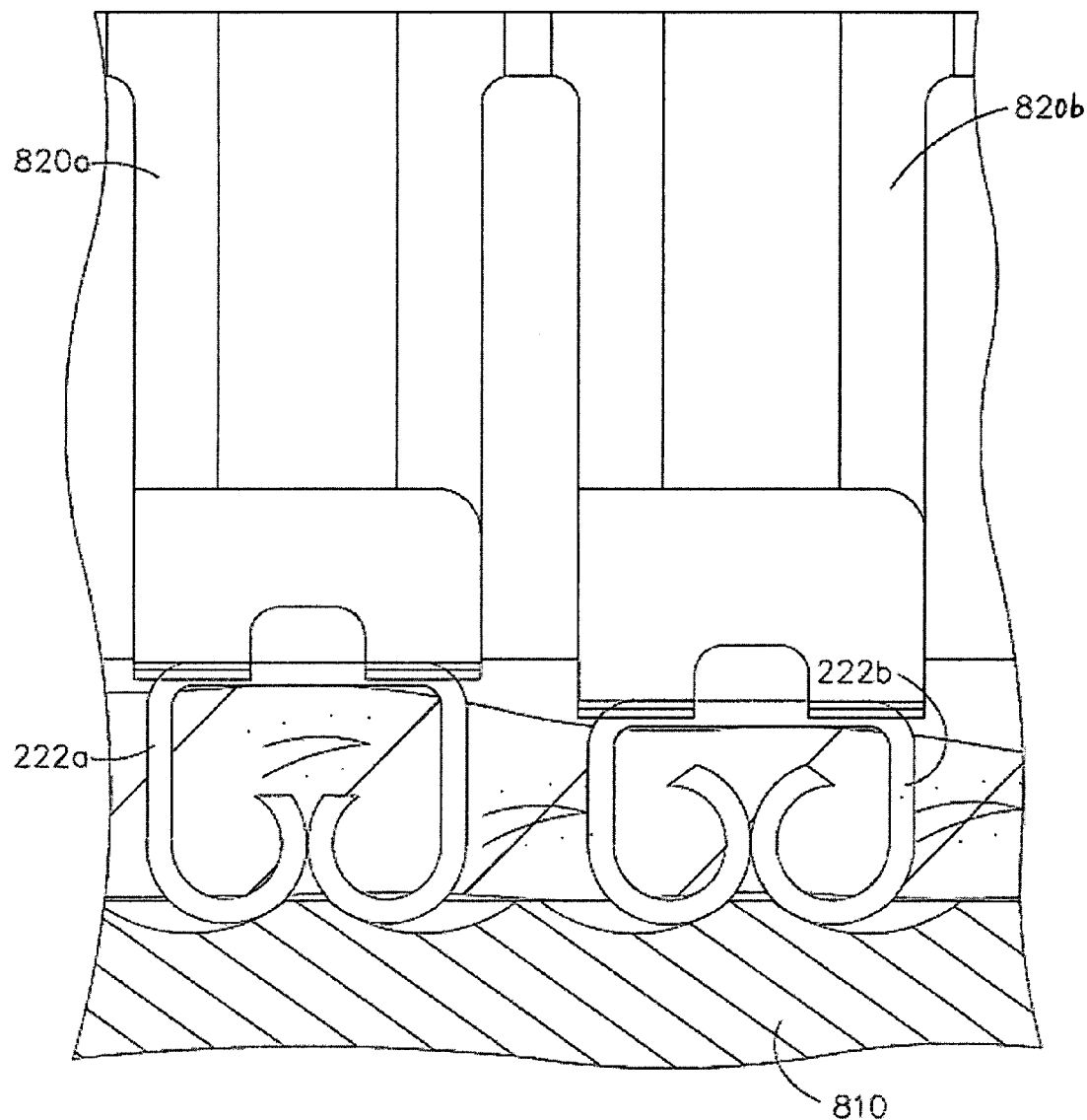

To form staples of different formed heights, the staple pushers 820 may have different heights. For example, as shown in FIG. 66, one set of staple pusher 820a could be shorter than another set of staple pushers 820b. As such, the formed staple 222a, produced by the shorter staple pusher 820a, may have a longer formed length than the formed staple 222b, formed by the longer staple pusher 820b. In other embodiments, the staples 222 may have different lengths or wire diameters to create different length formed staples, and/or the pockets 202 in the anvil 810 could have different depths to create different length formed staples. Also, the cumulative heights of the wedge band stacks could be different.

Figure 81:
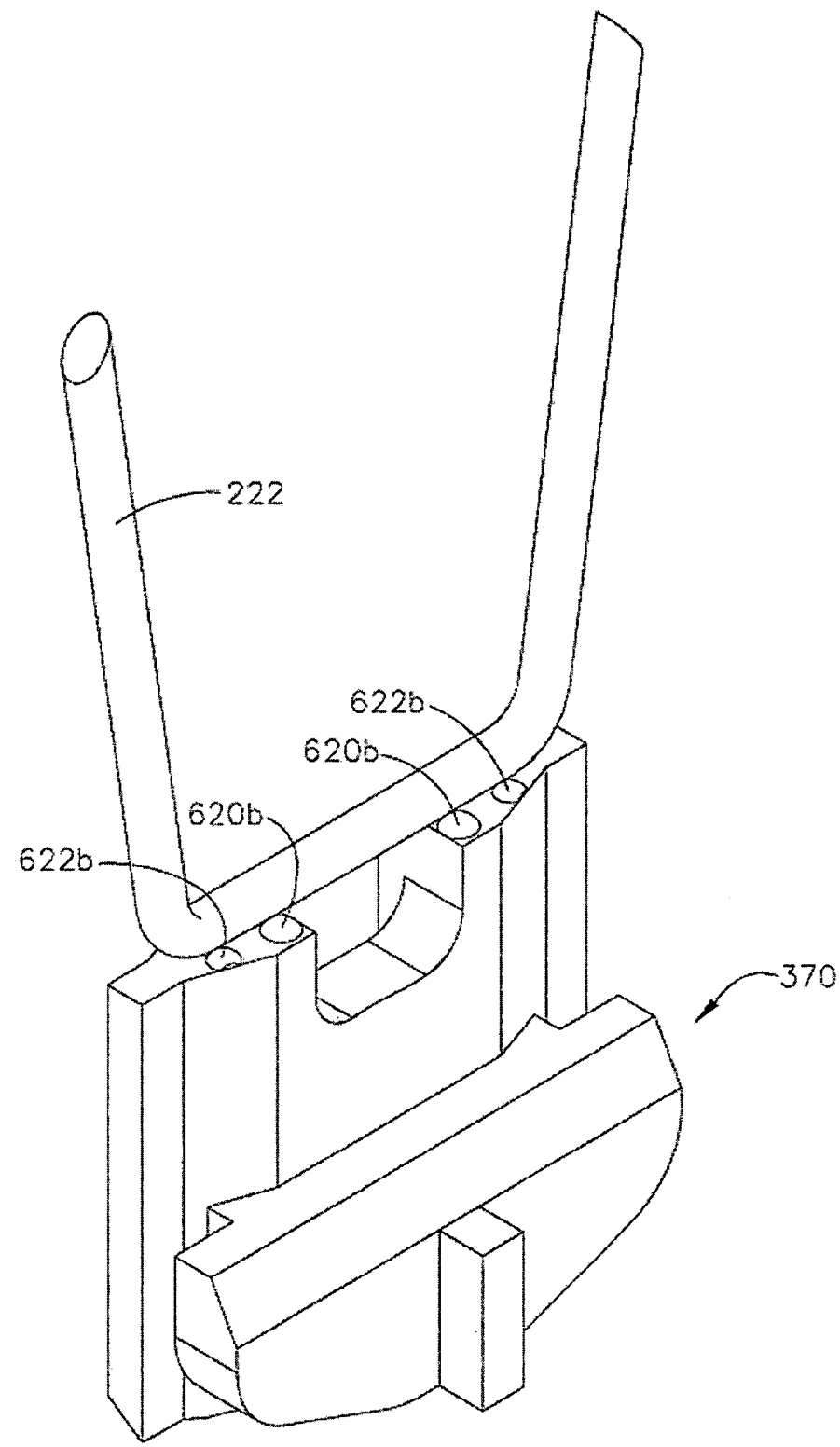
Figure 82:
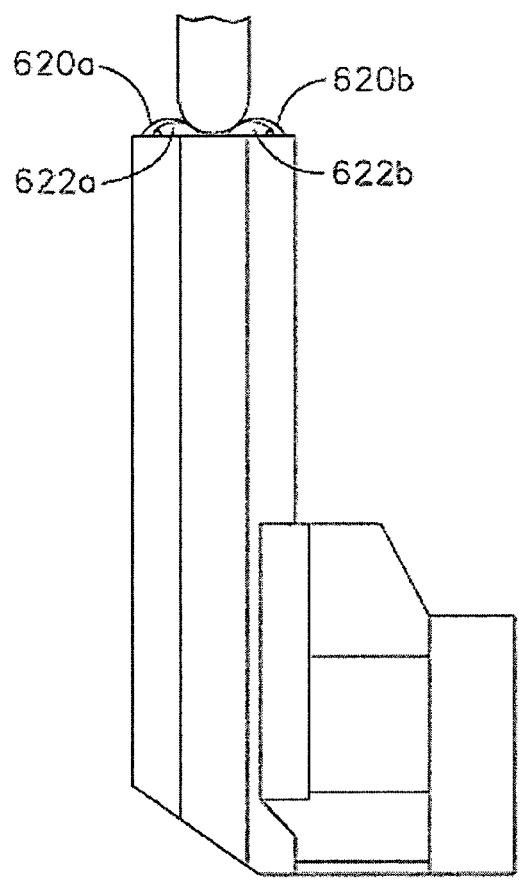
Figure 83:
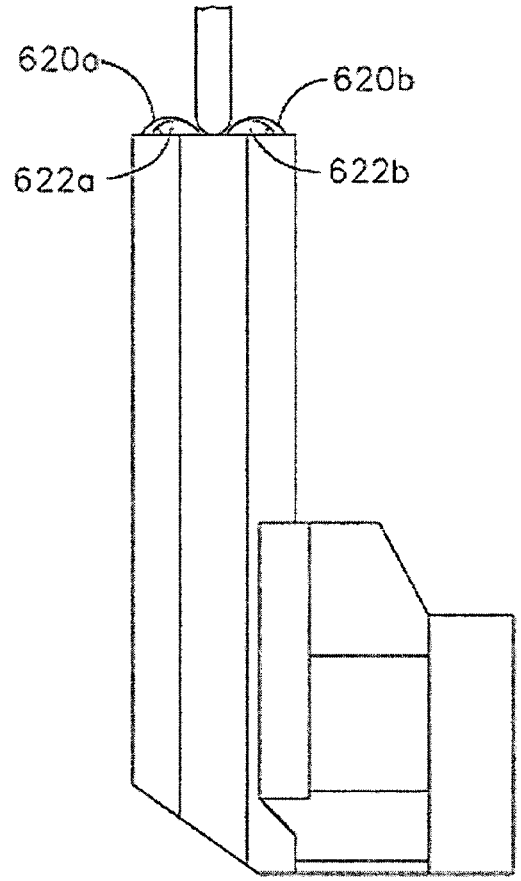

According to various embodiments of the present invention, the staple drivers could have a staple/driver interface that permits staples of varying wire diameter to be employed. For example, as shown in the embodiments of FIGS. 78-83, the outside staple drivers 370a,b may have a raised dimple configuration on its upper surface for supporting staples having differing wire diameters. The dimple configuration may comprise, as shown in the illustrated embodiment, two inner sets of outwardly protruding dimples (or convex bumps) 620a,b, and two outer sets of dimples 622a,b. Each set of dimples defines a receiving area where a staple 222 may sit in the upright position, as shown in FIGS. 81-83. The dimples of the inner sets 620a,b may be larger than the dimples of the outer dimple sets 622a,b so that the receiving area of the inner sets 620a,b is less than for the outer dimple sets 622a,b. Nevertheless, due to the convex nature of the dimples, staples 222 of varying wire thicknesses may be accommodated, as shown in FIGS. 82 and 83. For example, the dimples could be configured so that the staple drivers 370 can accommodate staples having a wire diameter of 0.006 inches to 0.012 inches, or some other range such as 0.004 inches to 0.008 inches or 0.006 inches to 0.008 inches, etc. As such, staples of different wire thicknesses could be used in a single cartridge 306. Differing wire diameters would produce different formed staple heights all other things being equal (e.g., same drive/crush distance, same pocket depth, etc.). In addition, as shown best in FIG. 78, the staple cradles for the inside drivers 330 may include sharp points 624 that may injure the tissue that is being stapled. The dimple configurations on the outside staple drivers 370 lack such sharp points, which would tend to minimize the trauma on the tissue being stapled.

In the illustrated embodiment, the outer staple drivers 370a,b have the raised dimple configuration in order to accommodate staples of different wire diameters and the staple cradles of the inside staple drivers 342, 352 can only support upright staples of one general wire diameter. In other embodiments, the one or both of the inside staple drivers 342, 352 may also or alternatively have the raised dimple configuration. Also, rather than using the raised dimple configuration, a v-shaped staple channel 349, 379 may be used. Such a v-shaped channel may also accommodate staples having different wire diameters. Also, staple pushers with staple interfaces that accommodate different staple wire diameters could be used with other types of staple drivers than the inside double and outside single staple drivers shown in FIGS. 78-83.

FIGS. 70-77 are cross-sectional frontal views of the end effector 12 according to various embodiments of the present invention. In the embodiment shown in FIG. 70, the anvil 18 is stepped, having a central portion 19 that is offset relative to (or not coplanar with) the two lateral side portions 21, 23. Also, the upper surface 306 of the cartridge 300 has a recessed central portion 307 and two lateral side portions 309 (see FIG. 19A). All the staples 222 have the same pre-formation prong height and the corresponding anvil pockets 202 have the same depth. However, due to the stepped nature of the anvil 18, the pockets 202 on the two lateral side portions 21, 23 of the anvil 18 are offset from the pockets in the central portion 19 of the anvil. Offsetting the vertical position of the staple forming pockets 202 can affect the length of the formed staples 222. All other things being equal, staples formed by staple forming pockets that are elevated will have a longer formed length than staples formed with pockets that are not elevated. Also in this embodiment, the primary and secondary driver portions 342, 352 of the double inside drivers 330a,b are the same height, and the height of the driver portion 372 of the outside staple drivers 370a,b is greater than the height of the driver portions 342, 352 of the double inside staple drivers 330a,b. Also, the inside and outside sled cams 410, 4120 are the same height in this embodiment.

Figure 71:
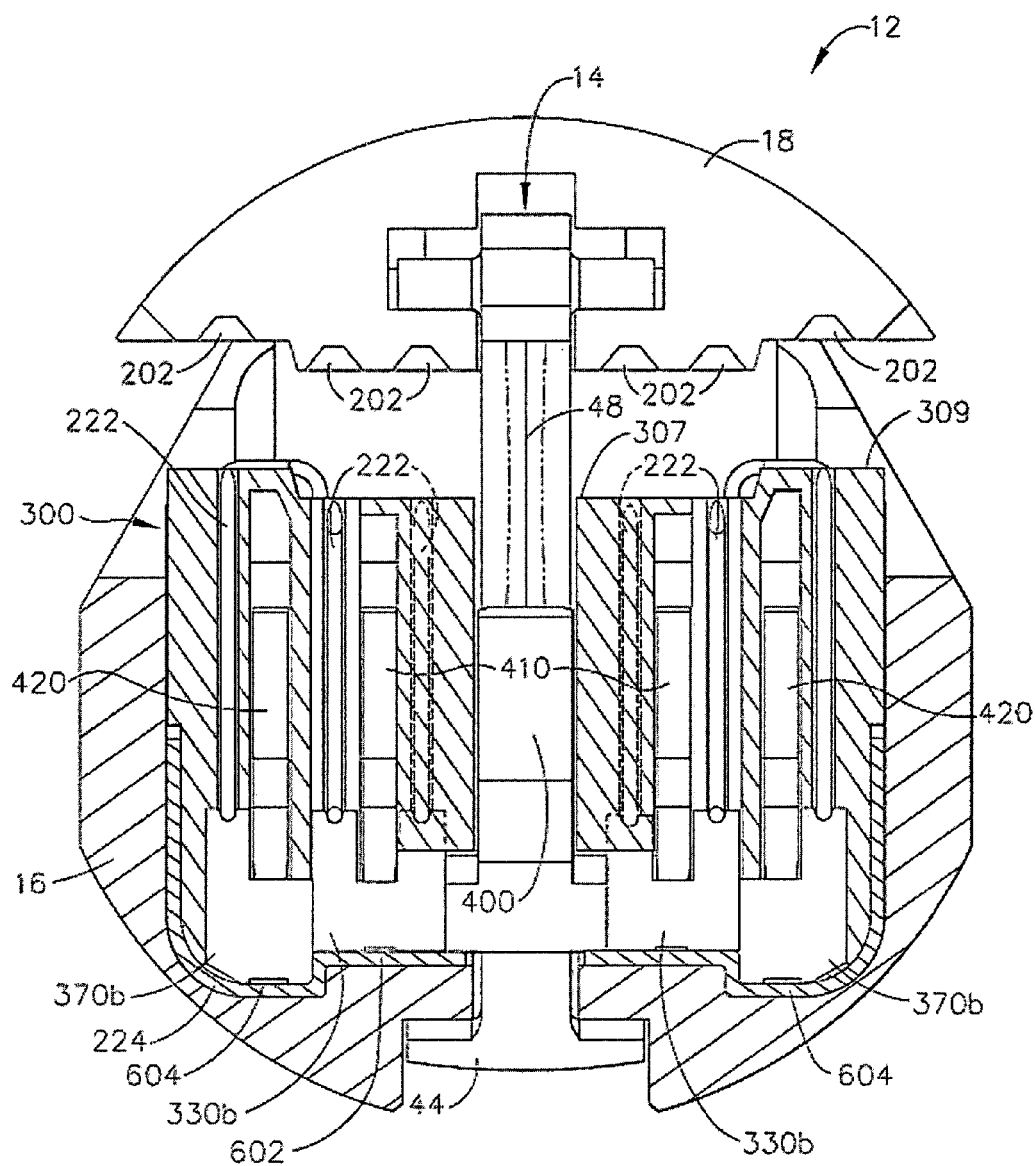

FIG. 71 shows an embodiment where the end effector 12 has a stepped cartridge tray 224 at the bottom of the cartridge 300 to match the steps in the channel 16. In particular, in the illustrated embodiment, the cartridge tray 224 has a central portion 602 on which the double inside staple drivers 330a,b rest and outer lateral portions 604 on which the outside staple drivers 370a,b rest. As can be seen in FIG. 71, the central portion 602 of the cartridge tray 224 is elevated above the lateral portions 604. As such, the sled 400 may be configured so that the outside sled cam 420 is positioned lower than the inside sled cam 410 so that the outside sled cam 420 can engage the lower outside driver portions 370a,b.

Figure 72:
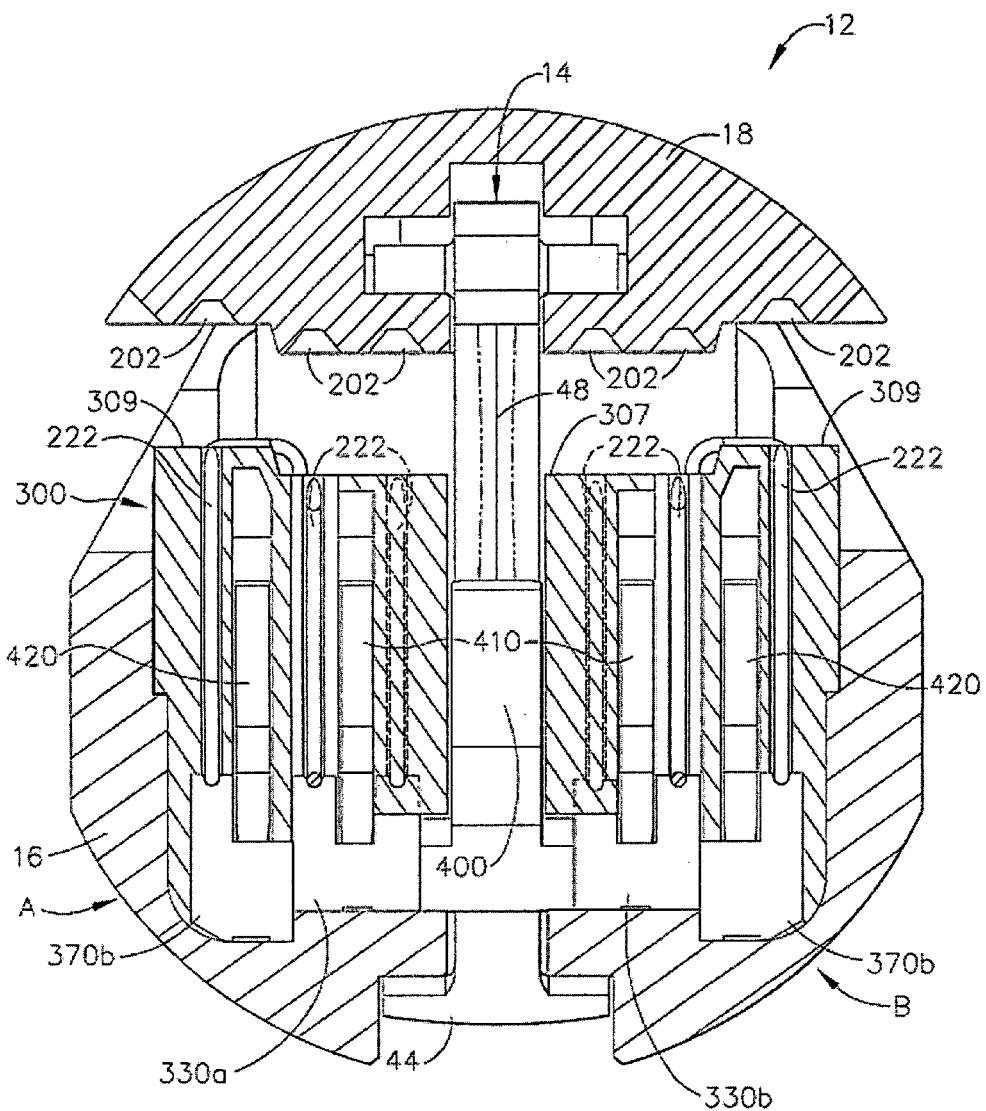

The embodiment illustrated in FIG. 72 is similar to that shown in FIG. 71 except that in FIG. 72 the cartridge 300 does not include the cartridge tray 224. Rather, the staple drivers 330, 370 rest directly on the channel 16. Such an embodiment may be beneficial because it may allow for more material (e.g., metal) in the channel 16 at points A and B than in a similar embodiment with the cartridge tray 224 (such as shown in FIG. 71).

Figure 73:
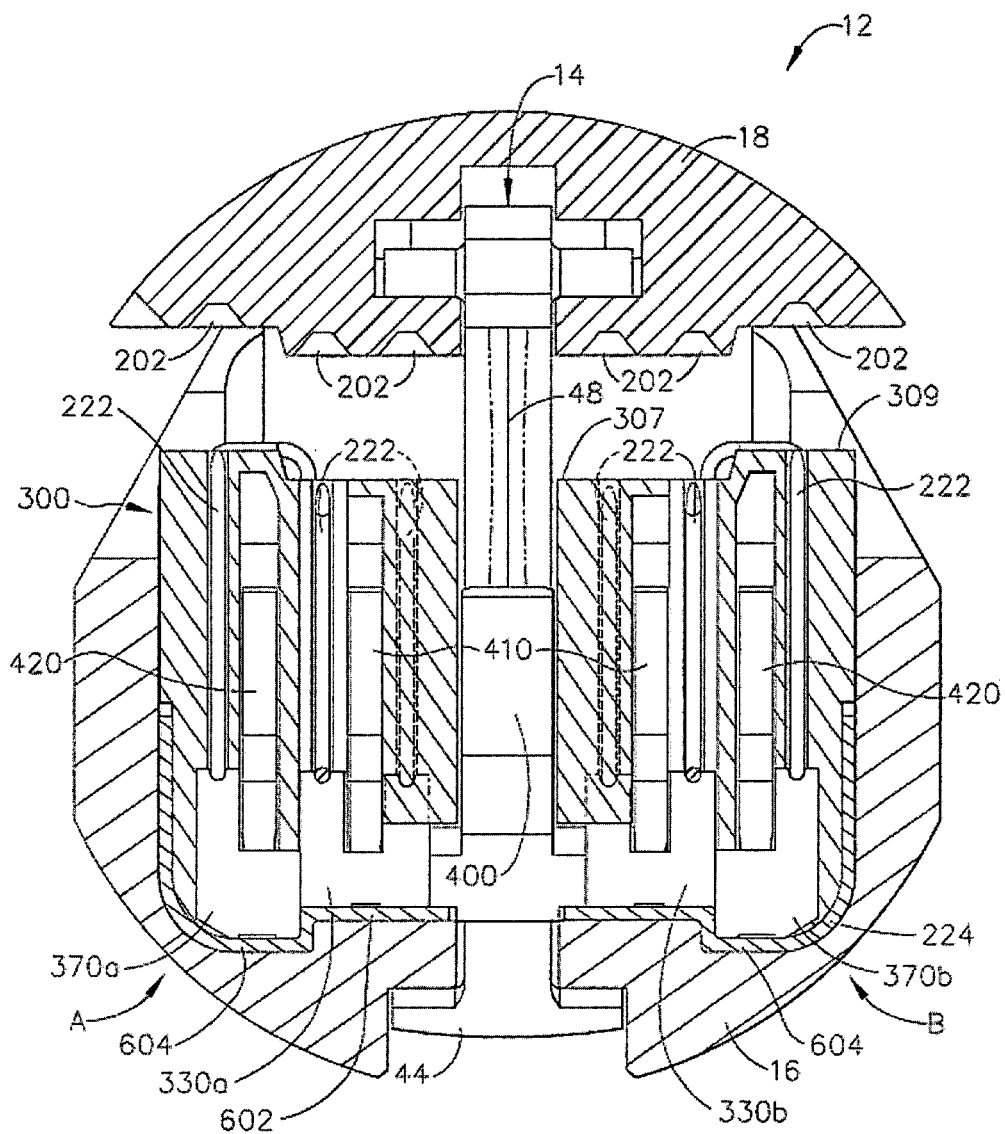

The embodiment illustrated in FIG. 73 is also similar to that shown in FIG. 71 except that in FIG. 73 the cartridge tray 224 is raised slightly relative to the bottom on the channel 16 in comparison with the embodiment shown in FIG. 71. Such an embodiment may also allow for more material (e.g., metal) in the channel 16 at points A and B than in the embodiment shown in FIG. 71. According to other embodiments, the height of the anvil 18 could be reduced to permit more material in the channel 16 at points A and B.

Figure 74:
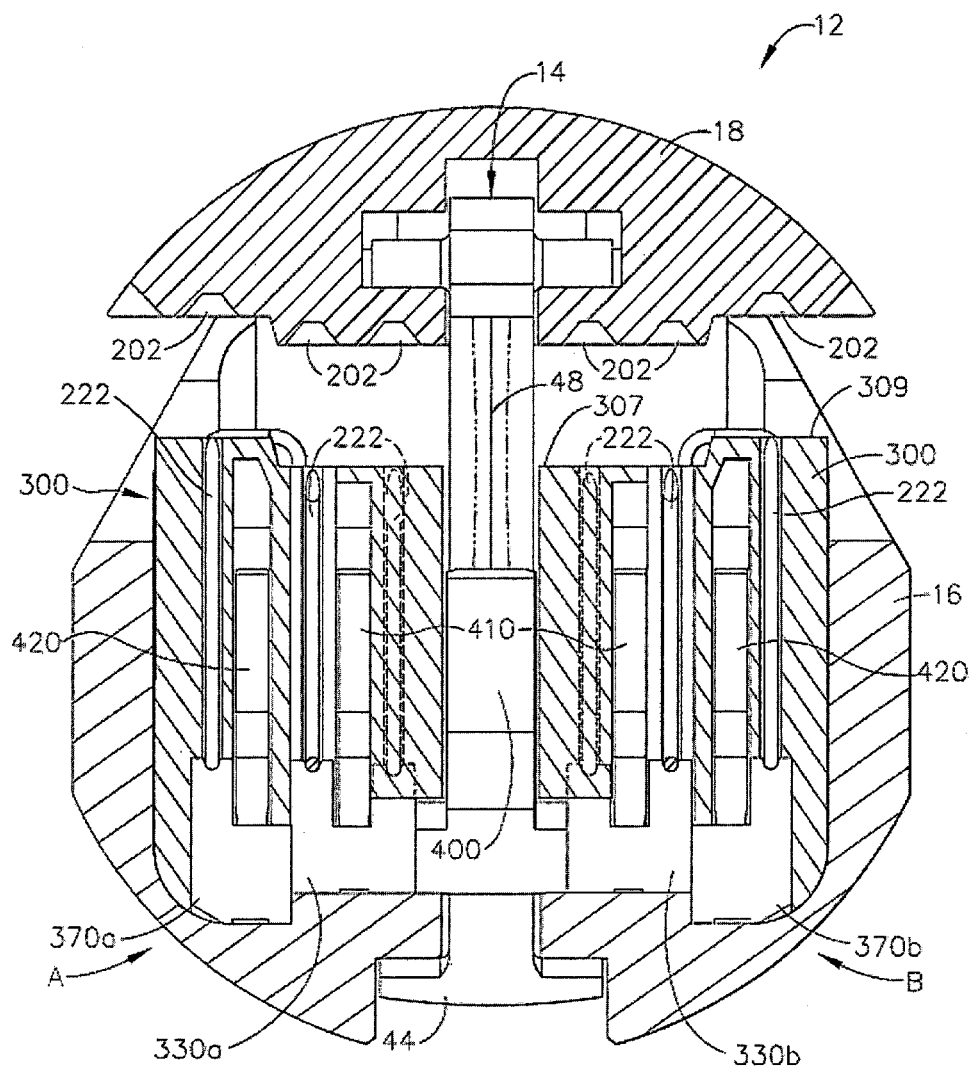

The embodiment of FIG. 74 is similar to that used in FIG. 73 except that no cartridge tray 224 is included in the embodiment of FIG. 74.

Figure 70:
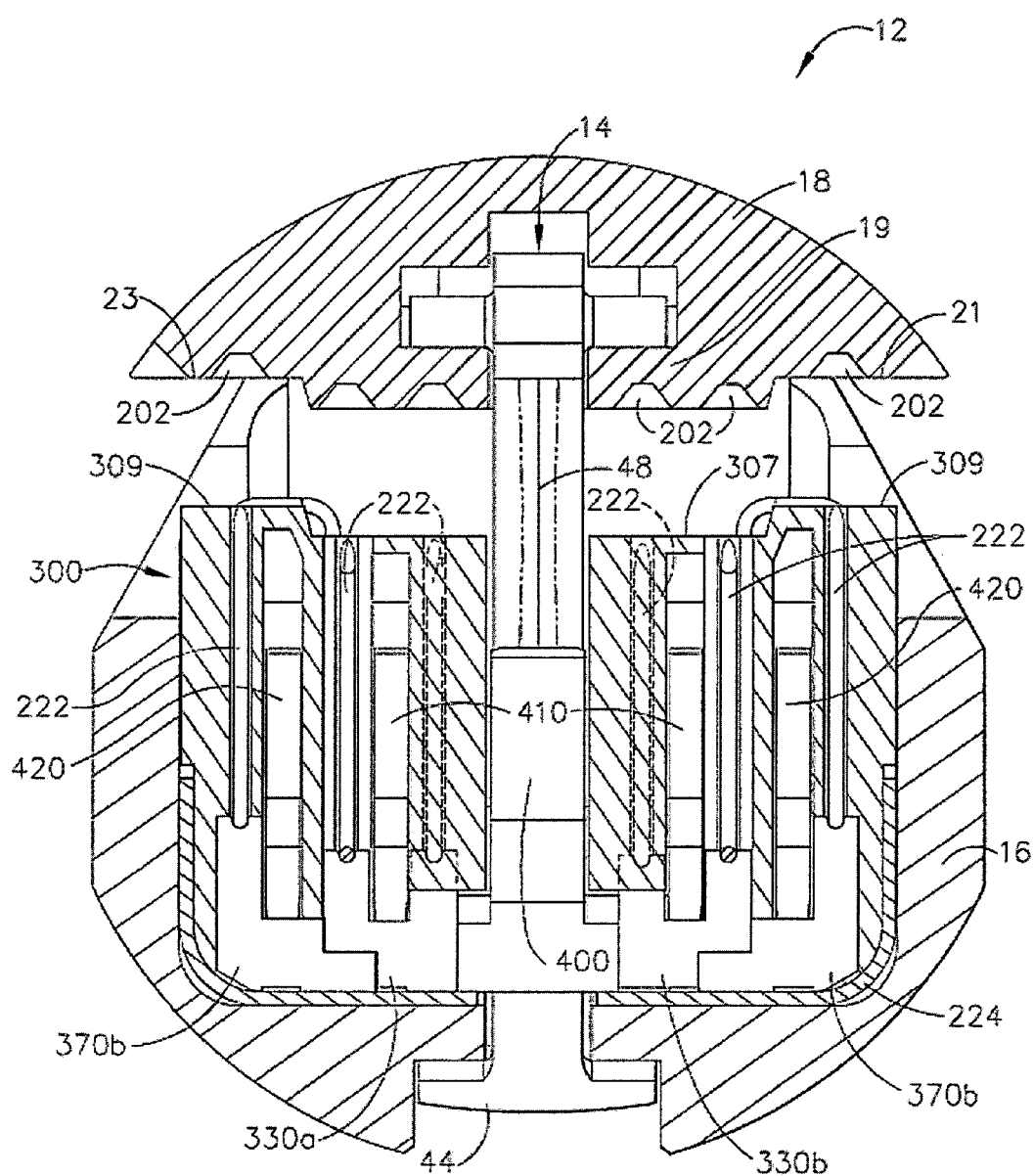
FIGS. 70-77 depicts cross-sectional front views of an end effector according to various embodiments of the present invention.
Figure 75:
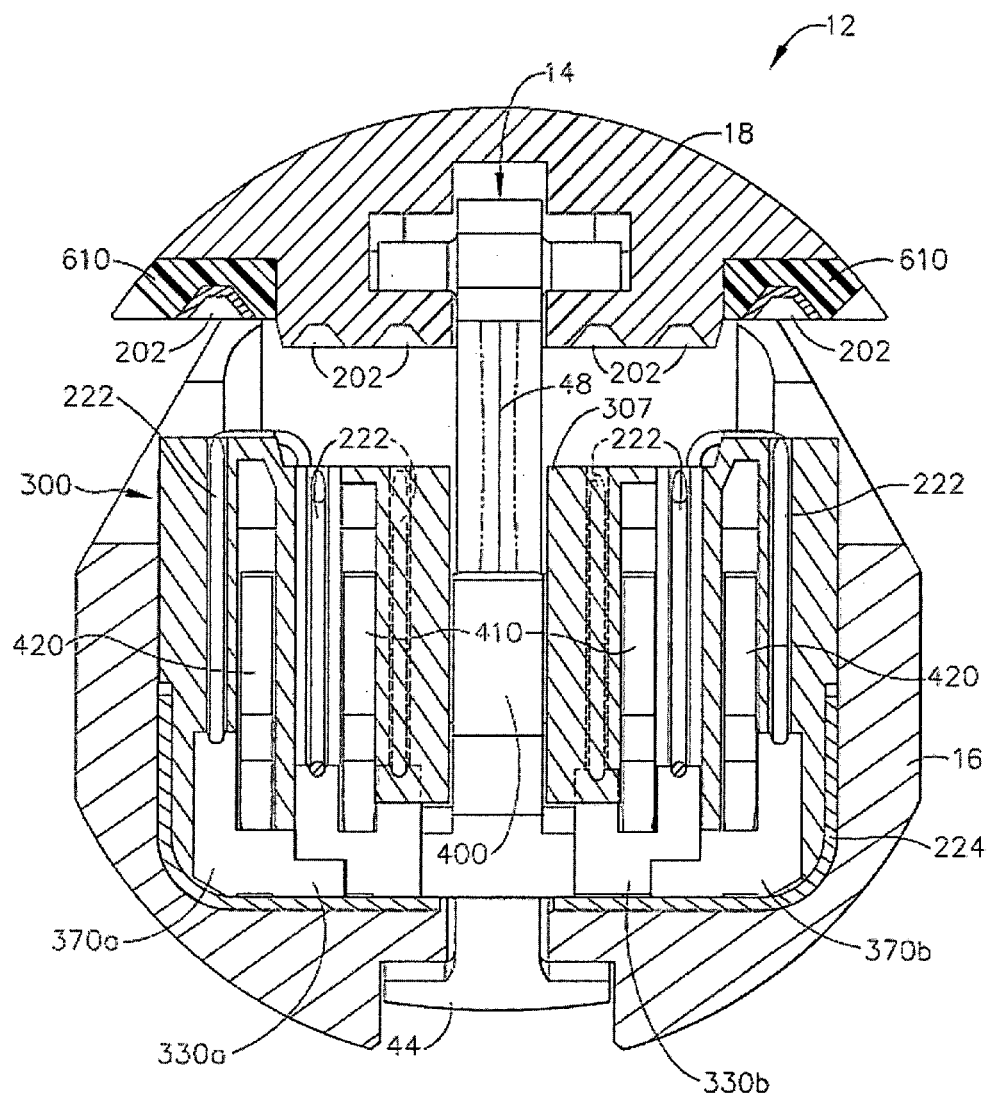

The embodiment of FIG. 75 is similar to that of FIG. 70 except than in FIG. 75 the outer rows of pockets 202 are formed in a compliant material portion 610 of the anvil 18. The compliant material portion 610 may be made from a material that is more compliant to the rest of the anvil 18. For example, the compliant material portion 610 may be made from plastic or a plastic composite material and the rest of the pockets may be defined in a less-compliant material, such as stainless steel, of the anvil 18. The less-compliant anvil portion is sometimes referred to herein as "non-compliant" to distinguish it from the compliant materials portion 610, although it should be recognized that the so-called non-compliant material portion would be somewhat compliant, just less compliant than the compliant material portion 610. All things being equal, staples formed with the outer pockets 202 formed in the compliant material portion 610 of the anvil 18 would be longer than stapled form in the non-compliant (e.g., metal) portion of the anvil 18 because the compliant material portion 610 would compress more during the staple formation process.

Figure 76:
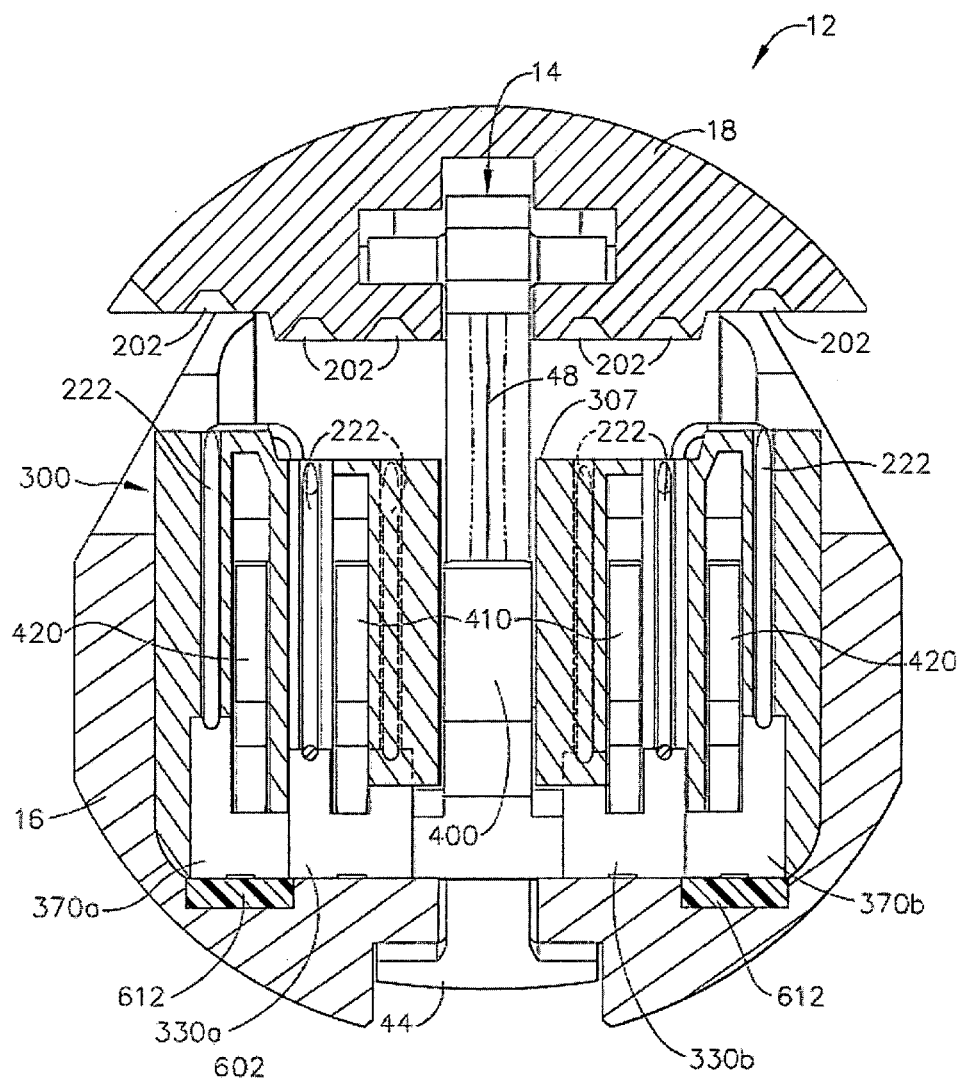
Figure 77:
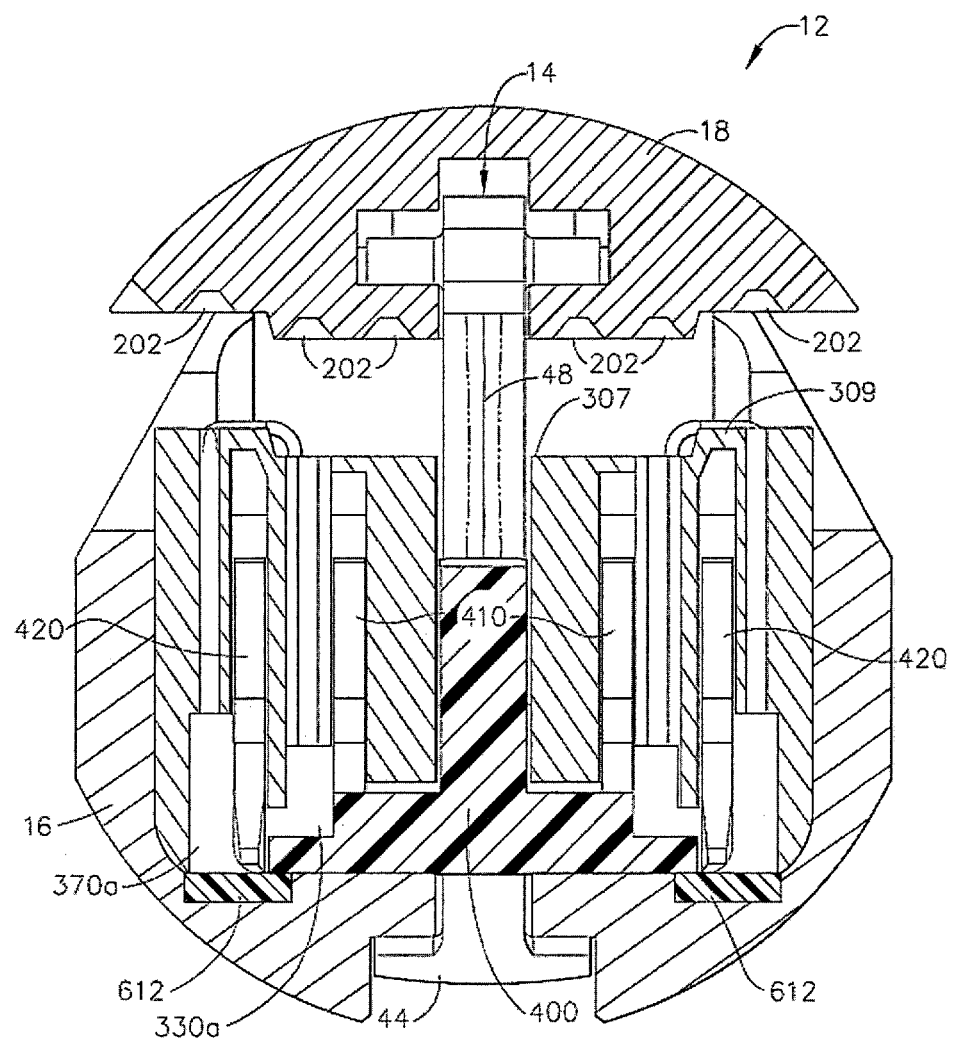
Figure 78:
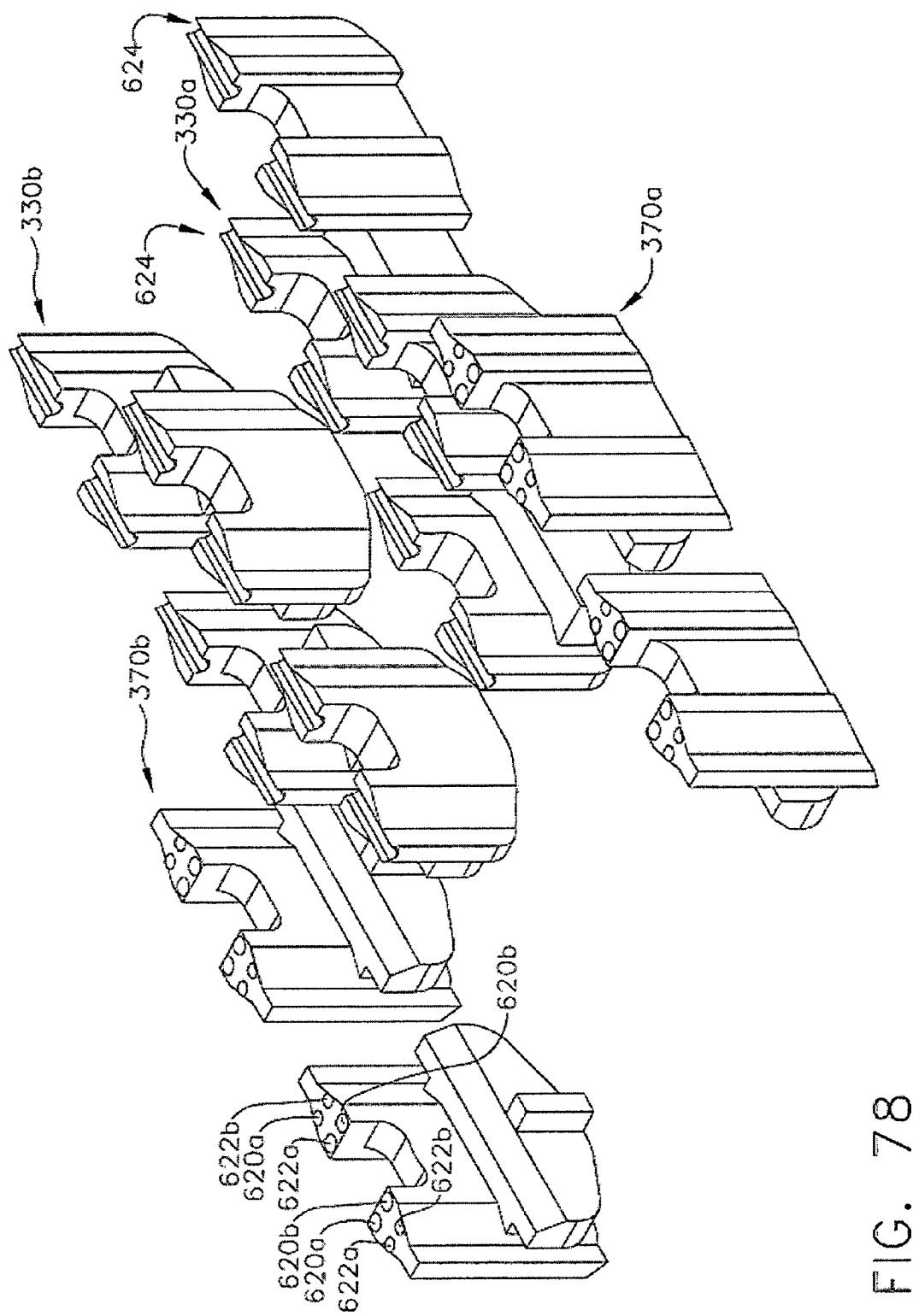
FIGS. 78-83 depict staple drivers that can accommodate staple having different wire diameters according to various embodiments of the present invention.
Figure 79:
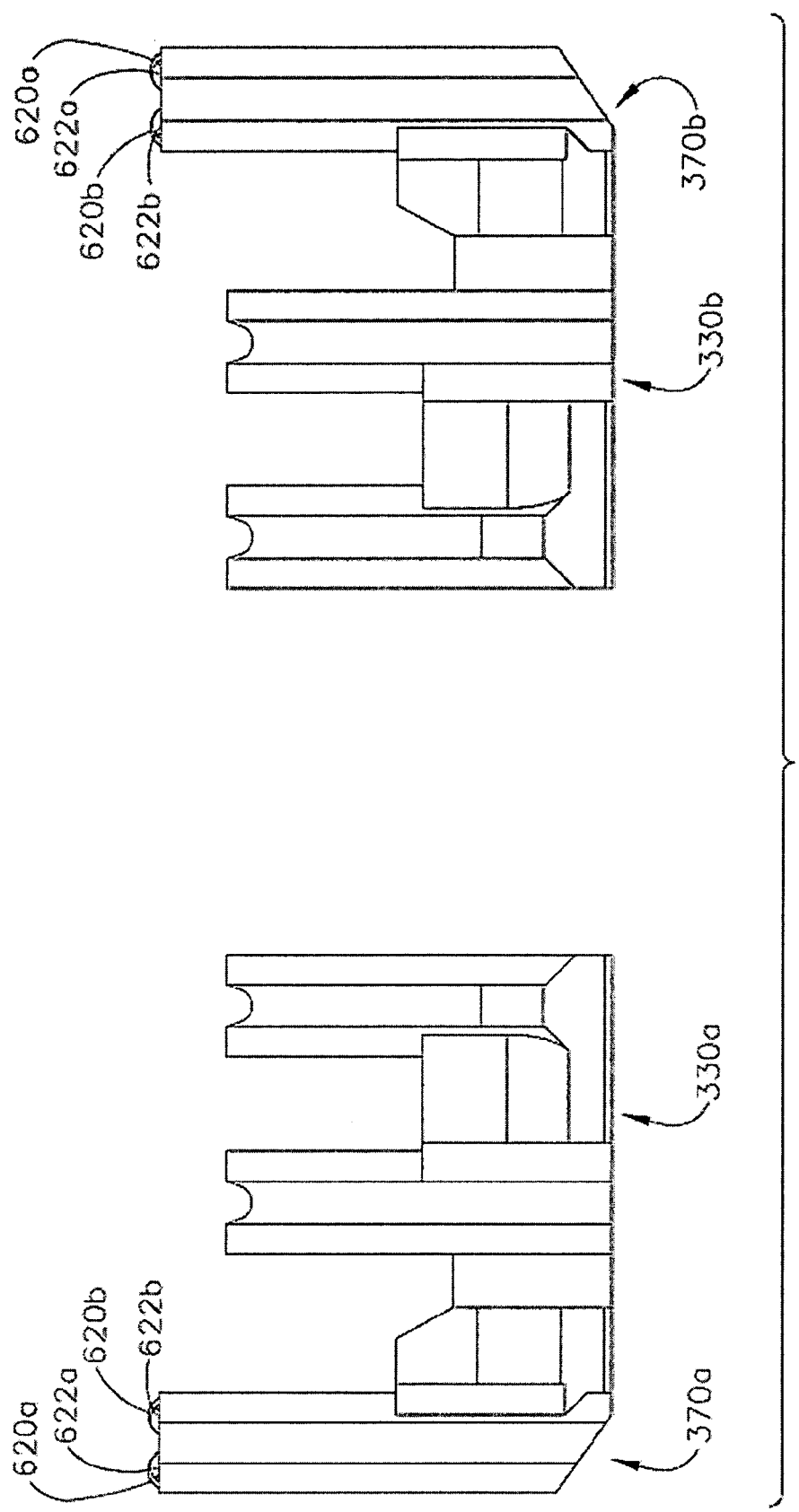
Figure 80:
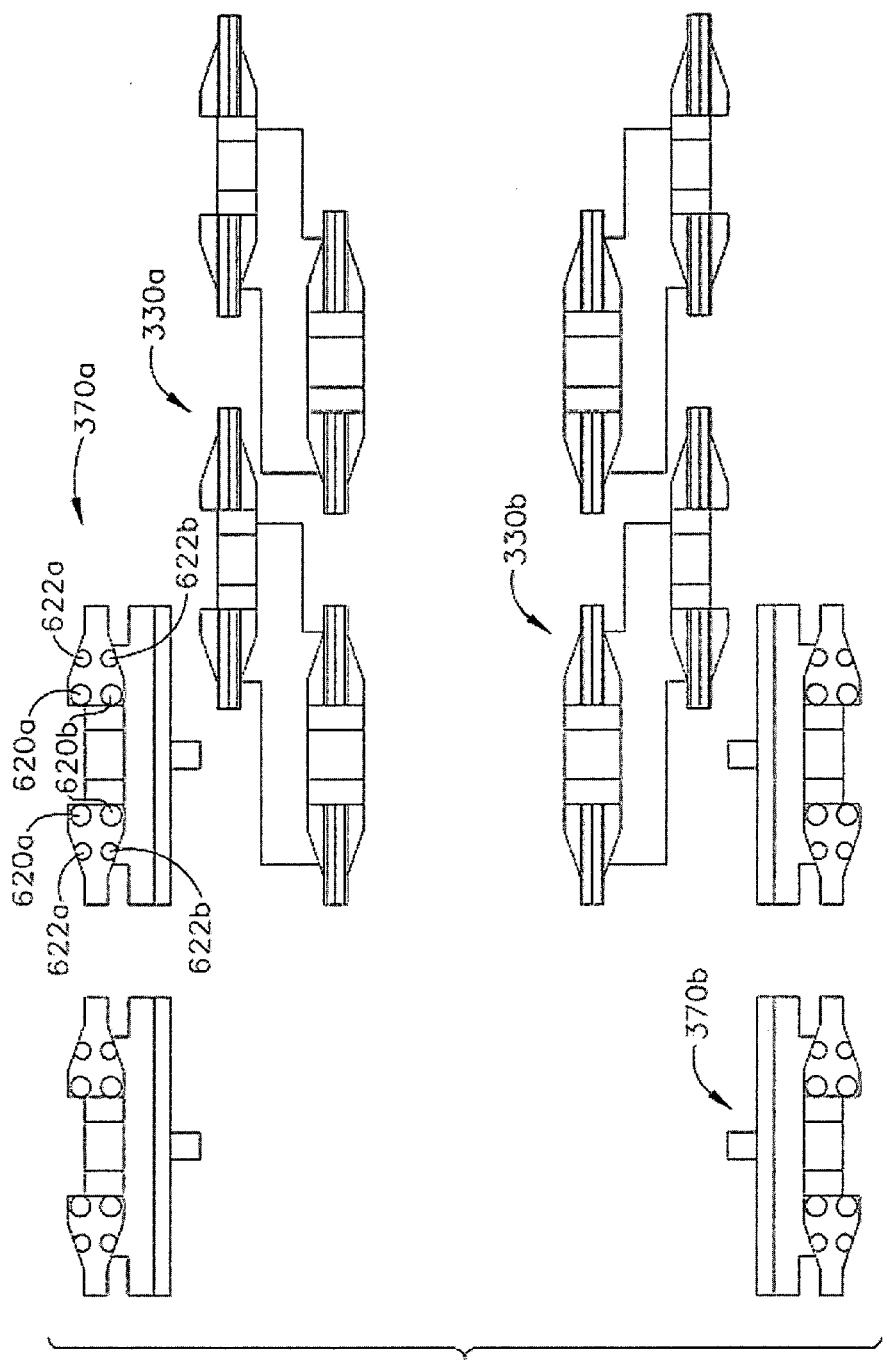

FIGS. 76 and 77 collectively show another embodiment. In this embodiment, the channel 16 includes a compliant material portion 612 under the outside drivers 370. The complaint material portion 612 may be plastic or a composite plastic, for example. The inside drivers 330 may rest on the less-compliant (or "non-compliant") channel 16, which may be made of metal (e.g., stainless steel). The outside sled cam 420 may slightly compress the compliant material portions 612 under the outside drivers 370 when forming the staples in relation to the inside drivers 330 on the channel 16, thereby forming slightly longer staples in the outside rows. In other embodiments, the compliant material portions 612 could be under the inside drivers 330 if it was desired to make the inside staples have a greater formed length.

According to other embodiments, staples of different materials could be used to produce staples of different formed lengths. The different materials may have different modulus of elasticity so that they will be formed differently given the same driving force. Staples having a higher modulus of elasticity will tend to be deformed less given the same driving force, thereby tending to produce staples having a longer formed length. The different materials for the staples 222 may comprise titanium, stainless steel, alloys, etc.

Figure 84:
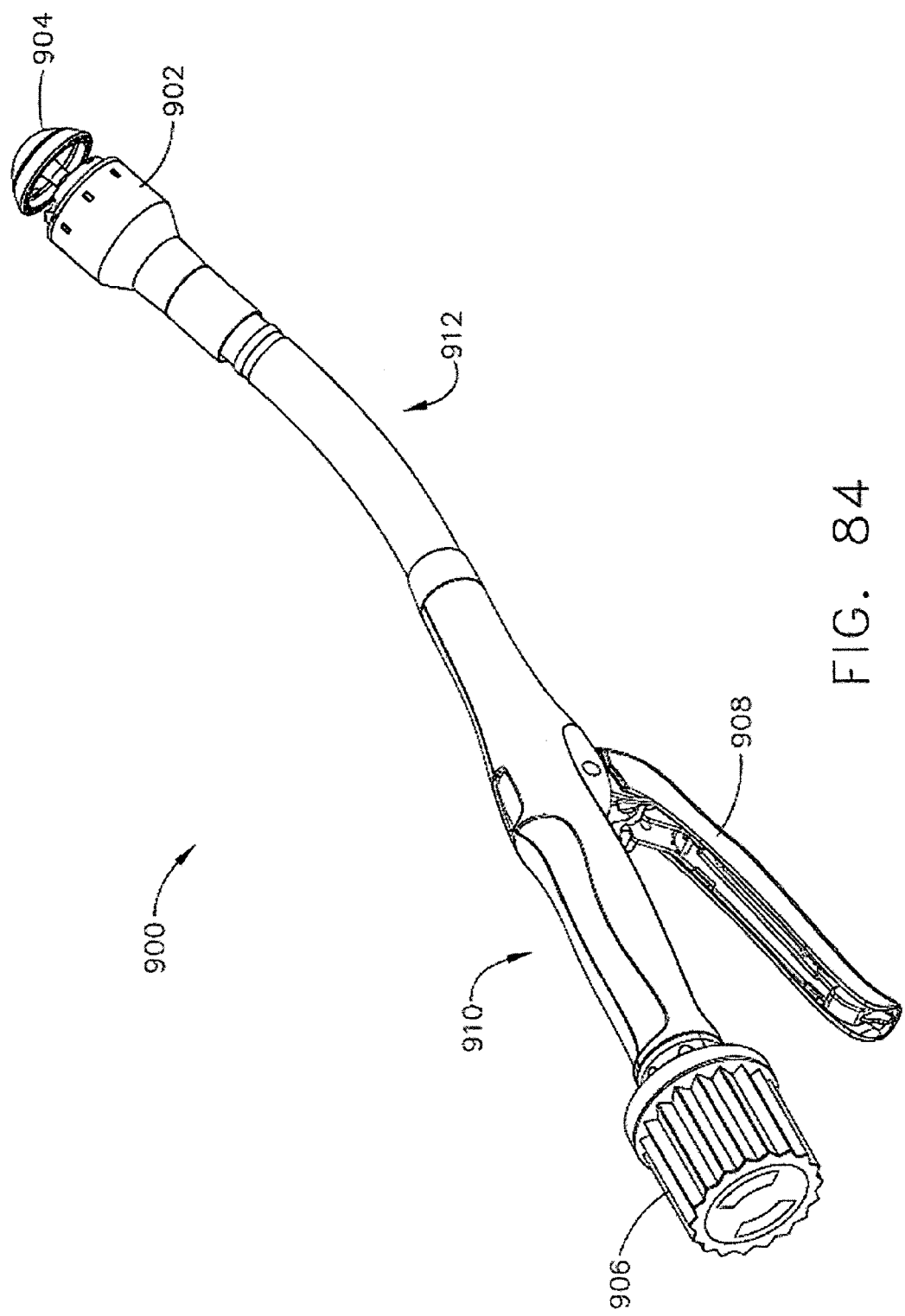
FIGS. 84-89 depict a circular surgical stapling device according to various embodiments of the present invention.

The present invention is also directed to other types of surgical cutting devices that can create formed staples of different heights. For example, FIGS. 84-89 illustrate a circular stapler 900 that is capable of forming staples with different formed heights. As seen in FIG. 84, the circular stapler 900 includes a head 902, an anvil 904, an adjustment knob assembly 906, and a trigger 908. The head 902 is coupled to a handle assembly 910 by an arcuate shaft assembly 912. The trigger 908 is pivotally supported by the handle assembly 910 and acts to operate the stapler 900 when a safety mechanism (not shown) is released. When the trigger 908 is activated, a firing mechanism (not shown in FIG. 84) operates within the shaft assembly 912 so that staples 914 are expelled from the head 902 into forming contact with the anvil 904. Simultaneously, a knife 916 operably supported within the head 902 acts to cut tissue clamped between the head 902 and the anvil 904. The stapler 900 is then pulled through the tissue leaving stapled tissue in its place.

Figure 85:
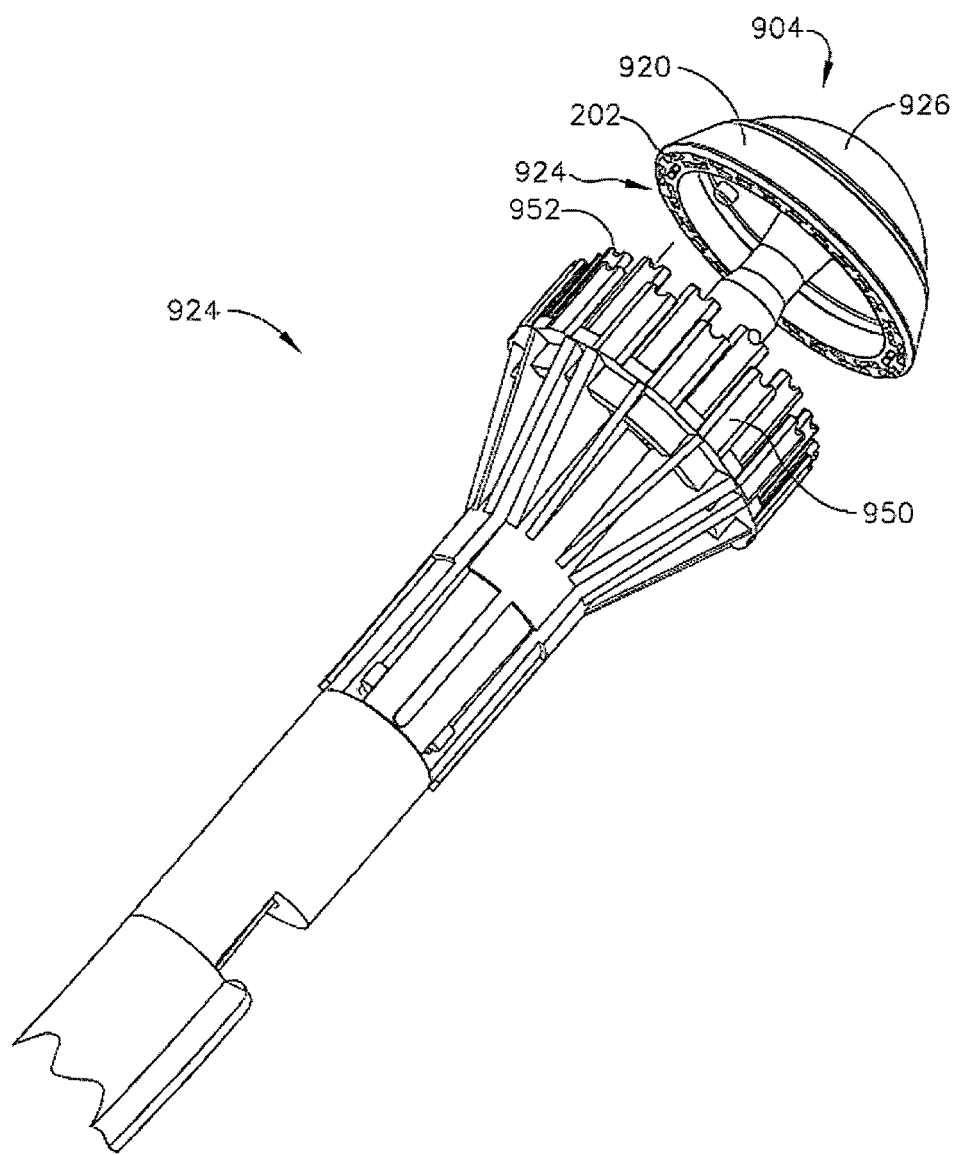
Figure 86:
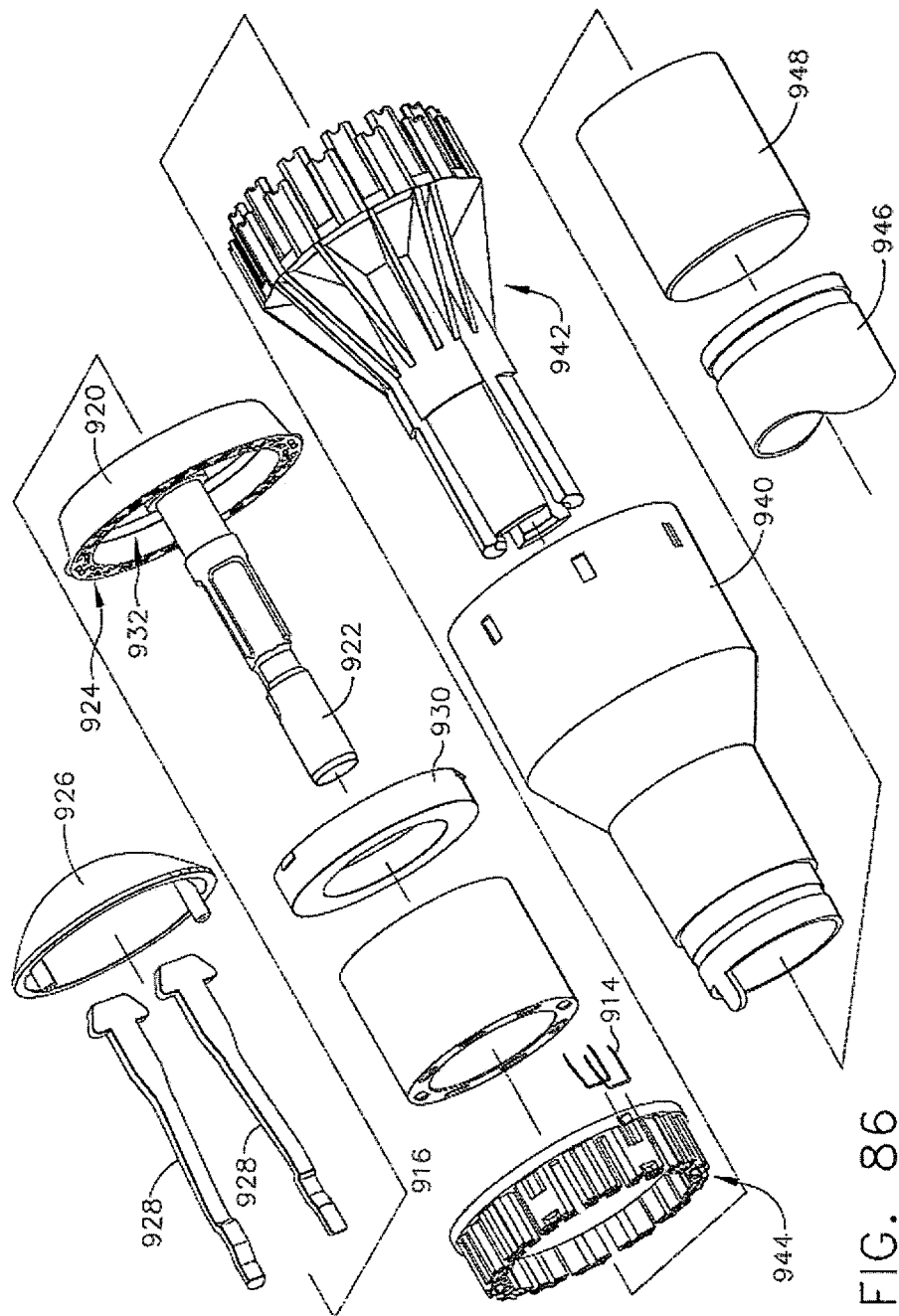
Figure 87:
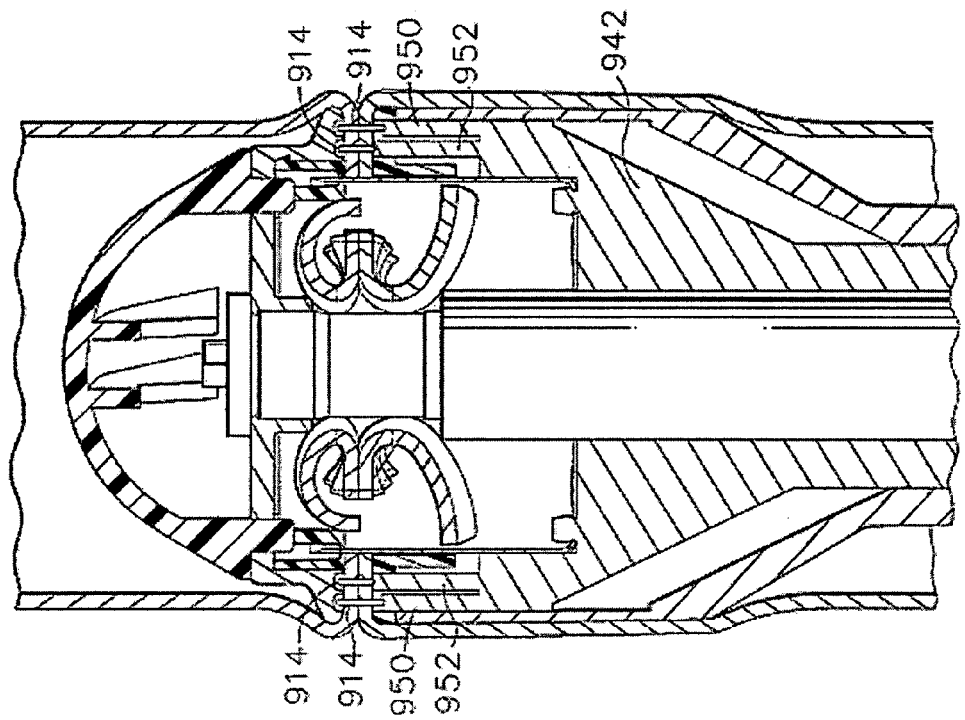

FIGS. 85 and 86 illustrate one form of the anvil 904 and the head 902 that may be employed in connection with various embodiments of the subject invention. As can be seen in these figures, the anvil 904 may have a circular body portion 920 that has an anvil shaft 922 for attaching a trocar (not shown) thereto. The anvil body 920 has a staple forming surface 924 thereon and may also have a shroud 926 attached to the distal end thereof. The anvil 904 may be further provided with a pair of trocar retaining clips or leaf-type springs 928 that serve to releasably retain the trocar in retaining engagement with the anvil shaft 922. A plastic knife board 930 may be fitted into a cavity 932 in the anvil body 904.

The head 902 may comprise a casing member 940 that supports a cartridge supporting assembly in the form of a circular staple driver assembly 942 therein that is adapted to interface with a circular staple cartridge 944 and drive the staples 914 supported therein into forming contact with the staple forming surface 924 of the anvil 904. The circular knife member 916 is also centrally disposed within the staple driver assembly 942. The proximal end of the casing member 940 may be coupled to an outer tubular shroud 946 of the arcuate shaft assembly 912 by a distal ferrule member 948. More details regarding circular staples may be found in U.S. patent application Ser. No. 11/541,151, entitled "Surgical Cutting and Stapling Device with Closure Apparatus for Limiting Maximum Tissue Compression Force," by F. Shelton et al., filed Sep. 29, 2006, which is incorporated herein by reference.

As can be seen in FIGS. 85-89, the staple driver assembly 942 may comprise an outer ring of staple drivers 950 and an inner ring of staple drivers 952. Correspondingly, the anvil 904 may comprise two concentric rings of staple forming pockets 202. Actuation of the firing trigger 908 of the handle assembly 910 cause a compression shaft (not shown) of the shaft assembly 912 to move distally thereby driving the staple driver assembly 942 distally to fire the staples 914 into forming contact with the staple forming surface 924 of the anvil 904. Thus, the outer staple drivers 950, when actuated by the drive mechanism of the stapler 900, drive an outer ring of staples 914 into the clamped tissue and are formed by surface forming surface 924 of the anvil 904. Similarly, the inner staple drivers 952, when actuated by the drive mechanism of the stapler 900, drive an outer ring of staples 914 into the clamped tissue and are formed by surface forming surface 924 of the anvil 904.

Figure 88:
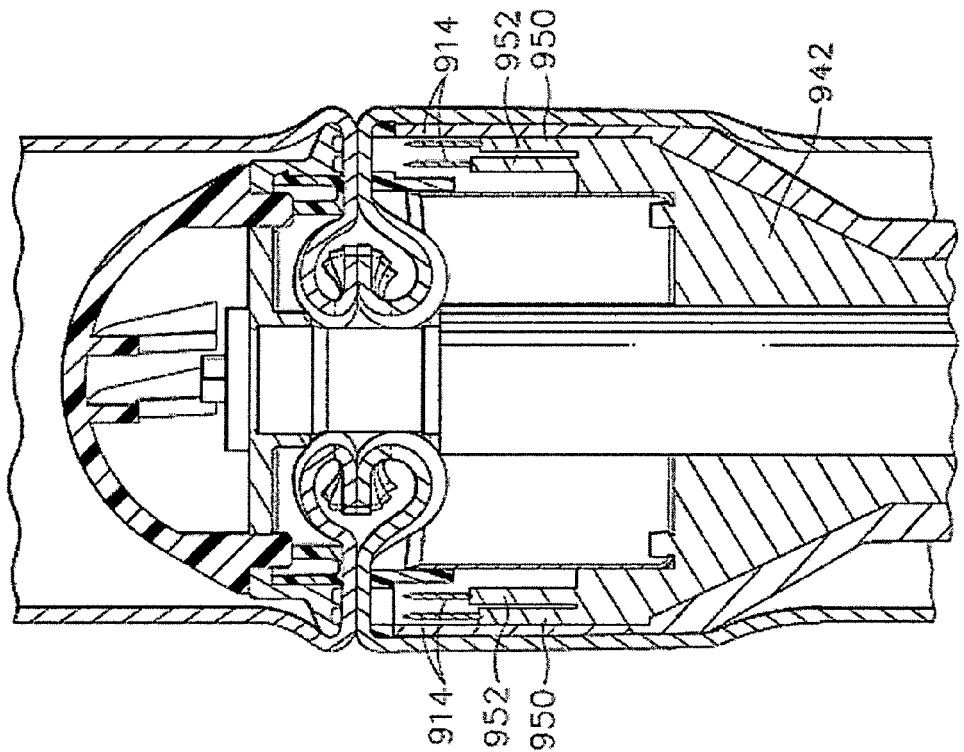
Figure 89:
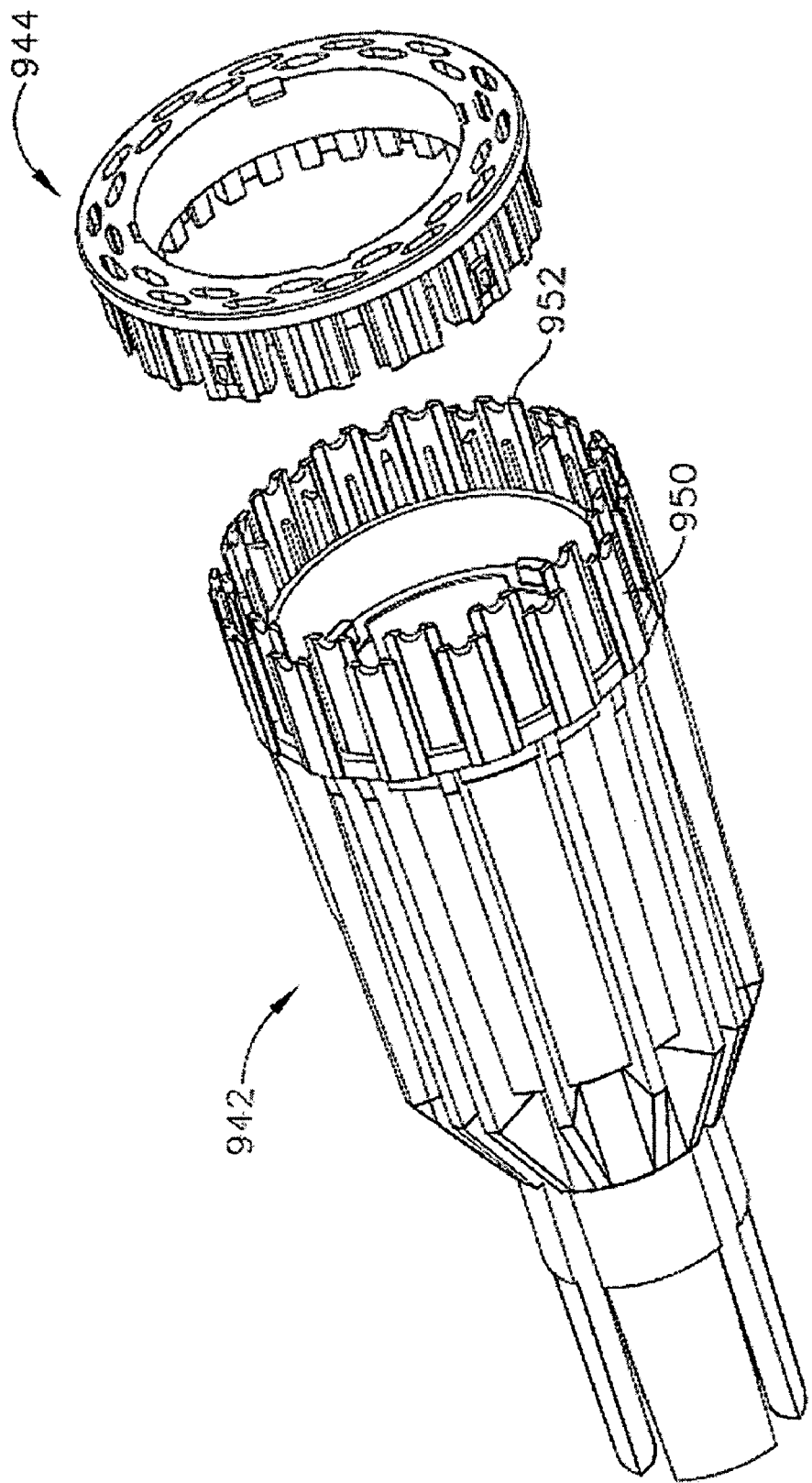
Figure 90:
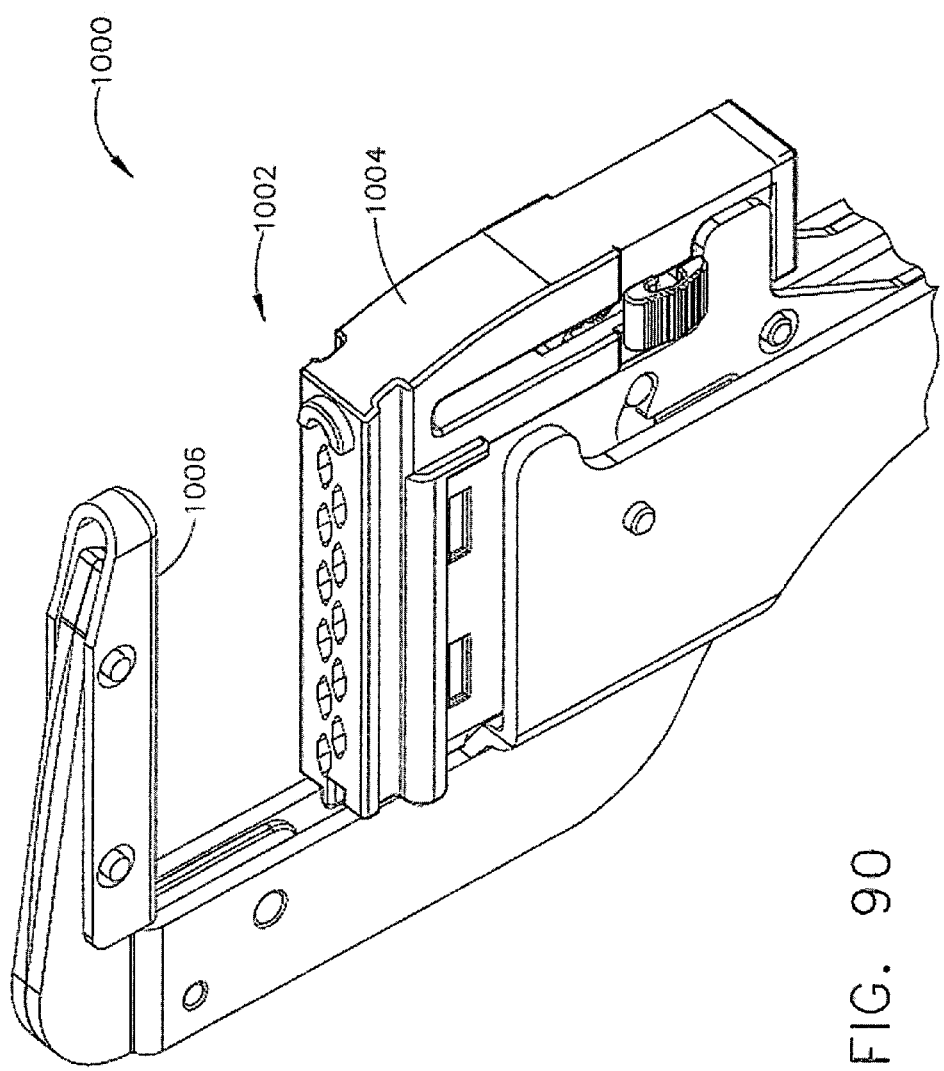
FIGS. 90-95 depict another surgical stapling device according to embodiments of the present invention.
Figure 91:
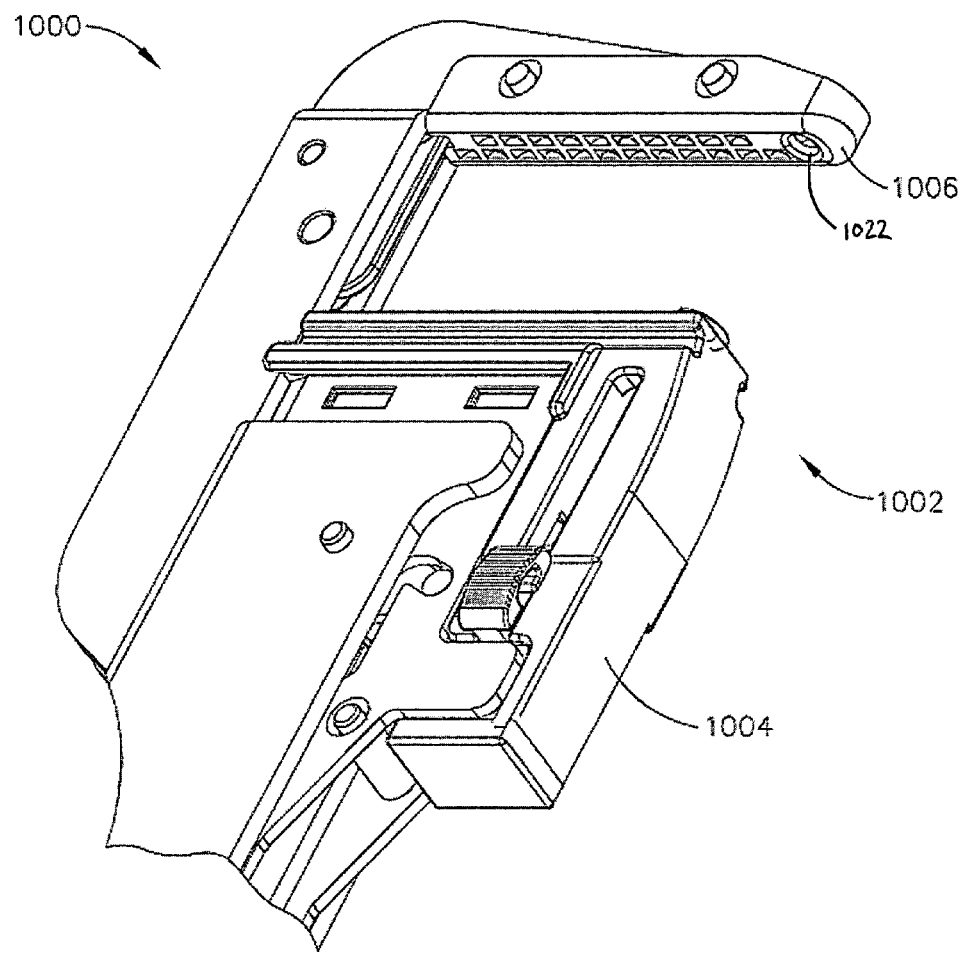

The staple drivers 950, 952 could be of different heights to thereby form different length formed staples (all other things being equal). For example, as shown in the illustrated embodiment, the outer staple drivers 950 may be shorter than the inner staple drivers 952 so that the outer formed staples are longer than the inner formed staples, as shown in FIG. 88. Of course, in other embodiments, the inner staple drivers 952 could be shorter than the outer staple drivers 950. Further, the outer staple drivers 950 may not be a uniform height; there could be height variation among the outer staple drivers 950. Similarly, there could be height variation among the inner staple drivers 952.

In addition, staples with different pre-formation prong heights could be used. Also, the staple forming pockets 202 in the surface forming surface 924 of the anvil 904 may have varying depths to thereby vary the length of the formed staples. Also, as described above, some or all of the staple drivers 950, 952 may have a dimple configuration at their interface with the staples 914 to accommodate staples of different wire diameters or some other configuration that accommodates staples of different wire diameters (e.g., a v-shaped staple channel). Also, some of the pockets 202 in the anvil 1006 may be formed in a compliant material portion of the anvil 1006. Also, the staples 914 could be made of materials that have a different modulus of elasticity.

In other embodiments, as shown in FIGS. 90-95, the present invention is directed to a linear stapler 1000 that is capable of forming staples of different heights. FIGS. 90-95 focus on the end effector 1002 for such a linear stapler 1000. The end effector 1002 may comprise a replaceable staple cartridge 1004 and a linear anvil 1006. The cartridge 1004 comprises staples which are driven into and formed by the anvil 1006 when the device 1000 is actuated. Unlike the endocutters described before, the anvil 1006 may be non-rotatable in the linear stapler 1000. To clamp tissue in the end effector 1002, the user may squeeze a clamping trigger (not shown), which causes the cartridge 1004 to slide distally toward the anvil 1006 from a closed position to a closed position, More details regarding the operation and components of a liner stapler may be found in U.S. Pat. No. 5,697,543, entitled "Linear Stapler With Improved Firing Stroke," by M. Burdorff ("the '543 patent"), which is incorporated herein by reference. Typically, such linear staplers do not comprise a cutting instrument.

Figure 92:
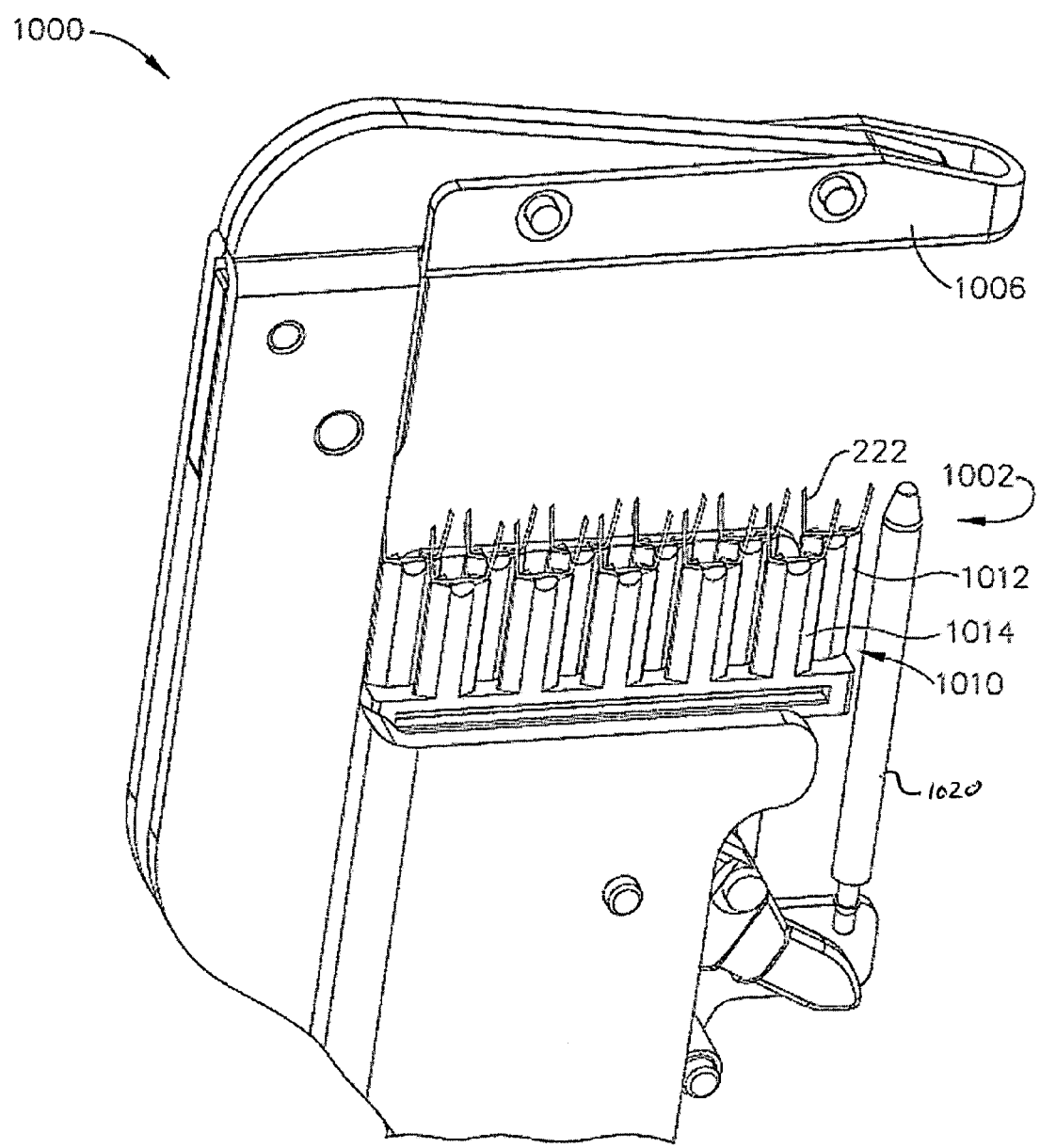
Figure 93:
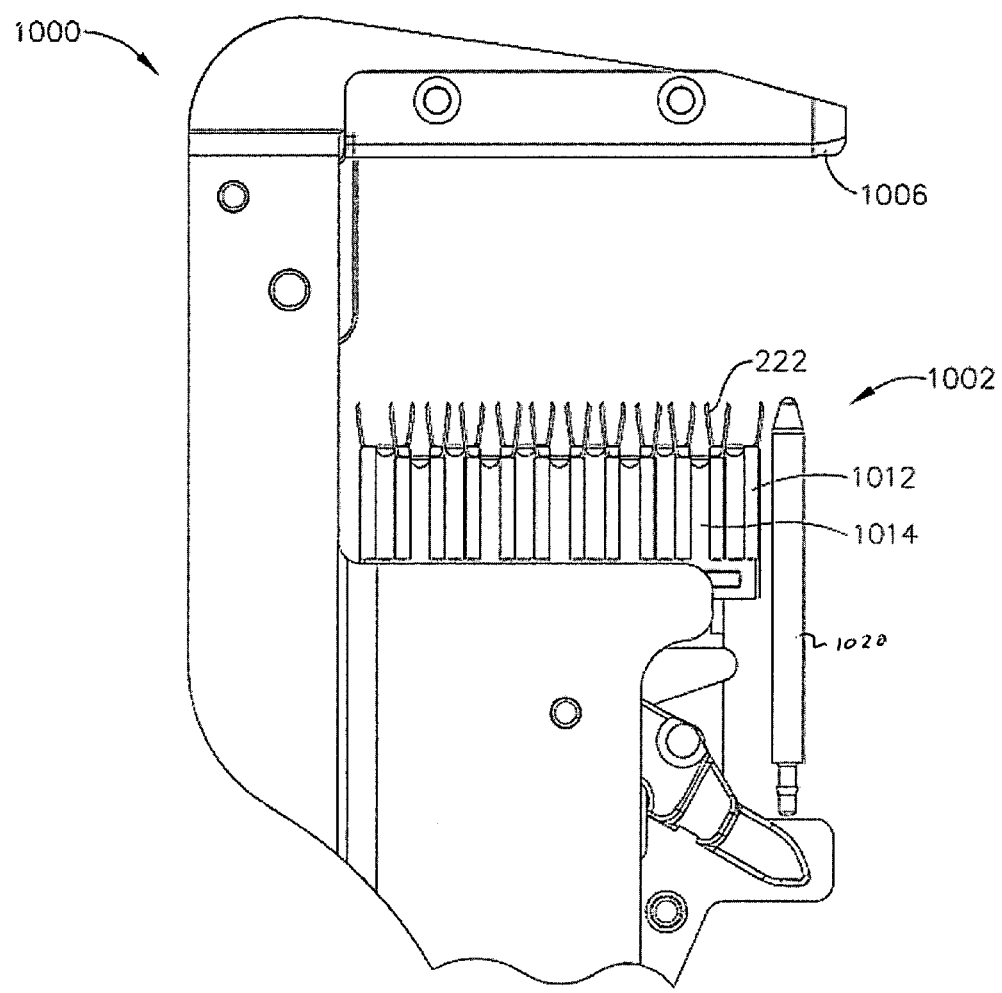
Figure 94:
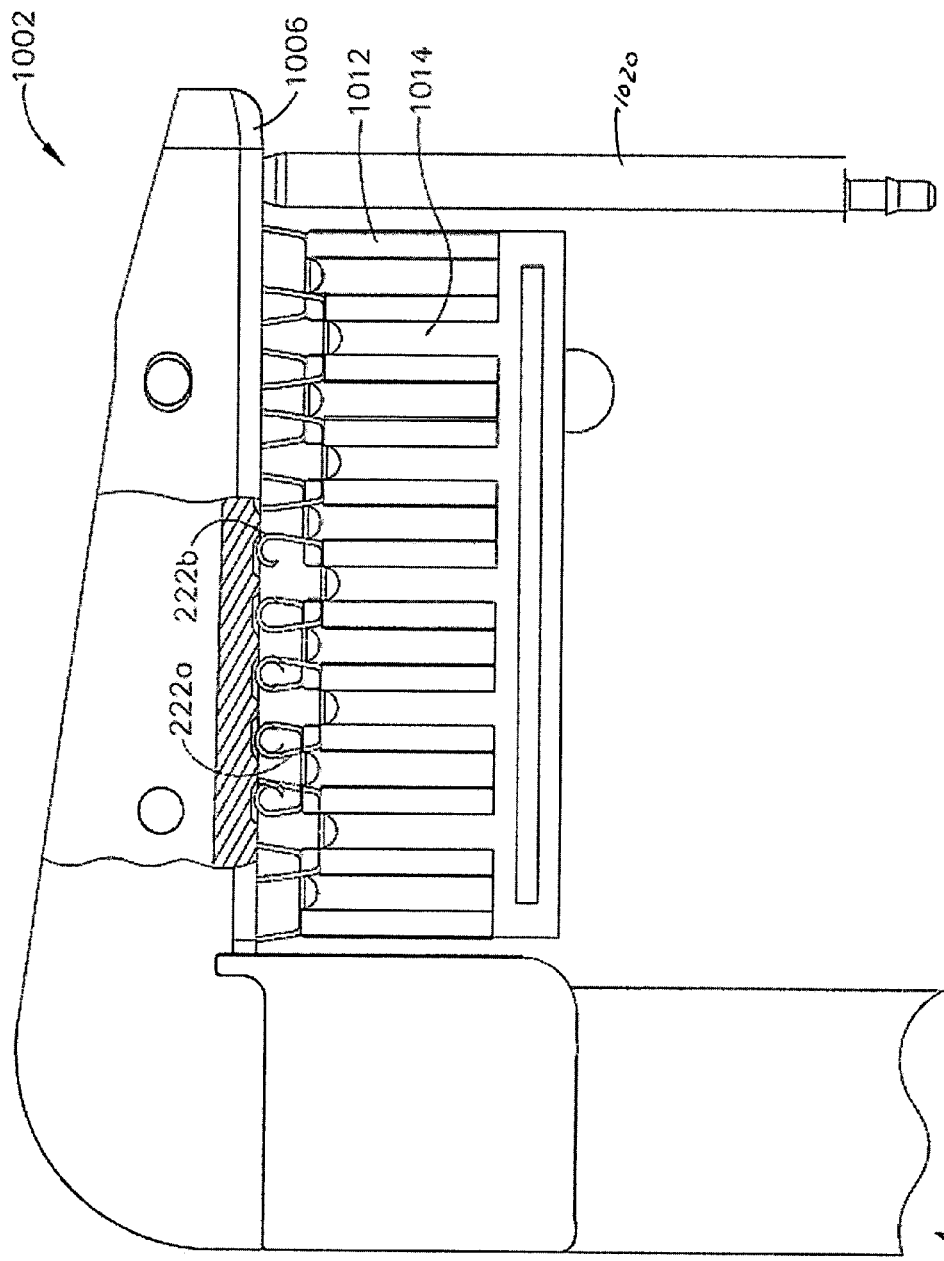
Figure 95:
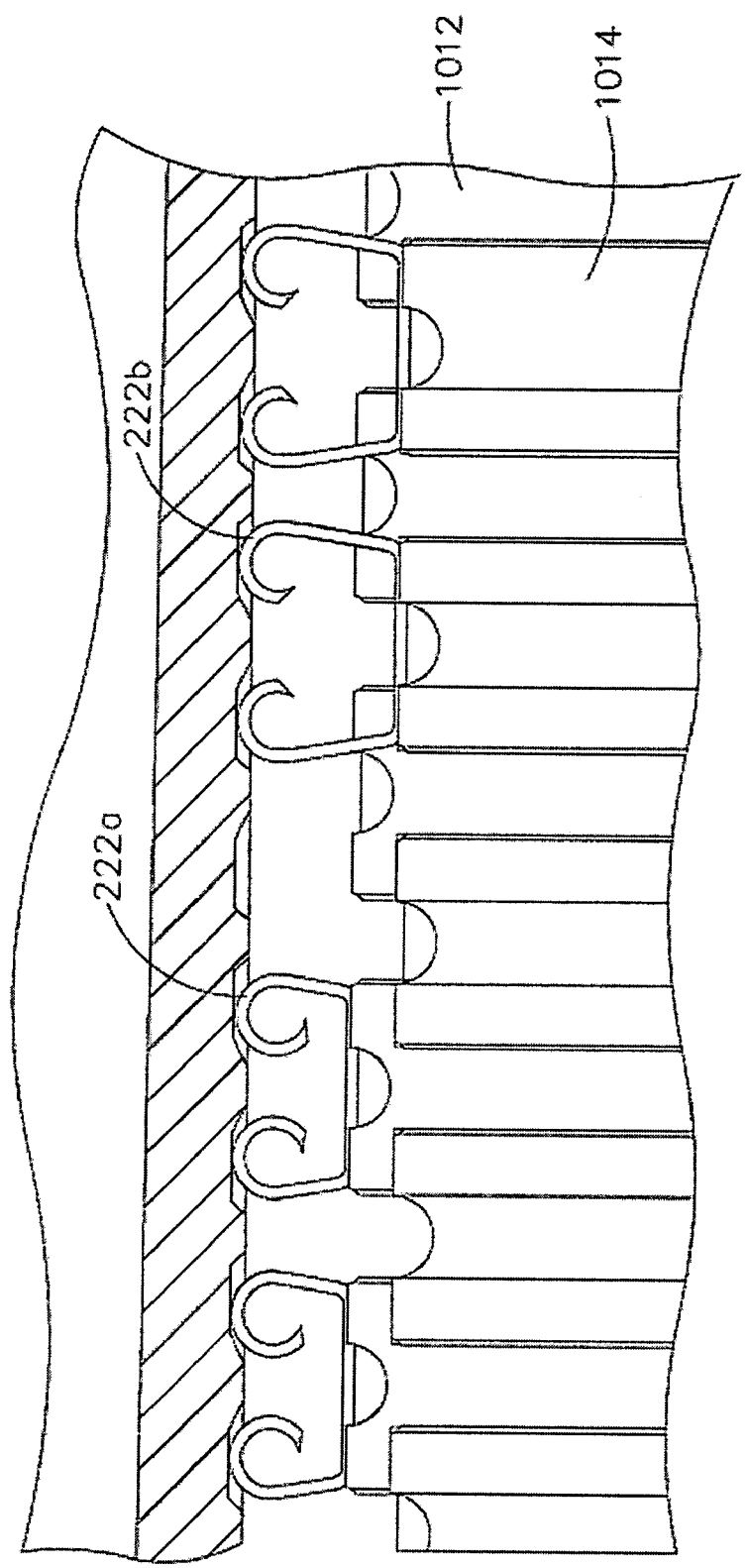

FIGS. 92-93 show the end effector 1002 with the outer cover of the cartridge 1004 removed. As can be seen in these figures, the staple cartridge 1004 may comprise a staple driver assembly 1010 comprising a row of inner staple drivers 1012 and a row of outer staple drivers 1014. The staple drivers 1012, 1014 could be of different heights to thereby form different length formed staples (all other things being equal). For example, as shown in the illustrated embodiment, the outer staple drivers 1014 may be shorter than the inner staple drivers 1012 so that the outer formed staples 222b are longer than the inner formed staples 222a, as shown in FIGS. 94-95.

Of course, in other embodiments, the inner staple drivers 1012 could be shorter than the outer staple drivers 1014. Further, the outer staple drivers 1014 may not be a uniform height; there could be height variation among the outer staple drivers 1014. Similarly, there could be height variation among the inner staple drivers 1012. Also, the cartridge 1004 may comprise, for example, three rows of staples, where the outer two rows have shorter staple drivers and the inner row has longer staple drivers.

In addition, staples 1008 having different pre-formation prong heights could be used. Also, the staple forming pockets 202 in the surface forming surface 1016 of the anvil 1006 may have varying depths to thereby vary the length of the formed staples. Also, as described above, some or all of the staple drivers 1012, 1014 may have a dimple configuration at their interface with the staples 1008 to accommodate staples of different wire diameters or some other configuration that accommodates staples of different wire diameters (e.g., a v-shaped staple channel). Also, some of the pockets 202 in the anvil 1006 may be formed in a compliant material portion of the anvil 1006. Also, staples 1008 of different materials could be used.

In operation, as described in more detail in the '543 patent, when the clamping trigger is retracted by the user, the anvil 1006 is cause to slide proximally toward the staple cartridge 1004 into the closed position to clamp tissue in the end effector 102. The cartridge 1004 may comprise a distally-extending tissue retaining pin 1020 that engages an opening 1022 in the anvil when the end effector 1002 is in the closed position to retain the tissue between the cartridge 1004 and the anvil 1002. When the clinician retracts the separate firing trigger (not shown), a distally extending firing bar (not shown) is actuated, which actuates the staple drivers 1010 to drive the staples 1008.

In another embodiment, the linear stapler 1000 could be configured so that the staple cartridge 1004 slides distally toward the anvil when the clamping trigger is actuated.

It should be recognized that stapling devices according to the present invention may combine some of the features described herein for creating staples of different formed lengths. For example, for embodiments having different staple crushing distances, the staples may all have the same pre-formation prong length or some staples may have different pre-formation prong lengths. Also, the staples may all be made out of the same material, or staples made of different materials, with different modulus of elasticity, could be used. Also, the staple wire diameters may all be the same or some of them could be different.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the various embodiments of the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, steam.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. The various embodiments of the present invention represent vast improvements over prior staple methods that require the use of different sizes of staples in a single cartridge to achieve staples that have differing formed (final) heights.

Accordingly, the present invention has been discussed in terms of endoscopic procedures and apparatus. However, use herein of terms such as "endoscopic" should not be construed to limit the present invention to a surgical stapling and severing instrument for use only in conjunction with an endoscopic tube (i.e., trocar). On the contrary, it is believed that the present invention may find use in any procedure where access is limited to a small incision, including but not limited to laparoscopic procedures, as well as open procedures. Moreover, the unique and novel aspects of the various staple cartridge embodiments of the present invention may find utility when used in connection with other forms of stapling apparatuses without departing from the spirit and scope of the present invention.

What is claimed is:

1. A surgical method comprising:
   clamping tissue in an end effector of a surgical instrument between an anvil and a staple cartridge of the end effector; and
   selectively and separately actuating in succession two or more levels of a plurality of wedge band stacks, each wedge band stack comprising two or more vertically stacked wedge bands, each wedge band comprising a wedge cam at its distal end for driving certain staple drivers in the staple cartridge when the wedge band is actuated, wherein a first of the two wedge bands in the stacks rides on a second of the two wedge bands in the stacks such that the staple drivers are driven in successive stages by the at least two wedge bands when the wedge bands are driven separately in succession, wherein the cumulative height of a first of the plurality of stacked wedge band sets is less than a cumulative height of a second of the plurality of stacked wedge band sets.

2. The method of claim 1, further comprising actuating a cutting instrument in the end effector to cut the tissue clamped in the end effector.

3. The method of claim 2, wherein actuating the cutting instrument occurs after the selective actuation of the wedge bands of the wedge band stacks.

4. The method of claim 2, wherein the wedge band stacks each comprise three separately actuatable stacked wedge bands.

5. The method of claim 2, wherein actuating the cutting instrument occurs simultaneously with actuation of one of the levels of the wedge band stacks.

6. The method of claim 1, wherein the wedge band stacks each comprise three separately actuatable stacked wedge bands.

7. A surgical stapling device comprising:
   an end effector comprising:
      an anvil having a staple forming surface; and
      a staple cartridge facing the staple forming surface of the anvil, wherein the staple cartridge further comprises:
         a plurality of staples; and
         a plurality of staple drivers moveably supportable within the staple cartridge, each staple driver in contact with one of the staples and configured such that when the staple drivers are actuated, the staple drivers drive the staples through the staple cartridge so that the staples are formed against the staple forming surface of the anvil; and
      a plurality of actuatable wedge band sets, each stacked wedge band set comprising at least two vertically stacked, different-level, separately actuatable wedge bands for axially traversing the end effector, wherein each wedge band comprises a wedge cam at its distal end for driving certain ones of the staple drivers when the wedge band is actuated, wherein a first of the two wedge bands in the stacks rides on a second of the two wedge bands in the stacks such that the staple drivers are driven in successive stages by the at least two wedge bands when the wedge bands are driven separately in succession, wherein the cumulative height of a first of the plurality of stacked wedge band sets is less than a cumulative height of a second of the plurality of stacked wedge band sets.

8. The surgical stapling device of claim 7, wherein each wedge band set comprises three stacked wedge bands.

9. The surgical stapling device of claim 8, wherein the plurality of actuatable wedge band sets comprises:
   two outer wedge band sets for driving two outer rows of the staple drivers; and
   two inner wedge band sets for driving two inner rows of the staple drivers.

10. The surgical stapling device of claim 7, wherein a first plurality of the plurality of staple drivers have a first height and a second plurality of the staple drivers have a second height, wherein the first height is less than the second height.

11. The surgical stapling device of claim 7, wherein the end effector further comprises a cutting instrument for axially traversing the end effector to cut tissue clamped in the end effector.

12. The surgical stapling device of claim 11, further comprising a firing bar for firing the cutting instrument.

13. The surgical stapling device of claim 12, further comprising:
   a shaft assembly connected to the end effector; and
   a handle assembly connected to the shaft assembly.

14. The surgical stapling device of claim 13, wherein the shaft assembly houses the wedge band stacks.

15. The surgical stapling device of claim 14, further comprising a wedge band guide at a distal end of the shaft assembly having channels for guiding the wedge bands into the end effector when actuated.

16. The surgical stapling device of claim 7, wherein at least one of the plurality of staple driver has an upper staple supporting surface that supports staples of different wire diameters in an upright position.

17. A surgical stapling device comprising:
an end effector comprising:
an anvil comprising a staple forming surface;
a plurality of staples facing the staple forming surface;
a plurality of staple drivers, each staple driver in contact with one of the staples and configured such that when the staple drivers are actuated, the staple drivers drive the staples through the staple cartridge so that the staples are formed against the staple forming surface of the anvil; and
a shaft assembly connected to the end effector, wherein the shaft assembly houses a plurality of actuatable wedge band sets, each stacked wedge band set comprising at least two vertically stacked, different-levels, separately actuatable wedge bands for axially traversing the end effector, wherein each wedge band comprises a wedge cam at its distal end for driving certain ones of the staple drivers when the wedge band is actuated, wherein a first of the two wedge bands in the stacks rides on a second of the two wedge bands in the stacks such that the staple drivers are driven in successive stages by the at least two wedge bands when the wedge bands are driven separately in succession, wherein the cumulative height of a first of the plurality of stacked wedge band sets is less than a cumulative height of a second of the plurality of stacked wedge band sets.

18. The surgical stapling device of claim 17, wherein the end effector further comprises a cutting instrument for axially traversing the end effector to cut tissue clamped in the end effector.

19. The surgical stapling device of claim 18, further comprising a firing bar for firing the cutting instrument.

20. The surgical stapling device of claim 19, further comprising a wedge band guide at a distal end of the shaft assembly having channels for guiding the wedge bands into the end effector when actuated.

* * * * *